US011364305B2

(12) United States Patent
Serafini et al.

(10) Patent No.: US 11,364,305 B2
(45) Date of Patent: *Jun. 21, 2022

(54) NANOPARTICLE CONJUGATES AND USES THEREOF

(71) Applicant: UNIVERSITY OF MIAMI, Miami, FL (US)

(72) Inventors: Paolo Serafini, Miami Shores, FL (US); Jennifer Vella, Lebanon, NH (US); Vincenzo Bronte, Verona (IT); Pirouz Daftarian, Palmetto Bay, FL (US); Angel Kaifer, Coral Gables, FL (US); Serena Zilio, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,667

(22) Filed: Feb. 17, 2020

(65) Prior Publication Data
US 2020/0237928 A1    Jul. 30, 2020

Related U.S. Application Data

(63) Continuation-in-part of application No. 15/553,855, filed as application No. PCT/US2016/020627 on Mar. 3, 2016, now Pat. No. 10,561,741.

(60) Provisional application No. 62/127,566, filed on Mar. 3, 2015.

(51) Int. Cl.
| | |
|---|---|
| *A61K 47/69* | (2017.01) |
| *C12N 15/113* | (2010.01) |
| *A61K 31/7105* | (2006.01) |
| *C07K 7/06* | (2006.01) |
| *A61K 47/60* | (2017.01) |
| *A61K 38/00* | (2006.01) |

(52) U.S. Cl.
CPC ...... *A61K 47/6935* (2017.08); *A61K 31/7105* (2013.01); *A61K 47/60* (2017.08); *C07K 7/06* (2013.01); *C12N 15/113* (2013.01); *A61K 38/00* (2013.01); *C12N 2310/141* (2013.01); *C12N 2310/531* (2013.01)

(58) Field of Classification Search
CPC .. A61K 31/713; A61K 38/00; A61K 47/6935; A61P 35/00; C12N 15/113; C12N 15/1135; C12N 2310/141
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS 10,561,741 B2 *  2/2020  Serafini ............... A61K 31/683
2014/0255358 A1    9/2014  Kalinski et al.

2015/0204887 A1    7/2015  Epstein et al.
2017/0247706 A1    8/2017  Manenti et al.
2018/0064809 A1    3/2018  Ariizumi et al.

FOREIGN PATENT DOCUMENTS

WO    WO-2013/177197 A1    11/2013

OTHER PUBLICATIONS

Albanesi et al., Neutrophils mediate antibody-induced antitumor effects in mice, Blood, 122:3160-4 (2013).
Azab et al., Usefulness of the neutrophil-to-lymphocyte ratio in predicting short- and long-term mortality in breast cancer patients, Ann. Surg. Oncol., 19:217-24 (2012).
Bronte, V., et al. IL-4-induced arginase 1 suppresses alloreactive T cells in tumor-bearing mice, J. Immunol., 170:270-8 (2003).
Caruso et al., Prognostic value of intratumoral neutrophils in advanced gastric carcinoma in a high-risk area in northern Italy, Mod. Pathol., 15:831-7 (2002).
Cheng et al., A critical role for Stat3 signaling in immune tolerance, Immunity, 19:425-36 (2003).
Condamine et al., Regulation of tumor metastasis by myeloid-derived suppressor cells, Annu. Rev. Med., 66:97-110(2015).
Donskov et al., Impact of immune parameters on long-term survival in metastatic renal cell carcinoma, J. Clinical Oncol., 24:1997-2005 (2006).
Eruslanov et al., Tumor-associated neutrophils stimulate T cell responses in early-stage human lung cancer, J. Clin. Invest., 124:5466-80 (2014).
Fossati et al., Neutrophil infiltration into human gliomas, Acta. Neuropathologica, 98:349-54 (1999).
Gabrilovich et al., Myeloid-derived suppressor cells as regulators of the immune system, Nat. Rev. Immunol., 9:162-74(2009).
Gabrilovich et al., The terminology issue for myeloid-derived suppressor cells, Cancer Res., 67:425 (2007).
Gabrilovich et al., Coordinated regulation of myeloid cells by tumours, Nat. Rev. Immunol., 12:253-68 (2012).
Galizzi et al., Internalization of human interleukin 4 and transient down-regulation of its receptor in the CD23-inducible Jijoye cells, J. Biol. Chem., 264:6984-9 (1989).
Gallina et al., Tumors induce a subset of inflammatory monocytes with immunosuppressive activity on CD8+ T cells, J. Clin. Invest., 116:2777-90 (2006).
Gray et al., Dendrimeric Bowties Featurting Hemispheric-Selective Decoraiton of Ligands for microRNA—Based Therapy, Biomacromolec., 14(1):101-9 (2013).
Greten et al., Myeloid derived suppressor cells in human diseases, Int. Immunopharmacol., 11:802-7 (2011).
Hage et al., Crystal structure of the interleukin-4/receptor alpha chain complex reveals a mosaic binding interface, Cell, 97:271-81 (1999).
Hernandez-Ilizaliturri et al., Neutrophils contribute to the biological antitumor activity of rituximab in a non-Hodgkin's lymphoma severe combined immunodeficiency mouse model, Clin. Cancer. Res., 9, 5866-5873 (2003).

(Continued)

*Primary Examiner* — Jane J Zara
(74) *Attorney, Agent, or Firm* — Marshall, Gerstein & Borun LLP

(57) ABSTRACT

Described herein are nanoparticle-based compositions, kits and methods and platforms for delivering one or more nucleic acids to a cell.

10 Claims, 25 Drawing Sheets

Specification includes a Sequence Listing.

(56) References Cited

OTHER PUBLICATIONS

Hirt et al. Colorectal carcinoma infiltration by myeloperoxidase-expressing neutrophil granulocytes is associated with favorable prognosis, Oncoimmunology, 2:e25990 (2013).
Horuk, BX471: a CCR1 antagonist with anti-inflammatory activity in man, Mini Rev. Med. Chem., 5:791-804 (2005).
International Preliminary Report on Patentability, European Patent Office, dated Sep. 5, 2017.
International Search Report and Written Opinion of the International Searching Authority, European Patent Office, dated Aug. 11, 2016.
Jensen et al., Presence of intratumoral neutrophils is an independent prognostic factor in localized renal cell carcinoma, J. Clin. Oncol., 4709-17 (2009).
Kortylewski et al. Inhibiting Stat3 signaling in the hematopoietic system elicits multicomponent antitumor immunity, Nat. Med., 11:1314-21 (2005).
Marigo et al., Tumor-induced tolerance and immune suppression depend on the C/EBPbeta transcription factor, Immunity, 32:790-802 (2010).
Marvel et al., Myeloid-derived suppressor cells in the tumor microenvironment: expect the unexpected, J. Clin. Invest., 125:3356-64 (2015).
Niitsu et al., Phase I/II study of the rituximab-EPOCT regimen in combination with granulocyte colony—stimulating factor in patients with relapsed or refractory follicular lymphoma including evaluation of its cardiotoxicity using B-type natriuretic peptide and troponin T levels, Clin. Cancer Res., 11:697-702 (2005).
Noh et al., Usefulness of pretreatment neutrophil to lymphocyte ratio in predicting disease-specific survival in breast cancer patients, J. Breast Can., 16:55-9 (2013).
Roth et al. Aptamer-Mediated Blockade of IL4Rαlpha Triggers Apoptosis of MDSCs and Limits Tumor Progression, Cancer Res., 72, 1373-1383 (2012).
Reid et al., Tumor-infiltrating neutrophils in pancreatic neoplasia, Mod. Pathol., 24:1612-19 (2011).
Sagiv et al., Phenotypic diversity and plasticity in circulating neutrophil subpopulations in cancer, Cell reports, 10:562-73 (2015).
Serafini et al., Functionalized dendrimer for the in vivo specific genetic regulation of tumor immunity, Immunol., 137(1):711-2 (2012).
Serafini, Myeloid derived suppressor cells in physiological and pathological conditions: the good, the bad, and the ugly, Immunol. Res., 57:172-84 (2013).
Sonda et al., miR-142-3p prevents macrophage differentiation during cancer-induced myelopoiesis, Immunity, 38:1236-49 (2013).
Steidl et al. Tumor-associated macrophages and survival in classic Hodgkin's lymphoma, N. Engl. J. Med., 362:875-85 (2010).
Stockmeyer et al. Polymorphonuclear granulocytes induce antibody-dependent apoptosis in human breast cancer cells, J. Immunol., 171:5124-9 (2003).
Tomalia et al. Polym. J., 17:117-32(1985).
Trellakis et al. Peripheral blood neutrophil granulocytes from patients with head and neck squamous cell carcinoma functionally differ from their counterparts in healthy donors, Internat. J. Immunopathol. Pharmacol., 24:683-93 (2011).
Van Der Ryst et al., A CCR5 Antagonist for the Treatment of HIV-1 Infection, Frontiers in Immunol., 6:277 (2015).
Vasquez-Dunddel et al., STAT3 regulates arginase-1 in myeloid-derived suppressor cells from cancer patients, J. Clin. Invest., 123:1580-9 (2013).
Weed et al., Tadalafil reduces myeloid-derived suppressor cells and regulatory T cells and promotes tumor immunity in patients with head and neck squamous cell carcinoma, Clin. Cancer Res., 21:39-48 (2015).
Yao et al. Identification of core functional region of murine IL-4 using peptide phage display and molecular modeling, Int. Immunol., 18:19-29 (2006).
Yang et al., Expansion of myeloid immune suppressor Gr+CD11b+ cells in tumor-bearing host directly promotes tumor angiogenesis, Cancer Cell., 6:409-21 (2004).
Youn et al., Epigenetic silencing of retinoblastoma gene regulates pathologic differentiation of myeloid cells in cancer, Nat. Immunol., 14:211-20 (2013).
Zhang et al., CC chemokine ligand 2 (CCL2) promotes prostate cancer tumorigenesis and metastasis, Cytokine Growth Factor Rev., 21:41-8 (2010).
Zhang et al., The high-affinity interaction of human IL-4 and the receptor alpha chain is constituted by two independent binding clusters, J. Mol. Biol., 315:399-407 (2002).

* cited by examiner

Conjugation to the dendrimer increase the affinity/avidity to the IL4Ra

-

CT26 bearing Balb/c → CD112b purification → Transfection siRNA CTRL dendrimer siRNA 4PD

4PD mediate siRNA silencing in the immortalized MDSC-cell line MSC2

4PD mediated STAT3 and C/EBPβ silencing promote tumor regression and mice survival when combined with vaccination

4PD can be used to deliver therapeutic microRNA to TEMC

SEQUENCE LISTING

```
<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: Xaa is Abu (alpha-amino-n-butyric acid)
<220> FEATURE:
<221> NAME/KEY: MISC_FEATURE
<222> LOCATION: (13)..(13)
<223> OTHER INFORMATION: Xaa is Ahx (aminohexanoic acid linker)
<220> FEATURE:
<221> NAME/KEY: MISC_FEATURE
<222> LOCATION: (14)..(14)
<223> OTHER INFORMATION: C-terminal amidation

<400> SEQUENCE: 1

Leu Gln Arg Leu Phe Arg Ala Phe Arg Xaa Leu Asp Xaa Cys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

```
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 2

Arg Xaa Xaa Arg Xaa Xaa Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 3

Arg Xaa Xaa Arg Xaa Xaa Xaa Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 4

Arg Xaa Xaa Xaa Arg Xaa Xaa Xaa Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 5

Arg Xaa Xaa Xaa Arg Xaa Xaa Arg
1               5
```

NANOPARTICLE CONJUGATES AND USES THEREOF

Incorporated by reference in its entirety is a computer-readable nucleotide/amino acid sequence listing submitted concurrently herewith and identified as follows: ASCII (text) file named "49323B_SeqListing.txt," 2,469 bytes, created on Feb. 17, 2020.

BACKGROUND

Nanotechnology has been suggested to be one of the critical research endeavors of the early 21st century, as scientists reveal the unique properties of atomic and molecular assemblages built at the nanometer scale. Nanotechnology is often defined as research and technology development at the atomic, molecular, or macromolecular scale, leading to the controlled creation and use of structures, devices, and systems with a length scale of 1 to 100 nanometers (nm). Nanotechnology manifests itself in a wide range of materials (such as carbon nanotubes and gold nanoshells) and particles (such as fullerenes and dendrimers).

Dendrimers are nanoparticles that are composed of a central core and branched monomers. Each dendrimer is globular in shape and includes a large number of end groups known as surface or terminal groups. This configuration is the result of the cyclic manner in which the dendrimer is built. The more branches added to the core, the higher generation of dendrimer formed. For example, polyamidoamine dendrimers are based on an ethylenediamine core, and branched units are constructed from methyl acrylate and ethylenediamine (Tomalia, D. A. et al. Polym. J. 17:117-132, 1985). The specific structure of the dendrimer has been suggested to make dendrimers suitable for a variety of biomedical applications including oligonucleotide transfection agents and drug carriers.

Myeloid derived suppressor cells (MDSCs) are a population of early myeloid cells that are expanded in various disease states including cancer and are capable of suppressing the immune response (Gabrilovich et al., Nat. Rev. Immunol., 9:162-174, 2009 and Greten et al., Int. Immunopharmacol., 11:802-807, 2011, the disclosures of which are incorporated herein by reference in their entireties). IL4Rα is a functional marker of myeloid derived suppressor cells, of tumor associated macrophage, and tumor induced inflammatory monocytes [1-4].

SUMMARY

Described herein are nanoparticle-based compositions, kits and methods and platforms for delivering one or more nucleic acids to a cell. In some embodiments, the cell is a myeloid cell, a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, or a megakaryocyte-erythroid progenitor (MEP) cell. Also described herein are nanoparticle-based compositions, kits and methods and platforms for delivering one or more nucleic acids to a cell that expresses IL4Rα. In some embodiments, the cell is a myeloid cell, a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, or a megakaryocyte-erythroid progenitor (MEP) cell. In one aspect, described herein is a nanoparticle comprising a charged polymeric dendrimer conjugate to a peptide that specifically binds to a peptide expressed on myeloid cells. In another aspect, the nanoparticle comprises a charge polymeric dendrimer conjugated to a peptide that specifically binds to a peptide expressed on a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, or a megakaryocyte-erythroid progenitor (MEP) cell.

In another aspect, described herein is a nanoparticle comprising a charged polymeric dendrimer conjugated to peptide that specifically binds to IL4Rα expressed on a cell. In some embodiments, the cell that expresses IL4Rα is selected from the group consisting of a myeloid cell, a B cell, a tumor cell, a tumor stromal cell, a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, and a megakaryocyte-erythroid progenitor (MEP) cell. In some embodiments, the cell is a myeloid cell. In some embodiments, the myeloid cell is a tumor educated myeloid cell, a tumor associated-associated macrophage, a M2 (i.e., tumor-associated) macrophage, a monocyte, an immature myeloid cell or a myeloid derived suppressor cell.

In various embodiments, the nanoparticle further comprises one or more nucleic acid molecules (e.g., DNA, RNA, miRNA, siRNA and shRNA). In some embodiments, the nucleic acid is a short hairpin RNA (shRNA). In some embodiments, the shRNA is a STAT1 shRNA, STAT3 shRNA, C-EBPβ shRNA, CCR1 shRNA, CCR2 shRNA or CCR5 shRNA. In some embodiments, a nanoparticle described herein comprises STAT3 shRNA and C-EBPβ shRNA. In some embodiments, a nanoparticle described herein comprises CCR1 shRNA, CCR2 shRNA and CCR5 shRNA.

In some embodiments, the nucleic acid is a miRNA (e.g., miR-142-3p).

The peptide that specifically binds IL4Rα on a cell is preferably a peptide comprising an amino acid sequence selected from the group consisting of RXXRXXR (SEQ ID NO: 2), RXXRXXXR (SEQ ID NO: 3), RXXXRXXXR (SEQ ID NO: 4) and RXXXRXXR (SEQ ID NO: 5). In some embodiments, the peptide that specifically binds to the IL4Rα expressed the cell, e.g., on myeloid cells, is [acetyl-]LQRLFRAFR[Abu]LD[Ahx]-C-amide (SEQ ID NO: 1).

In some embodiments, the nanoparticle comprises a PAMAM dendrimer. In some embodiments, the PAMAM dendrimer is selected from the group consisting of a G4 dendrimer, G5 dendrimer, a G6 dendrimer and a G7 dendrimer.

In another aspect, described herein is a method of delivering a nucleic acid to a cell that expresses IL4Rα comprising contacting the cell with a nanoparticle described herein that comprises one or more nucleic acids described herein.

In another aspect, described herein is a method of screening for nucleic acids that modulate the suppressive activity of a myeloid cell comprising (a) contacting the cell with a nanoparticle comprising (i) a charged polymeric dendrimer conjugated to a peptide that specifically binds to IL4Rα expressed on a tumor educated myeloid cell and (ii) one or more candidate nucleic acids; and (b) determining whether the suppressive activity of the cell is modulated.

In another aspect, described herein is a method of modulating the suppressive activity of a myeloid cell comprising contacting the cell with a composition comprising (i) a charged polymeric dendrimer conjugated to a peptide that specifically binds to IL4Rα expressed on a myeloid cell, and (ii) one or more candidate nucleic acids in an amount effective to modulate the suppressive activity of the cell. In some embodiments, the contacting step occurs in vivo. When the contacting step occurs in vivo, the composition comprises an amphipathic molecule (e.g., cardiolipin, lipids, etc.). In some embodiments, the myeloid cell is a tumor educated myeloid cell, a tumor associated-associated macrophage, a M2 macrophage, a monocyte, an immature myeloid cell or a myeloid derived suppressor cell.

In yet another aspect, described herein is a method of decreasing proliferation of a cancer cell comprising administering a composition comprising a charged polymeric dendrimer conjugated to a peptide that specifically binds to IL4Rα expressed on a myeloid cell, in an amount effective to decrease proliferation of the cancer cell. In some embodiments, the method also decreases tumor progression, induces cancer cell death, causes tumor dormancy and/or antagonizes local diffusion and metastasis formation. When the contacting step occurs in vivo, the composition comprises an amphipathic molecule (e.g., cardiolipin, lipids, etc.). In some embodiments, the myeloid cell is a tumor educated myeloid cell, a tumor associated-associated macrophage, a M2 macrophage, a monocyte, an immature myeloid cell or a myeloid derived suppressor cell.

In another aspect, described herein is a method of repolarizing a myeloid cell into a tumoricidal myeloid cell comprising contacting the protumoral myeloid cell with a composition comprising a nanoparticle described herein in an amount effective to repolarize the myeloid cell into a tumoricidal myeloid cell. The term "repolarizing" as used herein refers to changing the phenotype and function of a cell such for example reverting the phenotype of a myeloid derived suppressor cell to a tumoricidal phenotype. For example, as described in Example 13, contacting a myeloid cell with a nanoparticle described herein resulted in repolarization of the cell from a type 2 tumor favoring phenotype to a type 1 tumoricidal phenotype.

In some embodiments, the protumoral myeloid cell is selected from the group consisting of a myeloid derived suppressor cell, a low density neutrophil, a protumoral monocyte, a tolerogenic myeloid cell, and a tumor associated macrophage. In some embodiments, the tumoricidal myeloid cell is selected from the group consisting of a high density neutrophil, a dendritic cell, and a macrophage polarized toward an M1 phenotype.

In another aspect, described herein is a method of repolarizing a myeloid cell comprising contacting the cell with a CCR1 inhibitor and a CCR5 inhibitor in an amount effective to repolarize the cell. In some embodiments, the CCR1 inhibitor is a small molecule selected from the group consisting of BX471, CCX354, BL5923, BX513, J113863, U35625, AZD-4818, CP-481,715 and MLN3897. In some embodiments, the CCR1 inhibitor comprises a nanoparticle described herein comprising a CCR1 inhibitor nucleic acid. In some embodiments, the CCR5 inhibitor is a small molecule selected from the group consisting of maraviroc, aplaviroc and vicriviroc. In some embodiments, the CCR5 inhibitor comprises a nanoparticle described herein comprising a CCR5 inhibitory nucleic acid.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "a nucleic acid molecule," is understood to represent one or more nucleic acid molecules. As such, the terms "a" (or "an"), "one or more," and "at least one" can be used interchangeably herein.

BRIEF DESCRIPTION OF THE FIGURES

FIG. 2A provides an analysis of mouse and human IL4 binding domains and design of the targeting peptide.

FIG. 2B describes the synthesis of 4PD.

FIG. 3A illustrates the results of mass spectrometry analysis of HPLC purified 4PD dendrimers. Results showed that an average of three targeting peptides were bound to the dendrimer surface and that unreacted components were absent. FIG. 3B describes results of experiments where 4PD were complexed with (gray bar) or without (black bar) cardiolipin to a 43 nucleotide shRNA in the indicated solution. N/P ratio was fixed at 7 and 0.2 ug of cardiolipin were added for each ug of RNA. Size was evaluated by DLS.

In FIG. 6A, the red dot represent the cells transfected with the 4PD nanoparticles (i.e., CD33+IL4Rα+CD11b+CD14+HLADRlow monocytes/MDSC). FIG. 6B depicts the Alexa555 fluorescence in the indicated gates. In FIG. 6C, apparent Kd was calculated by incubating a fixed number of PBMCs with the indicated concentration of Alexa555shRNA/4PD complexes for 10 minutes at 4° C. and by evaluating the MFI in the relevant channel by FACS.

Referring to FIG. 7A, the immortalized cell line MSC-2 was transfected with 4PD loaded with STAT3 specific shRNA (normal or fluorinated), or with irrelevant shRNA. After 48 hours STAT3 expression was evaluated by RT-PCR. Each circle is an independent experiment. With reference to FIG. 7B, mitomicin-treated MSC-2 were transfected with 4PD loaded with STAT3-specific shRNA. Protein expression of STAT3 was evaluated by ELISA four days later.

FIG. 9A illustrates methods to reveal dendrimer immunogenicity. Balb/c mice were treated 7 times 3 times a week with 4PD (14 mg/kg) conjugated with shRNA or PBS. 15 days later the last inoculation mice were sacrificed and the presence of reactive antibody in the sera tested against epoxybeads covalently linked with 4PD, PADRE functionalized dendrimers, or the same dendrimers loaded with the shRNA. Presence of antibodies against PAMAM dendrimer was evaluated by FACS using a rabbit FITC conjugated antibody. FIG. 9B demonstrates that the use of amphipathic molecules (i.e., cardiolipin) abrogates PDD immunogenicity. Mice were treated with 4PD (14 mg/kg) conjugated with shRNA in the presence or in the absence of cardiolipin with the idea that by masking the residual charges, aspecific binding and cytotoxicity and immunogenicity could be drastically reduced. 15 days later the last inoculation mice were sacrificed and the presence of reactive antibody in the sera tested against epoxybeads covalently linked with 4PD. Data showed that addition of cardiolipin in the formulation greatly reduce platform immunogenicity.

With reference to FIG. 14A, gating strategy and example for the tumor of mice treated with scramble shRNA (left panels) or shRNA specific for CCR-1, -2, -5 and -7. A first gate within the alive singlet cells was drawn on the CD11b+ cells; within this gate, cells were differentiated on the basis of the F4/80 and Ly6G expression. TAN were defined as Ly6G+F4/80-cells whereas the F4/80+ cells (red gate and red panel) were further divided on the basis of Ly6G and Ly6C expression as gMDSC (orange gate), mMDSC (pink gate), or TAM (blue gate). Instead, the F4/80-Ly6G– cells (cyan gate and panel) were further divided in Ly6C+SCClowmonocytes and in Ly6C-SCChigheosinophils. With reference to FIG. 14B, IL4Rα expression was evaluated measured in the population described in FIG. 14A.

FIG. 15A depicts an example of T cell proliferation. FIG. 15B summarizes the results of three biological replicas. One way Anova p=p=0.005. P value for post hoc Multiple Comparison Procedures (Holm-Sidak method) is reported.

With reference to FIG. 16A, 5 µm sections of tumor specimen from mice treated either with scramble shRNA or CCRs specific shRNAs were stained with anti-CD3 (red) and DAPI. Images were taken with a 10× magnification on an axiovert fluorescence microscope. Corel Draw was used to re-assemble all acquired fields. Images are representatives of the other three. With reference to FIG. 16B, Balb/c mice were injected in the mammary gland with $5 \times 10^6$ 4T1 cells on day 0. On day 3, 5, 7, 10, and 12, mice were treated intravenously with either a mixture of shRNA specific for CCR-1, -2. -5, and -7 (30 pmoles/g each) or scrambled shRNA. Mice were sacrificed on day 13 and the tumor and the tumor specimen weighted. Data are cumulative of two independent experiments (n=6). T-test p vale is reported.

FIG. 19A provides a graph showing that mouse BM cells were cultured for 4 days with 30% of 4T1 tumor conditioned media (TCM). The suppressive activity of the resulting population was tested against clonotipic T cells stimulated with the relevant peptide (T cell:MDSC ratio=10:1). FIG. 19B provides graphs showing that BM cells were cultured for 24 h in the presence of TCM from the indicated tumor cell lines or with GM-CSF and IL6 (40 ng/ml). CCL3 and CCL4 concentration was evaluated by Cytokine bead array in the original TCM (black) or in the culture supernatants (white). FIG. 19C provides dotplots showing that BM cells were treated as in FIG. 19A in the absence (upper dotplot) or in the presence (lower dotplot) of CCR1 and CCR5 antagonists. The plots are gated in the Lin⁻ Ly6G⁺live population. FIG. 19D provides a graph showing the number of gMDSC and neutrophils recovered per well with the indicated antagonists.

FIG. 20A—T cells proliferation was evaluated 4 days later by FACS. Data showed that mMDSCs differentiated in the presence of CCR1 and CCR5 antagonist (white bar) are less suppressive than the counterpart cultured without any antagonist. FIG. 20B—Ly6G+ cells were cultured with 4T1luciferase cells at the indicated ratio. 24 h later the number of tumor cells in culture was evaluated via luciferase assay. Data showed that Ly6G+ cells differentiated in the presence of CCR1/CCR5 antagonist (white circle) drastically reduce tumor cell number, gMDSCs differentiated in the absence of any antagonist (blue) increase the number of 4T1 recovered compared to 4T1 plated alone (gray). *p<0.05, **p<0.001 n=5

FIG. 22A provides a bar graph showing the results of 4T1 bearing mice were treated 3 times per week with 4PD loaded with scrambled shRNA or shRNAs specific for CCR1 and CCR5 (30 pMoles/gr). On day 13 mice were euthanized and tumor specimens stained with DAPI and antibodies specific for Ly6G and RB1. FIG. 22B provides a graph showing the results of slides being scanned and RB1 MFI within the Ly6G+cells evaluated.

FIG. 22C provides a graph showing the results of tumor infiltrating CD11b+cells (effector, E) from mice treated as in FIG. 22A were sorted and cultured with 4T1-luciferase cells (Target, T). 24 hours later, the number of tumor cells was quantified by luciferase assay. Tumor weight on day 13 is reported. Data derived from 3 experiments.

FIG. 24A shows the gating strategy to identify i) hematopoietic stem cells (HSC), hematopoietic progenitor 1 (HPC1), hematopoietic progenitor 2 (HPC2), Multipotent progenitor (MPP), Common Myeloid progenitor (CMP), Granulocyte-monocyte progenitors (GMP), and megakaryocyte-erythroid progenitor cell (MEP) in a sample. FIG. 24B provides histograms that how the binding of 4PD (open histogram) over the control (filled histogram). The dot blot on the right summarize the binding from ten independent assays.

DETAILED DESCRIPTION

The present invention is based, in part, on the discovery that Interleukin-4 Receptor α (IL4Rα) can be used for targeted delivery of therapeutics (e.g., nucleic acids) to cells that express IL4Rα. IL4Rα, which is expressed on hematopoietic stem and progenitor cells and is upregulated early during their differentiation toward myeloid cells, is part of both Type 1 and Type 2 IL-4 receptors and it is characterized by a fast internalization upon binding of the relevant ligands[5]. Because of its internalization properties, IL4Rα can facilitate the transfection of the therapeutic nucleic acid by facilitating the entrance of the nucleic acid into the cytoplasm of the cells. The Examples provided herein demonstrate that a peptide that specifically binds to IL4Rα expressed on myeloid cells and hematopoietic stem and progenitor cells and can provide targeted delivery of therapeutics to myeloid cells and hematopoietic stem and progenitor cells.

Figure 1:
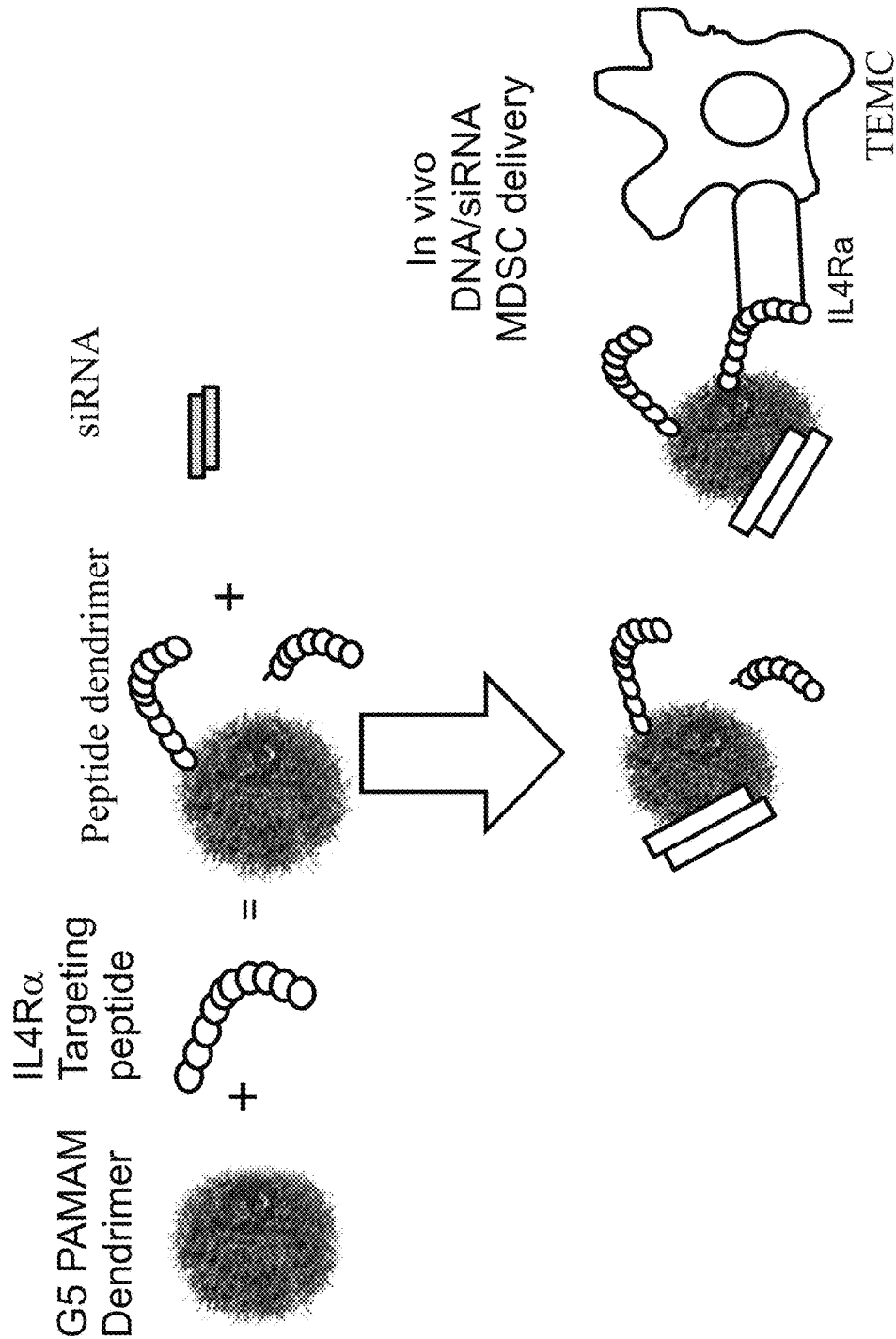
FIG. 1 provides a schematic of the 4PD platform.
Figure 2A:
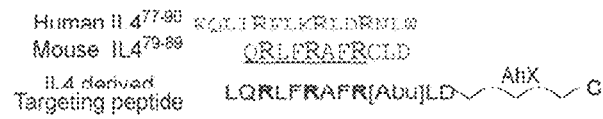
FIGS. 2A and 2B describe the design and synthesis of 4PD.
Figure 2B:
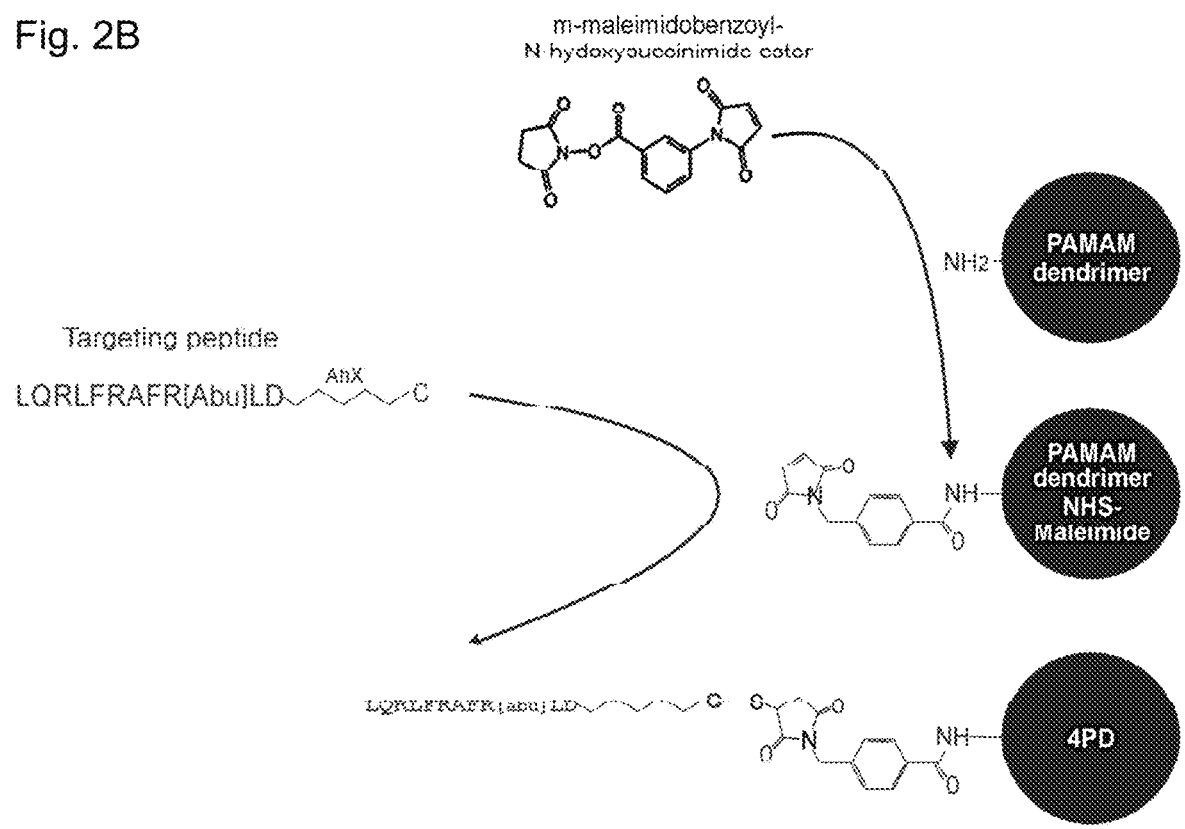

FIG. 1 depicts the general structure of an exemplary nanoparticle of the invention. In various embodiments, one, two, three, or four (or more) IL4-derived, IL4Rα targeting peptides are conjugated via maeidoamide chemistry to a G5 PAMAM dendrimer leaving approximately 125-126 positively charged amide for subsequent interaction with nucleic acid. When shRNA, microRNA, or DNA is added, it spontaneously forms complexes with the functionalized dendrimers that protect them from nuclease and allow their delivery and internalization into the myeloid cells (i.e. MDSCs, monocytes, macrophages and other myeloid cells with protumoral and tolerogenic phenotype).

In one aspect, described herein is a nanoparticle comprising a charged polymeric dendrimer conjugated to an IL4Rα binding peptide that specifically binds to IL4Rα expressed on a cell. By the term "conjugated" is meant when one molecule or agent is physically or chemically coupled or adhered to another molecule or agent. Examples of conjugation include covalent linkage and electrostatic complexation. The terms "complexed," "complexed with," and "conjugated" are used interchangeably herein.

The terms "specifically binds" and "specific binding" as used herein refer to binding which occurs between two components, such as a receptor and its ligand, and which may be mediated by covalent or non-covalent interactions or a combination of covalent and non-covalent interactions. When the interaction of the two components produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction.

As used herein, the term "nanoparticle" means a particle whose size is measured in the nanometers range (i.e., less than 1 µm). In some embodiments, the nanoparticle has a total diameter in the range of approximately 2-500 nm.

Hematopoietic Progenitor and Hematopoietic Stem Cells

The terms "hematopoietic progenitor cell" as used herein refers to an uncommitted (i.e., undifferentiated) and/or partially committed (i.e., partially differentiated) cell. Hematopoietic progenitor cells are oligopotent, that is, they have the ability to differentiate into more than one cell type, comprising, without limitation, granulocytes (e.g., promyelocytes, neutrophils, eosinophils, basophils), erythrocytes (e.g., reticulocytes, erythrocytes), thrombocyte (e.g., megakaryoblasts, platelet producing megakaryocytes, platelets), and monocytes (e.g., monocytes, macrophages).

Hematopoietic progenitor cells can be isolated from peripheral blood after mobilization, bone marrow, or umbilical cord blood. Hematopoietic progenitor cells may also be obtained from stem cells that give rise to hematopoietic cells.

Hematopoietic progenitor cells usually, but not necessarily, reside in the bone marrow. They are also found in the blood circulation and are also resident within other tissues. Hematopoietic progenitor cells are identified by surface markers. For example, human progenitor cells are identified by the surface marker CD34 (CD34+ cells). 0.1% of circulating cells in the blood are CD34+ while 2.1% of bone marrow cells are CD34$^+$. Hematopoietic stem cells resident in tissues have also been found to be CD34$^+$. Bone marrow derived (i.e., isolated from bone marrow or from the circulation) and tissue derived CD34+ cells can differentiate into muscle, neuronal tissues, epithelial tissues, vascular cells, immune cells and others and may be used to repopulate target tissues. Hematopoietic progenitor cells have been used therapeutically to repopulate damaged and disease tissues and spontaneously participate in tissues repair processes and pathologies in vivo (Belicci et. al. (2004) J. Neurosci Res. 77, 475-86; Otani et al., 2002, Nature Med. 8, 1004-1010; Otani et. al., (2004) J. Clin. Invest. 114, 765-774; Tamaki et. al. (2002) J. Cell Biol. 157, 571-577; Torrente et al. (2004) J. Clin. Invest. 114, 182-195; Hashimoto et. al. (2004) J. Clin. Invest. 113, 243-252). Hematopoietic stem and progenitor cells are found in circulation and in the tumor cells of patients with cancer (Wu et al., Proc. Natl. Acad. Sci., 111:4221-4226, 2014).

In some embodiments, hematopoietic progenitor cells includes, but are not limited to endothelial progenitor cells, lymphendothelial progenitor cells, mesenchymal precursor cells, hematopoietic progenitor 1 cells, hematopoietic progenitor 2 cells, multipotent progenitor (MPP) cells, lymphoid progenitor cells, granulocyte-monocyte progenitor cells, macrophage progenitor cells, and megakaryocyte-erythroid progenitor cells.

Hematopoietic progenitor cells may be isolated and cultured using methods disclosed herein as well as those known in the art, such as from blood products (e.g., U.S. Pat. Nos. 5,061,620 and 6,645,489 incorporated by reference).

The terms "hematopoietic stem cell" and "HSC" as used herein refer to an oligopotent cell type that gives rise to more differentiated "precursor cells" such as, without limitation, endothelial progenitor cells, lymphendothelial progenitor cells, mesenchymal precursor cells, myeloid progenitor cells, lymphoid progenitor cells, granulocyte progenitor cell, macrophage progenitor cells, megakaryocyte progenitor cells, erythroid progenitor cells, Pro-B cells and Pro T cells (Terskikh et. al. (2003) supra). HSCs reside in the bone marrow, often attached to bone, but are also found in the circulation and also resident within other tissues. Hematopoietic stem cells have the capacity for self-renewal while more committed progenitors do not (Terskikh et. al. (2003) supra). HSCs and HPCs share common cell surface markers, in particular, for human cells by the marker CD34. HSCs are Lineage negative (lacking specific markers for any differentiated cells, such as B220 on B cells, CD3 on T-cells, CD11b on myeloid cells, etc.), CD34+, c-kit+ (Belicci et. al. (2004) supra). In mice these cells are c-kit$^+$, Thy1.11o, Sca-1$^+$ and Lin$^-$ (Rafii et al. 2003, supra). Additionally, some progenitors, including endothelial progenitors, express CD133.

In some embodiments, the nanoparticle described herein is capable of targeting a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, or a megakaryocyte-erythroid progenitor (MEP) cell.

Myeloid Cells

Myeloid derived suppressor cells (MDSCs) are a population of early myeloid cells that are expanded in various disease states including cancer and are capable of suppressing the immune response (Gabrilovich et al., Nat. Rev. Immunol., 9:162-174, 2009 and Greten et al., Int. Immunopharmacol., 11:802-807, 2011, the disclosures of which are incorporated herein by reference in their entireties). In mice, MDSCs express myeloid markers (Gr1 or CD11b). In humans, the Gr1 antigen is absent. Human MDSCs express myeloid cell markers such as $CD11b^+$ and $CD33^+$, but are usually negative for lineage specific antigens such as CD3, CD19 and CD57. Monocytic MDSCs are usually characterized by $HLA-DR^{-/low}$, $CD11b^+$, $CD33^+$ and $CD14^+$ phenotype in humans ($CD11b^+$, $Ly6G^-/Ly6G^+$ in mice) whereas mature monocytes express high levels of HLA-DR. Granulocytic MDSCs are usually characterized by $HLA-DR^{-/low}$, $CD11b^+$, $CD33^+$, $CD15^+$ phenotype in humans ($CD11b^+$, $Ly6G^-/Ly6G^{low}$ in mice). MDSCs, monocytic MDSCs and granulocytic MDSCs have all been shown to possess immunosuppressive properties (Filipazzi et al., Cancer Immunol. Immunother., 61:255-263, 2012; Mundy-Bosse et al., Cancer Immunol. Immunother., 60:1269-1271, 2011; Movahedi et al., Blood, 111:4233-4244, 2008, the disclosure of which are incorporated herein by reference in their entireties).

MDSCs can be generated in the bone marrow in response to cancer derived factors such as granulocyte colony stimulating factor (G-CSF), IL-6, granulocyte monocyte colony stimulating factor (GM-CSF), IL1β, prostaglandin E2 (PGE2), tumor necrosis factor α and vascular endothelial growth factor (VEGF) and are recruited to the tumor site by CCL2, CXCL12 and CXCLS. Additional signals stimulate MDSCs to acquire immunosuppressive properties which are mediated through members of the signal transducer and activator of transcription (STAT1, STAT3, STAT6) and nuclear factor kappa light chain enhancer of activated B cells (NFκB) transcription factors (Gabrilovich, supra). Activated MDSCs produce Arginase 1 (ARG1), inducible nitric oxide synthase (NOS2), IDO (indoleamine 2,3-dioxygenase), NADPH oxidase and immunosuppressive cytokines that have the potential to inhibit cytotoxic T lymphocytes (CTLs), dendritic cells and natural killer cells as well as expand $CD4^+CD25^+FoxP3^+$ regulatory T cells (Tregs).

In some embodiments, the nanoparticle described herein is capable of targeting a myeloid cell, including, but not limited to, a granulocytic myeloid cell, a monocytic myeloid cell.

Dendrimers

The term "dendrimer" or "dendrimeric polymer" refers to repeatedly branched nano-sized macromolecules characterized by a symmetrical, well-defined three-dimensional shape. Dendrimers grow three-dimensionally by the addition of shells of branched molecules to a central core. The cores are spacious and various chemical units can be attached to points on the exterior of the central core. Dendrimeric polymers have been described extensively (Tomalia. (1994). Advanced Materials 6:529-539; Donald A. Tomalia, Adel M. Naylor, William A. Goddard III (1990). Angew, Chem. Int. Ed. Engl., 29:138-175; incorporated herein by reference in their entireties). Dendrimeric polymers are synthesized as defined spherical structures typically ranging from 1 to 20 nanometers in diameter. Accordingly, in some aspects, the dendrimers of the dendrimer conjugates provided herein are about 1, about 2, about 3, about 4, about 5, about 6, about 7, about 8, about 9, about 10, about 11, about 12, about 13, about 14, about 15, about 16, about 17, about 18, about 19, or about 20 nm in diameter.

Dendrimers are identified by a generation number (Gn) and each complete synthesis reaction results in a new dendrimer generation. Molecular weight and the number of terminal groups increase exponentially as a function of generation number (the number of layers) of the dendrimer. Different types of dendrimers can be synthesized based on the core structure that initiates the polymerization process. Dendrimers of any generation are used for the invention. For example, the use of G4, G5, G6 and G7 dendrimers are specifically contemplated.

The dendrimer core structures in some aspects dictate several characteristics of the molecule such as the overall shape, density and surface functionality (Tomalia et al. (1990). Angew. Chem. Int. Ed. Engl., 29:138). Spherical dendrimers have ammonia as a trivalent initiator core or ethylenediamine (EDA) as a tetravalent initiator core. Recently described rod-shaped dendrimers (Yin et al (1998). J. Am. Chem. Soc., 120:2678) use polyethyleneimine linear cores of varying lengths; with longer cores leading to increased rod length. Dendritic macromolecules are available commercially in kilogram quantities and are produced under current good manufacturing processes (GMP) for biotechnology applications.

As used herein, the term "dendrimer" or "dendrimeric polymer" also refers to unsymmetrical or asymmetrical dendrimers having more than one radius due to asymmetry of the dendrimer. In some aspects, the asymmetrical dendrimer has two different radii. Such dendrimers and the synthesis thereof are further described in Lee et al., Bioconjugate Chem. 18: 579-584 (2007).

Dendrimers may be characterized by a number of techniques including, but not limited to, electrospray-ionization mass spectroscopy, matrix-assisted laser desorption/ionization-time of flight spectroscopy, 13C nuclear magnetic resonance spectroscopy, high pressure liquid chromatography, size exclusion chromatography with multi-angle laser light scattering, capillary electrophoresis and gel electrophoresis. These tests assure the uniformity of the polymer population and are important for monitoring quality control of dendrimer manufacture for GMP applications and in vivo usage. Extensive studies have been completed with neutralized dendrimers and show no evidence of toxicity when administered intravenously in vivo.

The invention contemplates the use of any type of dendrimer including but not limited to poly(amidoamine) (PAMAM) dendrimers such as dense star polymers and Starburst polymers, poly(amidoamine-organosilicon) (PAMAMOS) dendrimers, (Poly (Propylene Imine)) (PPI) dendrimers, tecto dendrimers, multilingual dendrimers, chiral dendrimers, hybrid dendrimers/linear polymers, amphiphilic dendrimers, micellar dendrimers and Frechet-type dendrimers.

In one embodiment, the dendrimer conjugate comprises a PAMAM dendrimer.

PAMAM dendrimers are a family of water-soluble polymers characterized by a unique tree-like branching architecture and a compact spherical shape in solution. Several classes of PAMAM dendrimers have been synthesized using different cores such as ethylene diamine (EDA) and 1,4-diamino butane (DAB) with different surface groups (e.g., amine, hydroxyl, or carboxyl). PAMAM dendrimers are identified by a generation number (Gn) in the range 0-10 where an increase in Gn denotes a controlled incremental increase in size, molecular weight, and number of surface groups. PAMAM dendrimers are efficient drug carriers due to the high degree of branching and the large number of surface groups, which can be utilized to immobilize drugs, imaging agents, or targeting ligands to achieve a high density of therapeutic molecules in a compact system.

IL4Rα Binding Peptide

It is contemplated that the IL4Rα binding peptide is capable of specifically binding IL4Rα expressed on any cell. For example, in some embodiments, the IL4Rα binding peptide is capable of specifically binding IL4Rα expressed on a cell selected from the group consisting of a myeloid cell, a B cell, a tumor cell, a tumor stromal cell, a hematopoietic stem cell (HSC), a hematopoietic progenitor 1 cell (HPC1), a hematopoietic progenitor 2 cell (HPC2), a multipotent progenitor (MPP) cell, a common myeloid progenitor (CMP) cell, a granulocyte-monocyte progenitor (GMP) cell, and a megakaryocyte-erythroid progenitor (MEP) cell. In some embodiments, the cell is a myeloid cell (e.g., a tumor educated myeloid cell).

The peptide that specifically binds IL4Rα on a cell is preferably a peptide comprising an amino acid sequence selected from the group consisting of RXXRXXR (SEQ ID NO: 2), RXXRXXXR (SEQ ID NO: 3), RXXXRXXXR (SEQ ID NO: 4) and RXXXRXXR (SEQ ID NO: 5), wherein the "X" in SEQ ID NOs: 3-5 can be any amino acid. In some embodiments, the peptide that specifically binds to the IL4Rα expressed on myeloid cells is [acetyl-]LQRLF-RAFR[Abu]LD[Ahx]-C-amide (SEQ ID NO: 1), where Abu represents the non-naturally occurring amino acid alpha-amino-n-butyric acid, and Ahx represents the amino-hexanoic acid linker conjugated to a Cysteine (C) and the maleidoamide ester as a second ester. The inclusion of one or more amino acid substitutions (e.g., conservative substitutions) to the amino acid sequence set forth in SEQ ID NO: 1, wherein the presence of the amino acid substitutions do not alter the ability of the peptide to specifically bind IL4Rα on the surface of the cell, is also contemplated.

Nucleic Acids

In some embodiments, one or nucleic acids are attached to the dendrimer. As used herein, a "nucleic acid" or a "nucleic acid molecule" means a chain of two or more nucleotides such as RNA (ribonucleic acid) and DNA (deoxyribonucleic acid), and chemically-modified nucleotides. Nucleic acid molecules may be in the form of RNA (e.g., mRNA, microRNA, siRNA, shRNA or synthetic chemically modified RNA) or in the form of DNA (e.g., cDNA, genomic DNA, and synthetic DNA). The DNA may be double-stranded or single-stranded, and if single-stranded, may be a coding (sense) strand or a non-coding (anti-sense) strand. RNA may also be present in double-stranded form, if desired. The nucleic acid need not be double-stranded over the entire length of the molecule (i.e., a single strand of nucleic acid may be hybridized to a second strand over a subregion of its sequence).

In some embodiments, the nanoparticle comprises one or more nucleic acids including, but not limited to, siRNAs, siRNA-like molecules, miRNAs, shRNAs, antagomirs, RNA sponge and other nucleic acids with gene silencing activity (e.g., antisense molecules and/or ribozymes), or nucleic acid constructs (e.g., DNA constructs) encoding RNA silencing nucleic acids and other gene silencing nucleic acids.

In some embodiments, the nucleic acid is an siRNA molecule. In some embodiments, the siRNA molecule has a length from 5-60 (e.g., about 10-50) nucleotides, i.e., each strand comprises 5-60 (e.g., 10-50) nucleotides (or nucleotide analogs), although molecules having more than 60 nucleotides in length also are contemplated. In some embodiments, the siRNA molecule has a length from about 5-15 (e.g., 5, 6, 7, 8, 9, 10, 11, 12, 13, 14, or 15); about 16-30 (e.g., 16, 17, 18, 19, 20, 21, 22, 23, 24, 25, 26, 27, 28, 29, or 30); about 18-25 (e.g., 18, 19, 20, 21, 22, 23, 24, or 25); about 25-30 (e.g., 25, 26, 27, 28, 29, or 30); about 25-35 (e.g., 25, 26, 27, 28, 29, 30, 31, 32, 33, 34 or 35); about 30-35 (e.g., 30, 31, 32, 33, 34 or 35); or about 30-60 (e.g., 35, 40, 45, 50, 55, or 60) nucleotides in each strand, wherein one of the strands is sufficiently complementary to a target region, and the other strand is identical or substantially identical to the first strand (e.g., having 5 or fewer (e.g., 1, 2, 3, or 4) mismatches relative to the first strand.

In some embodiments, the strands of the siRNA molecule are of different lengths (e.g., they differ in length by 5 or fewer nucleotides (e.g., 1, 2, 3, or 4)). In other embodiments, the strands of the siRNA molecule are of the same length.

In some embodiments, the strands of the siRNA molecule are aligned such that one or both ends of the siRNA molecule are blunt-ended (i.e., lack an overhang). In other embodiments, the strands of the siRNA molecule are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In certain embodiments, at least one (preferably both) ends of the duplex comprise a 2 nucleotide overhands (e.g., dTdT overhangs).

In some embodiments, the sense strand of the siRNA is designed have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is contemplated. In one embodiment, the sense strand has 4, 3, 2, 1, or 0 mismatched nucleotide(s) with a target region, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition. Sequence identity between one or more nucleic acid sequences may be determined by sequence comparison and alignment algorithms known in the art, such as BLAST and CLUSTALW.

In some embodiments, the nucleic acid is a microRNA (or miRNA). miRNAs are noncoding RNAs of approximately 20-25 (e.g., 22) nucleotides which can regulate gene expression at the post transcriptional or translational level during plant and animal development. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). In some embodiments, the microRNA is selected from the group consisting of miR-142-3p, miR-155, miR-21 (Li et al. J Immunol. 2014 Feb. 1; 192(3):1034-43), miR-706 and miR-455 (Hegde et al., 188: Meeting Abstract Supplement 48.16, 2012).

Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing. Synthetic miRNAs based at least in part on naturally-occurring miRNA sequences are contemplated for use in the context of the invention.

In some embodiments, the nucleic acid is a short hairpin RNA (shRNA). In some embodiments, the shRNA is a STAT1 shRNA, STAT3 shRNA, C-EBPβ shRNA, CCR1 shRNA, CCR2 shRNA or CCR5 shRNA. In some embodiments, a nanoparticle described herein comprises one or more nucleic acids selected from the group consisting of STAT1 shRNA, STAT3 shRNA, C-EBPβ shRNA, CCR1 shRNA, CCR2 shRNA and CCR5 shRNA. In some embodiments, a nanoparticle described herein comprises STAT3 shRNA and C-EBPβ shRNA. In some embodiments, a nanoparticle described herein comprises STAT3 shRNA. In some embodiments, a nanoparticle described herein comprises CCR1 shRNA, CCR2 shRNA and CCR5 shRNA.

In contrast to siRNAs, shRNAs mimic the natural precursors of microRNAs (miRNAs) and enter at the top of the gene silencing pathway. The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. In some embodiments, the stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In some embodiments, the length of the stem portions should be 21 nucleotides or greater. When used in mammalian cells, the length of the stem portions are preferably less than about 30 nucleotides to avoid provoking non-specific responses like the interferon pathway. In non-mammalian cells, the stem can be longer than 30 nucleotides.

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (U's), e.g., all U's. The loop in the shRNAs can be 2, 3, 4, 5, 6, 7, 8, 9, or more, e.g., 15 or 20, or more nucleotides in length.

A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In some embodiments, shRNAs include the sequences of a desired siRNA molecule described above. In some embodiments, the sequence of the antisense portion of a shRNA can be designed essentially as described above or generally by selecting an 18, 19, 20, 21 nucleotide, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA, siRNA-like duplex, or miRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro. In certain embodiments, shRNAs may include miRNA sequences, optionally end-modified miRNA sequences, to enhance entry into RISC.

Chemical modifications may lead to increased stability, e.g., increased or enhanced in vivo stability, compared to an unmodified nucleic acid. Such chemical modifications can also be used to stabilize the first (priming) strand of the siRNA for enhancing RISC activity/RNA silencing responsiveness in a cell (or cell extract or organism) and improve its intracellular half-life for subsequent receipt of the second strand wherein RNA silencing/gene silencing can now progress. Modifications can also enhance properties such as cellular uptake of the RNA silencing agents and/or stability of the RNA silencing agents, can stabilize interactions between base pairs, and can maintain the structural integrity of the antisense RNA silencing agent-target RNA duplex. RNA silencing agent modifications can also be designed such that properties important for in vivo applications, in particular, human therapeutic applications, are improved without compromising the RNA silencing activity of the RNA silencing agents e.g., modifications to increase resistance of, for example, siRNA or miRNA molecules to nucleases. In some embodiments, modified siRNA molecules of the invention can enhance the efficiency of target RNA inhibition as compared to a corresponding unmodified siRNA. In some embodiments, modified nucleotides do not affect the ability of the antisense strand to adopt A-form helix conformation when base-pairing with the target RNA sequence, e.g., an A-form helix conformation comprising a normal major groove when base-pairing with the target RNA sequence.

Chemical modifications generally include end-, sugar-, base- and/or backbone-modifications to the ribonucleotides (i.e., include modifications to the phosphate-sugar backbone). In one embodiment, the RNA silencing agent of the invention comprises one or more (e.g., about 1, 2, 3, or 4) end modifications. For example, modification at the 5' end of an siRNA molecule comprises, for example, a 5'-propylamine group. Modifications to the 3' OH terminus of an siRNA molecule can include, but are not limited to, 3'-puromycin, 3'-biotin (e.g., a photocleavable biotin), a peptide (e.g., a Tat peptide), a nanoparticle, a peptidomimetic, organic compounds (e.g., a dye such as a fluorescent dye), or a dendrimer. End modifications may be on the sense strand, on the antisense strand or both. In some embodiments, the 5' modifications are on the sense strand only.

In some embodiments, the nucleic acid comprises one or more (e.g., about 1, 2, 3, 4, 5, 6, 7, 8, 9, 10, or more) sugar-modified nucleotides. Sugar-modified nucleotides include, but are not limited to: 2'-fluoro modified ribonucleotides, 2'-OMe modified ribonucleotides, 2'-deoxy ribonucleotides, 2'-amino modified ribonucleotides and 2'-thio modified ribonucleotides. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. In one embodiment, the sugar-modified nucleotide is a 2'-fluoro ribonucleotide. In some embodiments, when a 2'-deoxy ribonucleotide is present, it is upstream of the cleavage site referencing the antisense strand or downstream of the cleavage site referencing the antisense strand. The 2'-fluoro ribonucleotides can be in the sense and antisense strands. In some embodiments, the 2'-fluoro ribonucleotides are every uridine and cytidine. In other embodiments, the 2'-fluoro ribonucleotides are only present at the 3' and 5' ends of the sense strand, the antisense strand or both.

In some embodiments, the nucleic acid comprises one or more (e.g., about 1, 2, 3, 4, 5, 6, 7, 8, 9, 10, or more) nucleobase-modified nucleotides. Nucleobase-modified nucleotides useful in the invention include, but are not limited to: uridine and/or cytidine modified at the 5-position (e.g., 5-bromo-uridine, 5-(2-amino)propyl uridine, 5-amino-allyl-uridine, 5-iodo-uridine, 5-methyl-cytidine, 5-fluoro-cytidine, and 5-fluoro-uridine), ribo-thymidine, 2-aminopurine, 2,6-diaminopurine, 4-thio-uridine, adenosine and/or guanosines modified at the 8 position (e.g., 8-bromo guanosine), deaza nucleotides (e.g., 7-deaza-adenosine), O- and N-alkylated nucleotides (e.g., N6-methyl adenosine) and non-nucleotide-type bases (e.g., deoxy-abasic, inosine, N3-methyl-uridine, N6, N6-dimethyl-adenosine, pseudouridine, purine ribonucleoside and ribavirin).

In some embodiments, the nucleic acid comprises one or more (e.g., about 1, 2, 3, 4, 5, 6, 7, 8, 9, 10, or more) backbone-modified nucleotides. Exemplary backbone-modified nucleotides contain a phosphorothioate group or a phosphorodithioate. In another embodiment, a backbone modification of the invention comprises a phosphonoacetate and/or thiophosphonoacetate internucleotide linkage (see for example Sheehan et al., 2003, Nucleic Acids Research, 31, 4109-4118). The backbone-modifications can be within the sense strand, antisense strand, or both the sense and antisense strands. In some embodiments, only a portion of the internucleotide linkages are modified in one or both strands. In other embodiments, all of the internucleotide linkages are modified in one or both strands. In one embodiment, the modified internucleotide linkages are at the 3' and 5' ends of one or both strands.

In some embodiments, the nucleic acid may comprise one or more (e.g., about 1, 2, 3, 4, 5, 6, 7, 8, 9, 10, or more) crosslinks, e.g., a crosslink wherein the sense strand is crosslinked to the antisense strand of the siRNA duplex. Crosslinkers are commonly known in the art, and include psoralen, mitomycin C, cisplatin, chloroethylnitrosoureas and the like. In one embodiment, the crosslink of the invention is a psoralen crosslink. Preferably, the crosslink is present downstream of the cleavage site referencing the antisense strand, and more preferably, the crosslink is present at the 5' end of the sense strand.

In some embodiments, the nucleic acid comprises a nucleotide sequence wherein the antisense strand and target mRNA sequences comprise one or more (e.g., about 1, 2, 3, 4, 5, 6, 7, 8, 9, 10, or more) mismatches. In some embodiments, the mismatch is downstream of the cleavage site referencing the antisense strand, e.g., within 1-6 nucleotides from the 3' end of the antisense strand. In another embodiment, the nucleic acid molecule, e.g., RNA silencing agent, of the invention is an siRNA molecule that comprises a bulge, e.g., one or more (e.g., about 1, 2, 3, 4, 5, 6, 7, 8, 9, 10, or more) unpaired bases in the duplex siRNA. In some embodiments, the bulge is in the sense strand.

It is to be understood that any of the above combinations can be used in any combination to provide the modified nucleic acid.

Nucleic acids may be modified according to methods described in the art (Amarzguioui et. al., Nuc. Acids. Res., (2003) 31: 589-95; Chiu and Rana, RNA, (2003), 9: 1034-48; Chiu and Rana, Mol. Cell., (2002), 10: 549-61); Morrissey et al., Nat. Biotech., (2005), 23: 2002-7), each of which is incorporated by reference herein. In one embodiment, the nucleic acid is conjugated a lipophilic moiety. In one embodiment, the lipophilic moiety is a ligand that includes a cationic group. In another embodiment, the lipophilic moiety is attached to one or both strands of an siRNA. In a preferred embodiment, the lipophilic moiety is attached to one end of the sense strand of the siRNA. In another preferred embodiment, the lipophilic moiety is attached to the 3' end of the sense strand. In certain embodiments, the lipophilic moeity is selected from the group consisting of cholesterol, vitamin E, vitamin K, vitamin A, folic acid, or a cationic dye (e.g., Cy3). In a preferred embodiment, the lipophilic moiety is a cholesterol. Other lipophilic moieties include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine. In some embodiments, the nucleic acid may also contain a nuclear localization/nuclear targeting signal(s). Such modifications may be made exclusive of, or in addition to, any combination of other modifications as described herein. Nuclear targeting signals include any art-recognized signal capable of effecting a nuclear localization to a molecule, including, for example, NLS signal sequence peptides.

The nucleic acids described herein may be produced enzymatically or by partial/total organic synthesis. In one embodiment, the nucleic acid is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., RNA silencing oligonucleotides, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

In some embodiments, the nucleic acid molecule is an antisense nucleic acid molecule that is complementary to a target mRNA or to a portion of the mRNA, or a recombinant expression vector encoding said antisense nucleic acid molecule. Antisense nucleic acid molecules are generally single-stranded DNA, RNA, or DNA/RNA molecules which may comprise one or more nucleotide analogs. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986). An antisense nucleic acid molecule comprises a nucleotide sequence that is complementary to the target mRNA sequence and accordingly is capable of hydrogen bonding to the mRNA. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Preferably, an antisense nucleic acid is designed so as to be complementary to a region preceding or spanning the initiation codon in the 3' untranslated region of an mRNA.

Given the known nucleotide sequence of a target mRNA, antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA. For example, the antisense oligonucleotide can be complementary to the region surrounding the translation start site of a target mRNA. An antisense oligonucleotide can be, for example, about 5, 10, 15, 20, 25, 30, 35, 40, 45, 50, 60, 70, 80, 100, 500, 1000 nucleotides or more in length. In some embodiments, the antisense oligonucleotide may be as long as, or longer than, the length of the mRNA that is targeted.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

In yet another embodiment, a nucleic acid molecule is an α-anomeric nucleic acid molecule. An α-anomeric nucleic acid molecule forms specific double-stranded hybrids with complementary RNA in which, contrary to the usual 1-units, the strands run parallel to each other (Gaultier et al. (1987) Nucleic Acids. Res. 15:6625-6641). Such a nucleic acid molecule can also comprise a 2'-O-methylribonucleotide (Inoue et al. (1987) Nucleic Acids Res. 15:6131-6148) or a chimeric RNA-DNA analogue (Inoue et al. (1987) FEBS Lett. 215:327-330).

In still another embodiment, the nucleic acid molecule is a ribozyme. Ribozymes are catalytic RNA molecules having extensive secondary structure and which intrinsically capable of cleaving a single-stranded nucleic acid, such as an mRNA, to which they have a complementary region.

Alternatively, gene expression can be inhibited by targeting nucleotide sequences complementary to the regulatory region of a target gene to form triple helical structures that prevent transcription of a gene in target cells. See generally, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15.

In some embodiments, the nucleic acid is an antagomiR or an RNA sponge. Antagomirs are chemically modified oligonucleotides that bind specifically to and silence particular microRNAs. An RNA sponge is a small synthetic RNA that bind to multiple microRNAs that have the same sequence in their "seed region."

Methods of Use

The nanoparticle described herein is useful for, e.g., delivering a nucleic acid to a myeloid cell or a cell that expresses IL4Rα. For example, described herein is a method of delivering a nucleic acid to a cell that expresses IL4Rα comprising contacting the cell with a nanoparticle described herein. In various embodiments, the nucleic acid is any nucleic acid that is described herein.

Also provided are methods of screening for nucleic acids that modulate the suppressive activity of a tumor educated myeloid cell comprising (a) contacting the cell with a nanoparticle comprising (i) a charged polymeric dendrimer conjugated to a peptide that specifically binds to IL4Rα expressed on a tumor educated myeloid cell, and (ii) one or more candidate nucleic acids; and (b) determining whether the suppressive activity of the cell is modulated. The suppressive activity of the cell can be determined, for example, using the assay described in Example 6.

As used herein the term "candidate nucleic acid" refers to any molecule that is contemplated as being useful for modulating the suppressive activity of a myeloid cell. One or more candidate nucleic acids can be simultaneously screened.

In some embodiments, the one or more candidate nucleic acids are screened in one or more in vitro cells. In another embodiment, the one or more candidate nucleic acids is screened in one or more subjects. In yet another embodiment, the one or more candidate nucleic acids is screened in one or more in vitro cells followed by screening in one or more subjects, e.g., for the purpose of validation studies of the nucleic acid(s)

Also provided is a method of suppressing the activity of a myeloid cell. In one aspect, the method comprises contacting the cell with a composition comprising a nanoparticle described herein comprising one or more nucleic acids in an amount effective to modulate the suppressive activity of the cell. The suppressive activity of the cell can be determined, for example, using the assay described in Example 6. Also provided is a method of decreasing proliferation of a cancer cell comprising contacting the cell with a composition comprising a nanoparticle described herein comprising one or more nucleic acids in an amount effective to decrease proliferation of the cancer cell. Examples of nucleic acids suitable for use in the methods are described above and in the Examples.

The contacting step of the methods described herein can occur in vitro or in vivo. When the contacting step occurs in vivo, the composition further comprises an amphipathic molecule. An "amphipatic molecule" as used herein refers to a molecule that has a hydrophilic and a hydrophobic group. The hydrophobic group is usually a chain of the form $R=CH_3(CH_2)_n$, with n>3. The hydrophilic group is usually a charged group such as CO2-, SO4-, SO3-, PO3- or polar groups. The two portions are covalently linked to give RCO2-, RSO4-, RSO3-, RPO3-. Exemplary amphipathic molecules include, but are not limited to, cardiolipin, lipids, phospholipids, glycolipids, sphingolipids, lipopeptides, Pepducins (Covic et al *Proc. Natl. Acad. Sci. U.S.A.* 99 (2): 643-8) Cholesterol, detergents (i.e. Sodium Dodecylsulfate) and soaps.

The nanoparticles described herein may be used in research to further investigate the role of tumor educated myeloid cells in cancer.

Pharmaceutical Formulations

Where clinical applications are contemplated, the nanoparticles are prepared as part of a pharmaceutical composition in a form appropriate for the intended application. Generally, this entails preparing compositions that are essentially free of pyrogens, as well as other impurities that could be harmful to humans or animals. However, in various embodiments, a straight dendrimer formulation may be administered using one or more of the routes described herein.

In some embodiments, the nanoparticles described herein are used in conjunction with appropriate salts and buffers to render delivery of the compositions in a stable manner to allow for uptake by target cells. Buffers also are employed when the dendrimer conjugates are introduced into a subject. Aqueous compositions comprise an effective amount of the dendrimer conjugates to cells dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

The active dendrimer conjugates may be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Combinations

In some embodiments, the compositions (or methods described herein) further comprise an agent that that inhibits the immunosuppressive activity of MDSCs. In some embodiments, the agent that inhibits the immunosuppressive activity of MDSCs deactivates MDSCs, promotes differentiation of MDSCs into mature cells, inhibits myeloid cell development into MDSCs or depletes MDSCs. An agent that deactivates MDSCs includes, but is not limited to, nitric oxide inhibitors (e.g., nitric oxide inhibitors; and L-NAME), phosphodiesterase-5 (PDE-5) inhibitors such as sildenafil and tadalafil; arginase inhibitors (e.g., PDE-5 inhibitors, COX2 inhibitors, NOHA and L-NAME), ROS inhibitors (e.g., synthetic triterpenoids), MDSC migration inhibitors (e.g., anti-glycan antibodies and CSF-1 inhibitors), histamine inhibitors and anti-IL-17 antibodies. An agent that promotes differentiation of MDSCs into mature cells includes, but is not limited to, vitamins (e.g., all trans retinoic acid, vitamin A and vitamin D3), cytokines (e.g., IL-12) and CpG. An agent that inhibits development of MDSCs include, but is not limited to, bisphosphonates (e.g., N-bisphosphonates such as zoledronic acid) and modulators of cell signaling (e.g., JAK2/STAT3 inhibitors, multi-kinase inhibitors and VEGF inhibitors). An agent that depletes MDSCs includes, but is not limited to, a cytotoxic agent (e.g., gemcitabine, cisplatin, paclitaxel and 5-fluorouracil), HSP90 inhibitors (e.g., 17-DMAG), IL-6R and antibody drug conjugates.

The compositions described herein can comprise more than one (same or different) nanoparticle described herein and/or additional pharmaceutical agents depending on the purpose of the pharmaceutical composition. The pharmaceutical composition can, for example, comprise one or more anti-cancer therapeutic agents, including, but not limited to ionizing radiation, an alkylating agent, anthracycline, cytoskeleton disruptor, epothilone, inhibitor of topoisomerase II, nucleotide analog or precursor analog, peptide antibiotic, platinum based agent, retinoid, vinca alkaloid or a derivative thereof. In one embodiment, the anti-cancer therapeutic agent is one of: all-trans retinoic acid, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, Pemetrexed, Teniposide, Tioguanine, Valrubicin, Vinblastine, Vincristine, Vindesine, and Vinorelbine.

Kits

Also contemplated are kits for practicing the methods described herein. For example, in some embodiments, described herein is a kit comprising a vial containing a composition comprising nanoparticle comprising a dendrimer conjugated to a IL4Rα binding peptide described herein, and a set of user instructions. The kit can comprise more than one (same or different) nanoparticles and/or additional components. The kit can optionally comprise appropriate solutions (e.g., buffers, reagents) and/or containers (e.g., vials, multi-well plates, tubes, etc.).

The following examples are provided to illustrate certain particular features and/or embodiments. These examples should not be construed to limit the invention to the particular features or embodiments described.

EXAMPLES

Example 1—Design and Synthesis of 4PD

Starting with the mouse IL4 sequence residues 78-89 of SEQ ID NO: 2 (78-LQRLFRAFRCLD-89), the Cys was deleted and replaced with the synthetic amino acid "Abu" in order to 1) better mimic human IL4 and 2) to facilitate the later conjugation with the PAMAM dendrimer.

To facilitate penetrance of the peptide into the IL4Rα pocket, the hydrophobic spacer aminohexanoic acid (Ahx) followed by a cysteine (C) for the subsequent attachment of the peptide to the dendrimer was added. Finally, to neutralize the positive and negative charges at the amino- and carboxy-terminii, the termini were modified by N-terminal acetylation and C-terminal amidation. The resulting (acetyl)-LQRLFRAFR[Abu]LD[Ahx]C(amide) peptide (SEQ ID NO: 1) was conjugated to G5 PAMAM dendrimer by maleidoamide chemistry. Briefly (as illustrated in FIG. 2B), G5 PAMAM dendrimers were reacted with eight excess of m-maleimidobenzoyl-N-hydoxysuccinimide ester to generate NHS-maleimide dendrimers. The activated dendrimers were reacted with four excess of the targeting peptide to generate the 4PD. It is important to note that, in this case the maleidoamide ester-Cysteine ester serves also as additional spacer between the dendrimer surface and the targeting peptide. The reaction product was purified by HPLC to remove unreacted reagents.

Example 2—Characterization of 4PD and 4PD/shRNA Complexes

Mass spectrometry (MS) was performed to characterize the generated nanoparticles. As shown in FIG. 3A, the MS analysis revealed the presence of dendrimers with 1, 2 or 3 IL4Rα binding peptides and the absence of unconjugated dendrimer or free IL4Rα peptide. The molecular weight of the complex was estimated to be 33,560 Daltons. Considering that the molecular weight of the G5 PAMAM dendrimer and that of the targeting peptide are 28,826 Daltons and 1831.2 Daltons, respectively, this analysis indicates that an average of 2.58 peptides [(33560-28826 Daltons)/1831.2 Daltons] are conjugated to each dendrimer.

Next, the size of dendrimer/shRNA complexes was determined. As shown in FIG. 3B, 4PD was complexed with a scramble of 43 different shRNA nucleic acids. Briefly, shRNA (1 ug) was admixed dropwise to the 4PD in water (N:P ratio=10:1) while vortexing at RT. The mixture was incubated for five minutes and 0.2 ug of cardiolipin was added to neutralize residual charges on the dendrimers and to provide a hydrophobic shield to the resulting complex. One minute after the cardiolipin was added, 1/9 volumes of 10× concentrated HEPES or NaCl was added. The mixture was then evaluated by dynamic light scattering. Results indicated the presence of homogeneous complexation and that the size of the complexes are dependent on the type of buffer and on the presence of cardiolipin and ranging from 50 nm in eater without cardiolipin to 350 nm in NaCl (0.9%) with cardiolipin. Considering that the size of a dendrimer is approximately 5 nm, this analysis revealed that each complex is formed by multiple dendrimers and multiple shRNAs. The size of the complexes is appropriate to take advantage of the enhanced permeability retention (EPR) effect.

Example 3—Conjugation of the Peptide to the G5 PAMAM Dendrimers Increased its Avidity to the IL4Rα

Next, the ability of the IL4Rα binding peptide or the 4PD to bind to the IL4Rα was evaluated. Epoxybeads were conjugated with recombinant IL4Rα and used as binding target of 4PD or of the targeting peptide. Briefly, the recombinant chimeric IL4Rα protein composed by the mouse IL4Rα (Ile26 Arg233) and the human IgG1 (Pro100 Lys330) linked by the IEGRMD spacer polypeptide and generated in the NSO myeloma cell line was purchased by R&D systems (Minneapolis, Minn., USA). The protein was treated for 24 hours with 1.5% w/w factor Xa (SIGMA. St. Louis, Mo., USA) in tris-HCl (20 mM) and NaCl (200 mM) to cleave the IL4Rα extracellular domain. Factor Xa was removed by the solution using the Factor Xa removal resin (QIAGEN, Valencia, Calif., USA) and following the manufacturer instruction. IgG-linker fraction was removed from the solution by using protein-A conjugated magnetic beads (Invitrogen, Carlsbad, Calif., USA). The purity obtained by this procedure assessed by SDS PAGE was higher than 95% with only trace of IgG (data not shown). The obtained IL4Rα fraction was linked to epoxy magnetic beads M-450 by an overnight (ON) incubation at room temperature (RT) of $20 \times 10^6$ beads with 10 µg of protein in a final volume of 1 mL in a sodium phosphate buffer (pH:8.0). The beads were washed 5 times using PBS and resuspended in a final volume of 1 mL of PBS-1% BSA. Similar procedures were performed using recombinant VCAM protein as irrelevant target. Correct conjugation was evaluated via FACs after labeling with an anti-IL4Rα antibody.

Figures 4A, 4B:
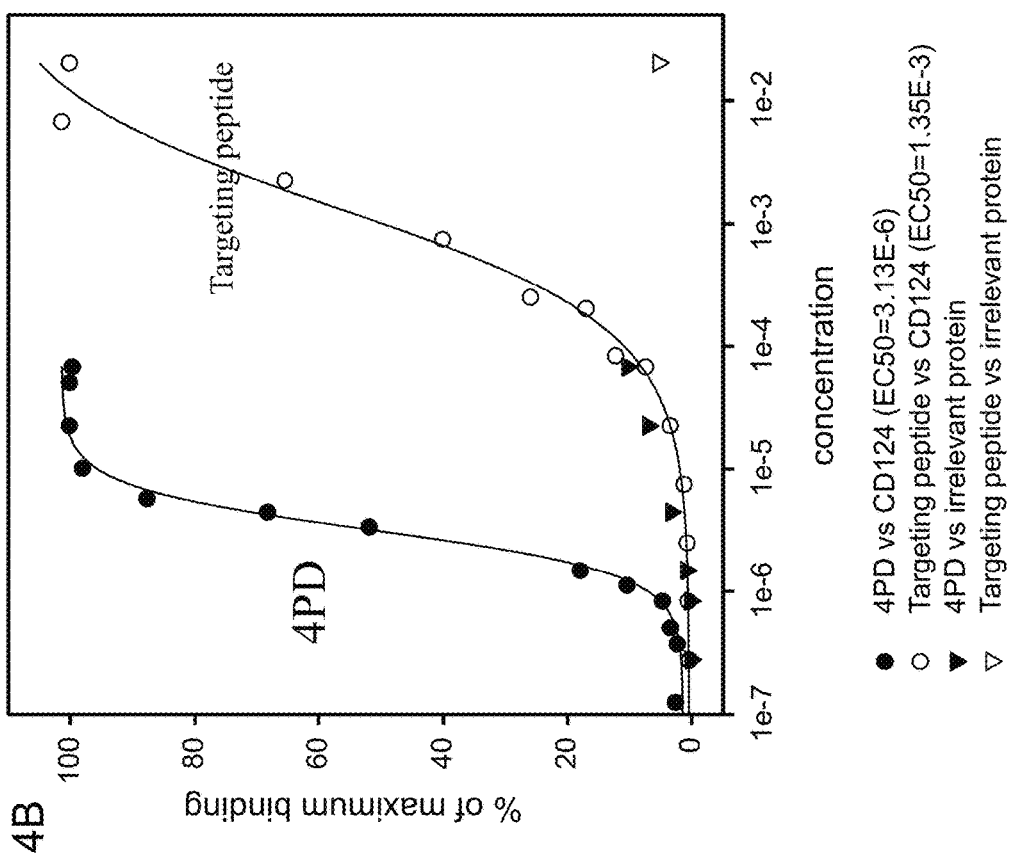
FIGS. 4A and 4B illustrate data establishing that conjugation of the IL4Rα binding peptide to the dendrimer increased the affinity/avidity to the IL4Rα. Briefly, Alexa555-shRNA/4PD complexes or the IL4Rα targeting FITC-peptide as control were incubated for 10' at RT with epoxybeads decorated with recombinant IL4Rα (FIG. 4A). After 2 washes in PBS, binding was evaluated by FACS. The results show that conjugation of the peptide to the dendrimer dramatically increase 4PD affinity (FIG. 4B).

Next, the binding of the 4PD to the IL4Rα was evaluated. 4PD were loaded with Alexa555-conjugated scrambled shRNA and the indicated concentration were incubated for 10 minutes at room temperature with $10^6$ IL4Rα conjugated epoxybeads (filled circle) or with VCAM-conjugated epoxybeads (filled triangle). See FIG. 4A. Similarly, the targeting FITCilated peptide (open symbol) (in which FITC was added instead of the PAMAM dendrimers by maleimide chemistry) was incubated, at the indicated concentration, with either the IL4Rα (open circles) or the VCAM loaded (open triangle) epoxybeads. Beads were washed twice with PBS and the binding evaluated by FACS. As shown in FIG. 4B, binding of the IL4Rα binding peptide to the dendrimer dramatically increased the avidity of the peptide for the IL4Rα, an increase of almost 1000 times its apparent Kd (1.3 mM to 3 µM). These data indicate that not only that the conjugation of the IL4Rα binding peptide to the dendrimer does not affect its capacity to bind to IL4Rα, but instead, the conjugation to dendrimer increased the overall avidity for the relevant target.

Example 4—4PD can Recognize Both Mouse and Human Myeloid-Derived Suppressor Cells (MDSCs)

Figure 5A:
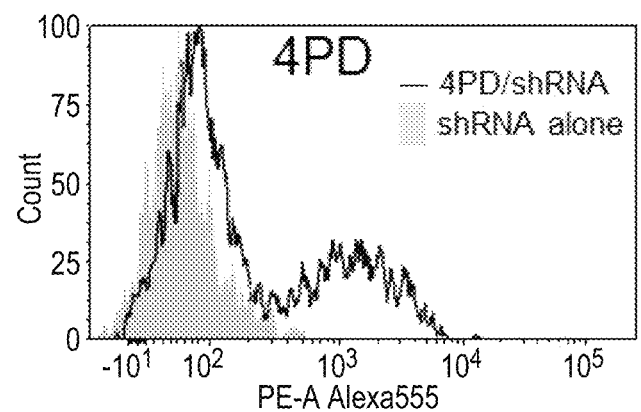
FIGS. 5A-5C demonstrate that 4PD efficiently transfect MDSCs in vitro. MDSC isolated from CT26 tumor bearing mice were transfected with: 1) Alexa555-siRNA alone (gray filled line in FIGS. 5A and 5B), 2) Alexa555-siRNA Dendrimer (black line, bottom panel, FIG. 5B) or 3) Alexa555-siRNA IL4Rα targeting dendrimer (black line, top panel, FIG. 5A). 45 minutes later cells were analyzed by immunefluorescence microscopy (FIG. 5C) and by FACS (FIG. 5B) after gating on the alive (DAPI negative) cells.
Figure 5B:
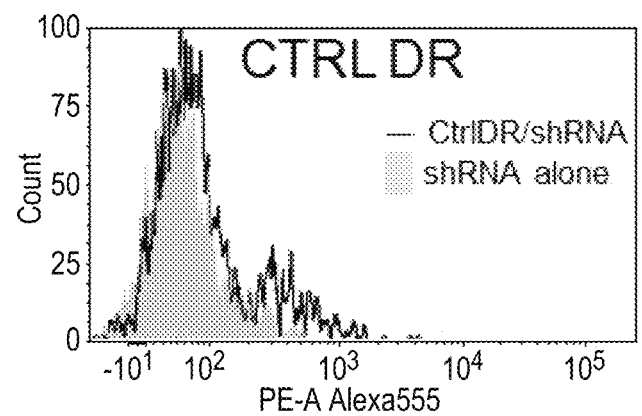
Figure 5C:
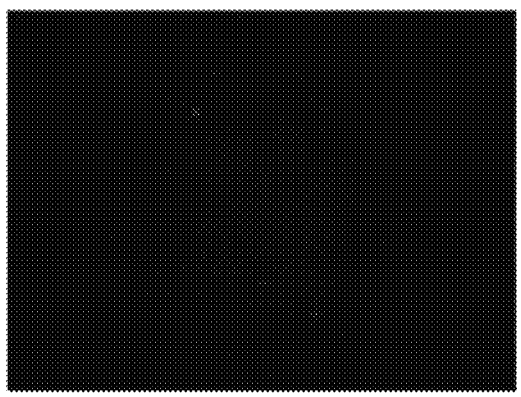
Figure 5C:
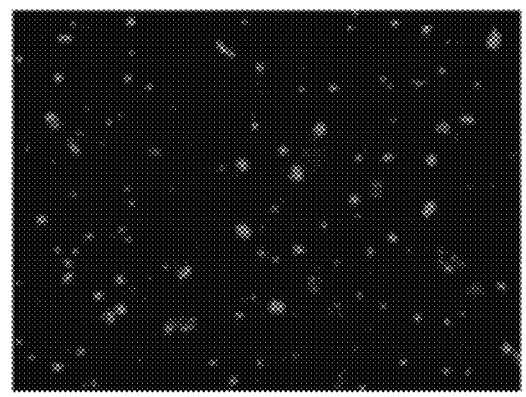
Figure 6A:
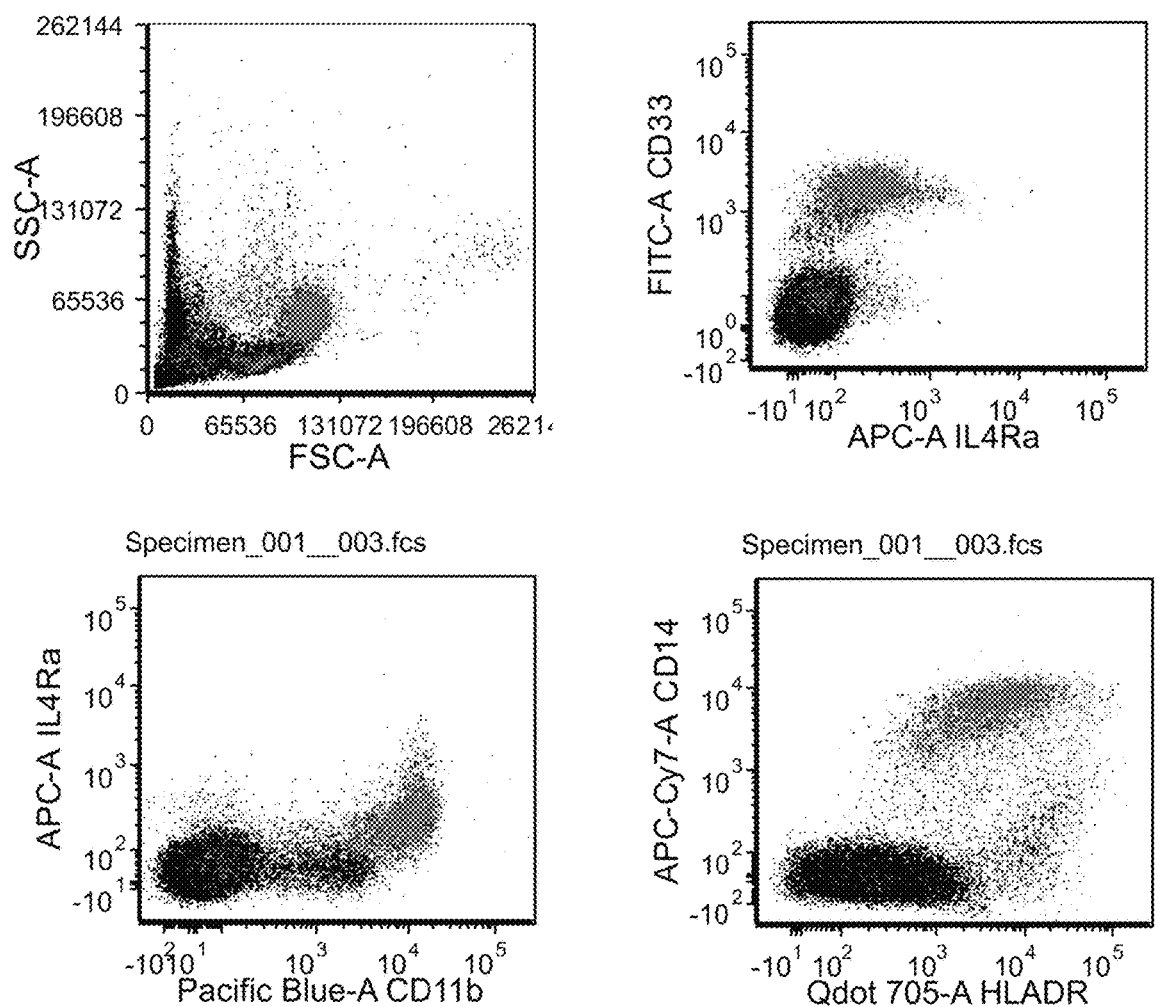
FIGS. 6A-6C demonstrate that 4PD efficiently recognize human MDSCs. PBMCs from patients with HNSCC were incubated (30'at RT) with Alexa555shRNA/4PD complexes, washed and labeled with the indicated antibodies. Transfection was evaluated by FACS.
Figure 6B:
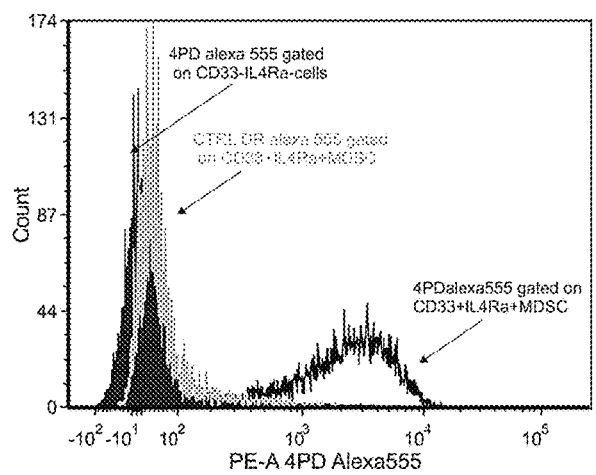

Next, the ability of 4PD to bind to the native IL4Rα receptor expressed on a cell membrane was evaluated. To this aim, the capacity of 4PD to recognize CD11b+myeloid cells isolated from tumor bearing mice was evaluated. See FIG. 5. Briefly, CD11b+MDSC were magnetically isolated from the spleen of Balb/c mice challenged 2 weeks before with the CT26 colon carcinoma. Purified cells were incubated at 37° C. for 15 minutes with Alexa555-shRNA loaded onto 4PD or dendrimers conjugated with scramble peptide as negative control. After the incubation, cells were washed and incubated for an additional 2 hours at 37° C. in CTL media. Cells were harvested and analyzed by FACS (FIG. 5B) or by fluorescence microscopy (FIG. 5C) to determine Alexa-555-shRNA transfection. Both demonstrated that 4PD can promote the internalization of Alexa-555 in the cells. To determine whether 4PD can also recognize human MDSCs, ficolled PBMCs from HNSCC patients were incubated with 4PD loaded with Alexa-555-shRNA for 30 minutes at 4° C. Cells were washed and counterstained with a panel of antibodies able to discriminate human MDSC from the other leukocytes subsets[9]. This analysis (FIG. 6A) showed that 4PD (red dots) binds preferentially to CD11b+ CD14+CD33+IL4Rα+HLADRdim cells that were recently characterized as MDSCs in head and neck squamous cell carcinoma (HNSCC) patients. Similarly (FIG. 6B), Alexa555 fluorescence can be found only on CD33+IL4Rα+ MDSCs (black histogram) but not in other subsets as the IL4Rα-CD33+ myeloid cells (purple) or the non-myeloid (CD33-IL4Rα-) cells.

Figure 6C:
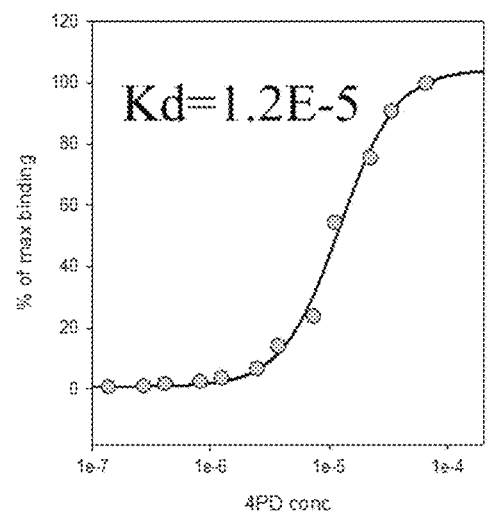

A similar strategy has been used to evaluate the affinity of 4PD for human MDSCs (FIG. 6C). Briefly, a fixed amount of PBMCs from HNSCC patients was stained with different amount of 4PD/Alexa555 complexes and counterstained with the antibody panel described above. Alexa555 MFI within the MDSCs was calculated and used to calculate the apparent affinity indicating a kd of $1.2 \times 10^{-5}$.

Taken together, the data in the present example demonstrates that 4PD can recognize both human and mouse MDSCs. In particular, FIG. 6 shows also an important level of specificity of the platform for human MDSCs despite the presence of other IL4Rα+cells in the PBMCs.

Figure 7B:
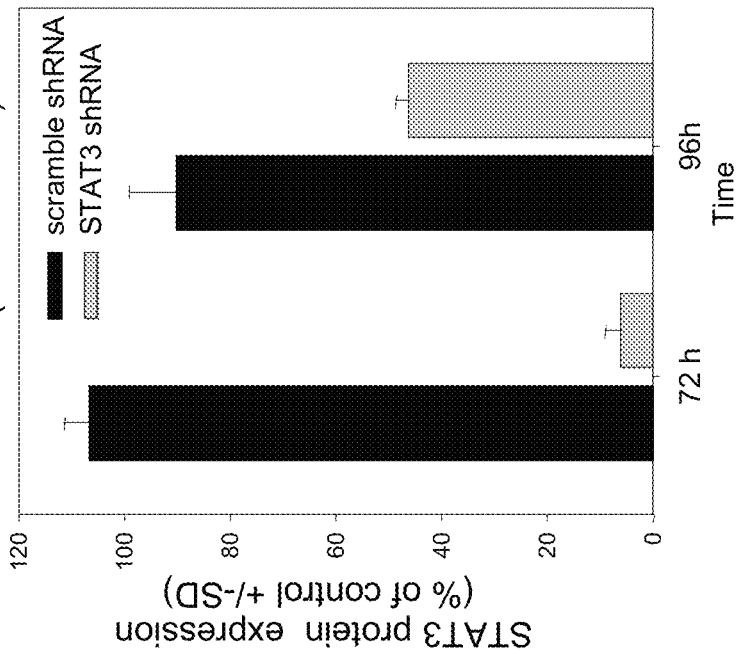
FIGS. 7A-7B demonstrate that 4PD-mediated siRNA silencing in the immortalized MDSC-cell line MSC2.
Figure 7A:
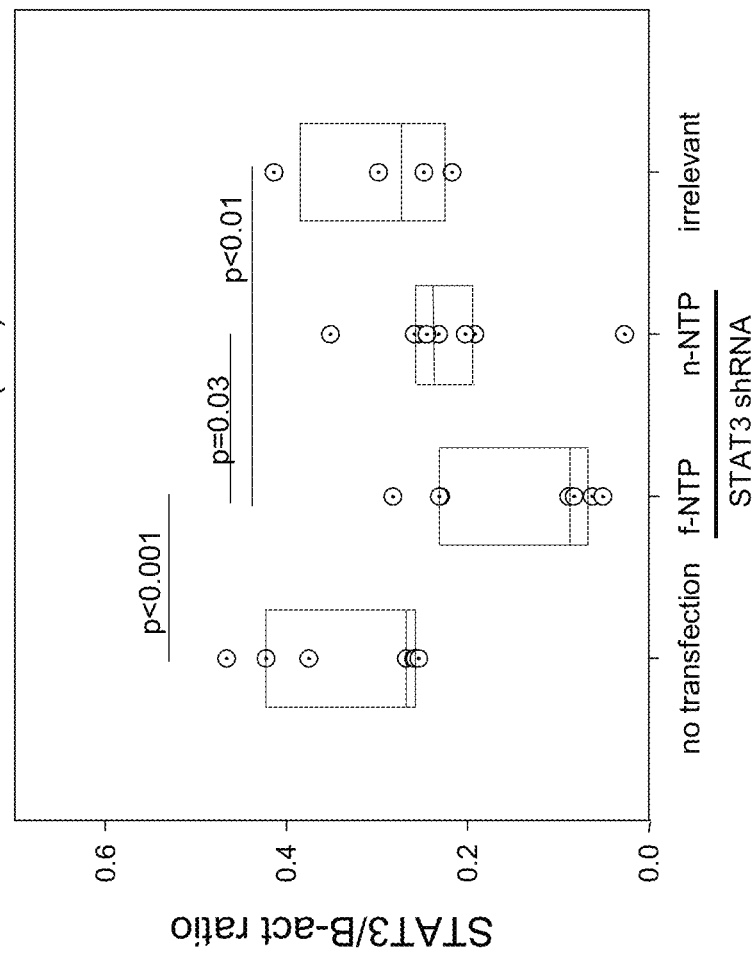

Example 5—4PD can Mediate Cell Transfection with shRNA and Effectively Silence the Target Gene Next, the ability of 4PD to delivered functional shRNA (i.e., able to be released by the 4PD and able to silence the target gene) was evaluated. Briefly, STAT3 specific shRNA (0.5 µg, prepared with normal, nNTP, or fluorinated,fNTP, nucleotide for added stability) was loaded as described in Example 2 onto 4PD (N:P ratio=10:1). See FIG. 7. The resulting 4PD/shRNA complexes were incubated for 30 minutes with the IL4Rα+ immortalized MDSC cell line MSC-2 at 37° C. Cells were then washed twice and plated in CTL media (RPMI-10% FSC) at 37° C. at 5% $CO_2$. Two days later, the cells were harvested, RNA isolated, and RT-PCR was performed using STAT3-specific and beta-actin-specific primers. As shown in FIG. 7A, 4PD mediated transfection of the MSC-2 cells with the shRNA to effectively silence the target gene. No effects were noted when irrelevant shRNA was used. To determine whether not only the RNA but also the protein encoded by the target gene was down-regulated, the experiment was repeated and the expression of the STAT3 expression was evaluated by ELISA 3 and 4 days later (FIG. 7B).

Figure 8:
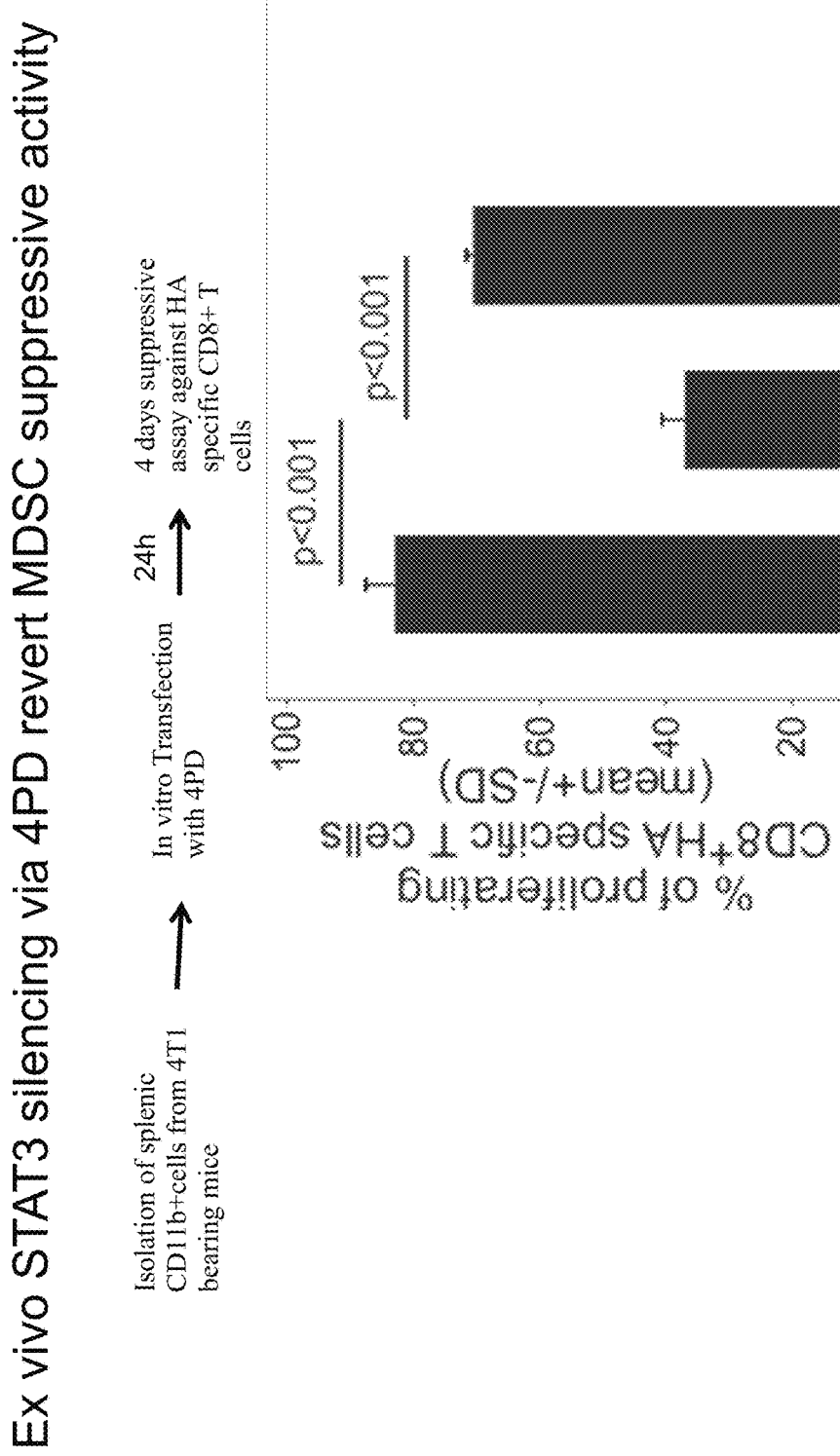
FIG. 8 demonstrates that ex vivo STAT3 silencing via 4PD reduces MDSC suppressive activity. MDSCs from mice bearing the 4T1 mammary carcinoma were transfected with 4PD nanoparticles loaded with STAT3 specific shRNA or irrelevant shRNA. One day later, MDSCs' suppressive activity was evaluated against CFSE labelled CD8+ HA specific T cells stimulated with the relevant peptide. CD8 proliferation was evaluated 4 days later by FACS. Data showed that 4PD mediated STAT3 silencing significantly reduce MDSCs suppressive activity.

Example 6—4PD Mediated Ex Vivo Silencing of STAT3 and Diminished MDSCs Suppressive Activity Next, the ability of 4PD mediated transfection of CD11b+ myeloid cells with STAT3 specific shRNA to diminish the cells suppressive activity was evaluated. Briefly, CD11b+ myeloid cells were magnetically isolated from the spleen of balb/c mice challenged 12 days before with the 4T1 mammary carcinoma. Purified CD11b+ myeloid cells were then transfected with 4PD/STAT3-shRNA complexes for 20 minutes at 37° C. in PBS. As a control, CD11b+ myeloid cells were transfected with scrambled shRNA. Cells were washed and incubated for 24 hours in CTL media at 37° C. at 5% $CO_2$. To evaluate MDSC suppressive function (FIG. 8), $2 \times 10^5$ transfected cells were incubated at 37° C. at 5% $CO_2$ in 96 well plate flat bottom with $10^6$ syngeneic splenocytes as feeder and $10^5$ CFSE labeled CD8+ T cells specific for the influenza-derived Tad restricted epitope hemoagglutin antigen HA. Cognate peptide was added in half of the wells to stimulate T cell proliferation. T cells were incubated without MDSCs for a positive control of proliferation. Four days later proliferation was evaluated via FACS. In the absence of MDSCs, T cells proliferated in response to cognate antigen. When CD11b+MDSCs transfected with scramble shRNA were added to the culture, a reduction of 50% in T cells proliferation was observed indicating that 4PD treatment per se do not alter MDSCs vitality or suppressive activity. Instead, when MDSCs were transfected 4PD comprising the STAT3 shRNA, an important recovery of T cell proliferation was observed. These data indicate that 4PD comprising the STAT3 shRNA mediated STAT3 silencing, thus diminishing the MDSC's suppressive activity.

Example 7—Cardiolipin Reduced Immunogenicity of 4PD

One of the major concerns of transfecting in vivo the myeloid cells is related to their relatively short half-life (5-7 days), and, in tumor host, the rapid hematopoiesis. These two factors together impose the subsequent administration of multiple doses of shRNA carrier that may induce the generation of neutralizing antibodies against the nanoparticle or against the shRNA. Although dendrimers are usually defined as non-immunogenic, the ability of subsequent administration of multiple 4PD/shRNA to generate antibodies against any of the nanoplatform components (dendrimer, peptide, shRNA) was studied. Briefly, naïve Balb/c mice were administered 4PD (14 mg/kg) loaded with shRNA 3 times a week for 15 days (7 doses in total). Importantly, even with this massive administration of 4PD no signs of clinical toxicity were observed. Mice were rested for 14 days to allow the generation of eventual reactive antibodies. At the end of the resting period, plasma was tested for antibodies reactive against the nanoparticle. Briefly, 4PD, 4PD conjugated with the same shRNA, or with Alexa555-shRNA were conjugated to epoxybead as solid support. As additional control, dendrimer conjugated with the PanDr epitope were used. This combination allowed determination of whether antibodies were raised against A) the shRNA (in that case we expected a positivity only against 4PD-shRNA), B) against the 4PD targeting peptide (in this case only the 4PD containing groups but not PPD should be positive), or C) against the dendrimer alone (in this case all the groups should be positive).

To evaluate whether antibodies against the nanoparticle were detectable in the treated animals, plasma was incubated with the different epoxybeads conjugated with the different complexes. Plasma from untreated mice was used as negative control.

Epoxybeads were washed twice with PBS and a FITC-conjugated rabbit anti-mouse Ig antibody was used to detect eventual mouse antibodies bond to the nanoparticles. As shown in FIG. 10A, a discrete signal was detected against all nanoparticle/shRNA complexes when plasma from treated animals was used. On the contrary, only background signal was observed when plasma from untreated mice was tested. These data strongly suggest that multiple administration of 4PD/shRNA complexes can induce the generation of antibodies against the PAMAM dendrimers and thus may limit the multiple use of functionalized dendrimers in vivo.

Figure 9A:
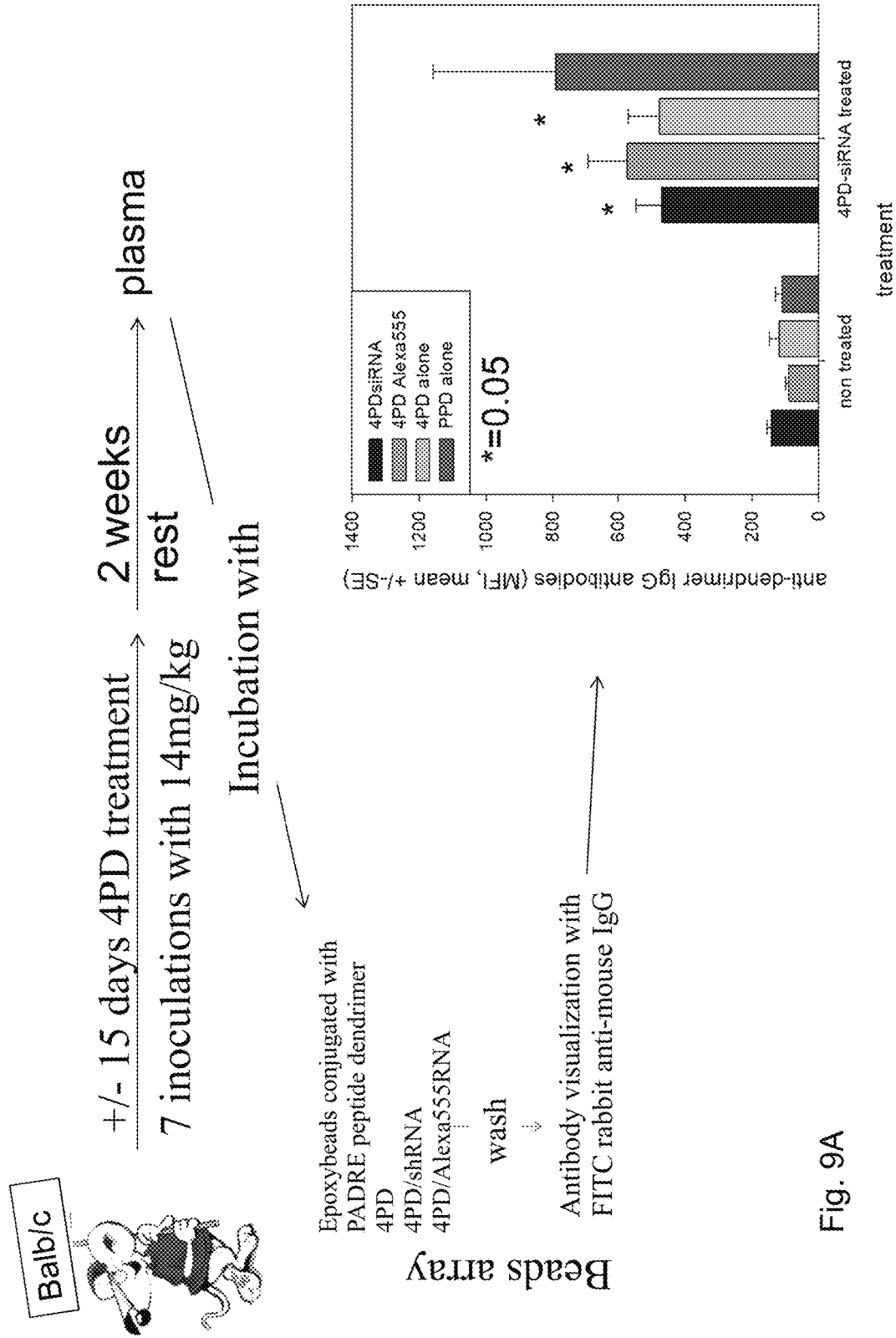
FIGS. 9A and 9B demonstrate that 4PD promote the generation of anti PAMAM dendrimer antibodies.
Figure 9B:
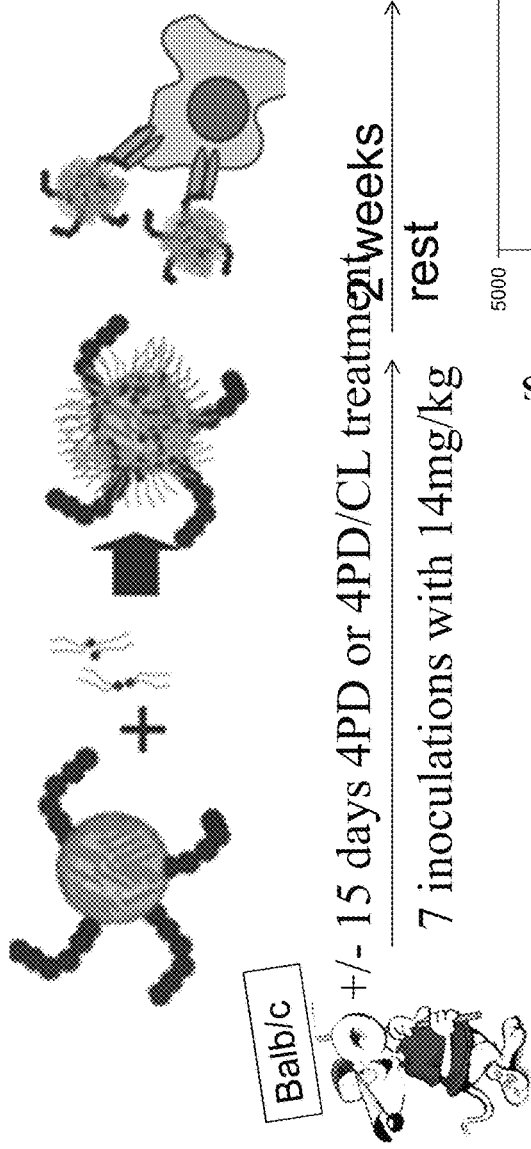
Figure 9B:
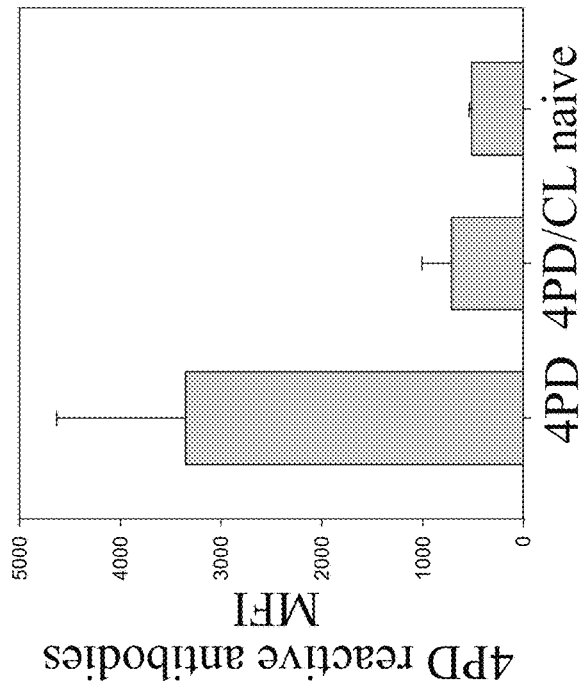

Next, the addition of amphipatic molecules such cardiolipin was evaluated to determine whether it can shield the nanoparticle and thus reduce its immunogenicity. To test this hypothesis (FIG. 9B), the experiment described above was repeated by administering either 4PD/shRNA (14 mg/kg of 4PD, 7 inoculations in 15 days) or 4PD/shRNA/cardiolipin complexes (14 mg/kg of 4PD, 7 inoculations in 15 days). After 2 weeks of rest, plasma from 4PD/shRNA or 4PD/shRNA/cardiolipin treated mice was tested as described above against 4PD/shRNA complexes conjugated to epoxybeads. As in the previous experiment, the administration of 4PD/shRNA complexes resulted in the generation of autoreactive antibodies. Instead, the addition of cardiolipin in the formulation completely abolished the generation of reactive antibodies as demonstrated by a signal similar to the one measured in the plasma of naïve mice.

Taken together, these data demonstrate that the inclusion of an amphipathic molecule virtually eliminates the immunogenicity of the platform and allows for multiple systemic injections.

Example 8—4PD Recognized MDSC and Macrophages In Vivo

Figure 3A:
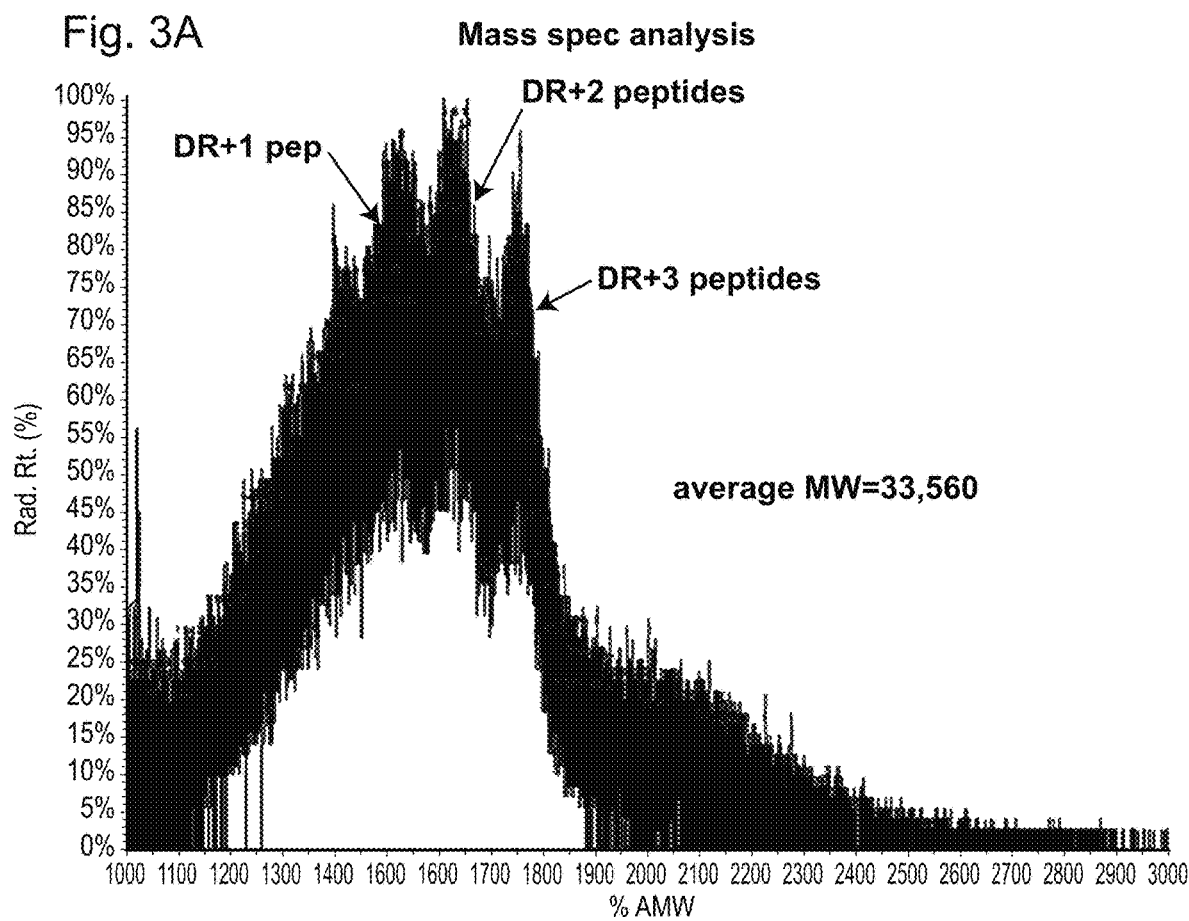
FIGS. 3A and 3B provide a characterization of the 4PD and 4PD-shRNA complexes.
Figure 3B:
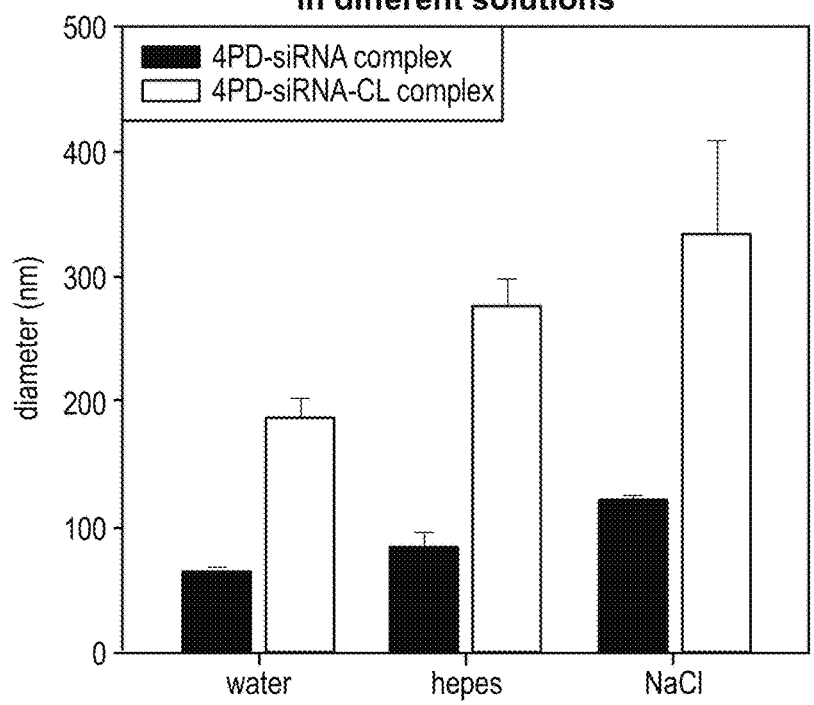
Figure 10:
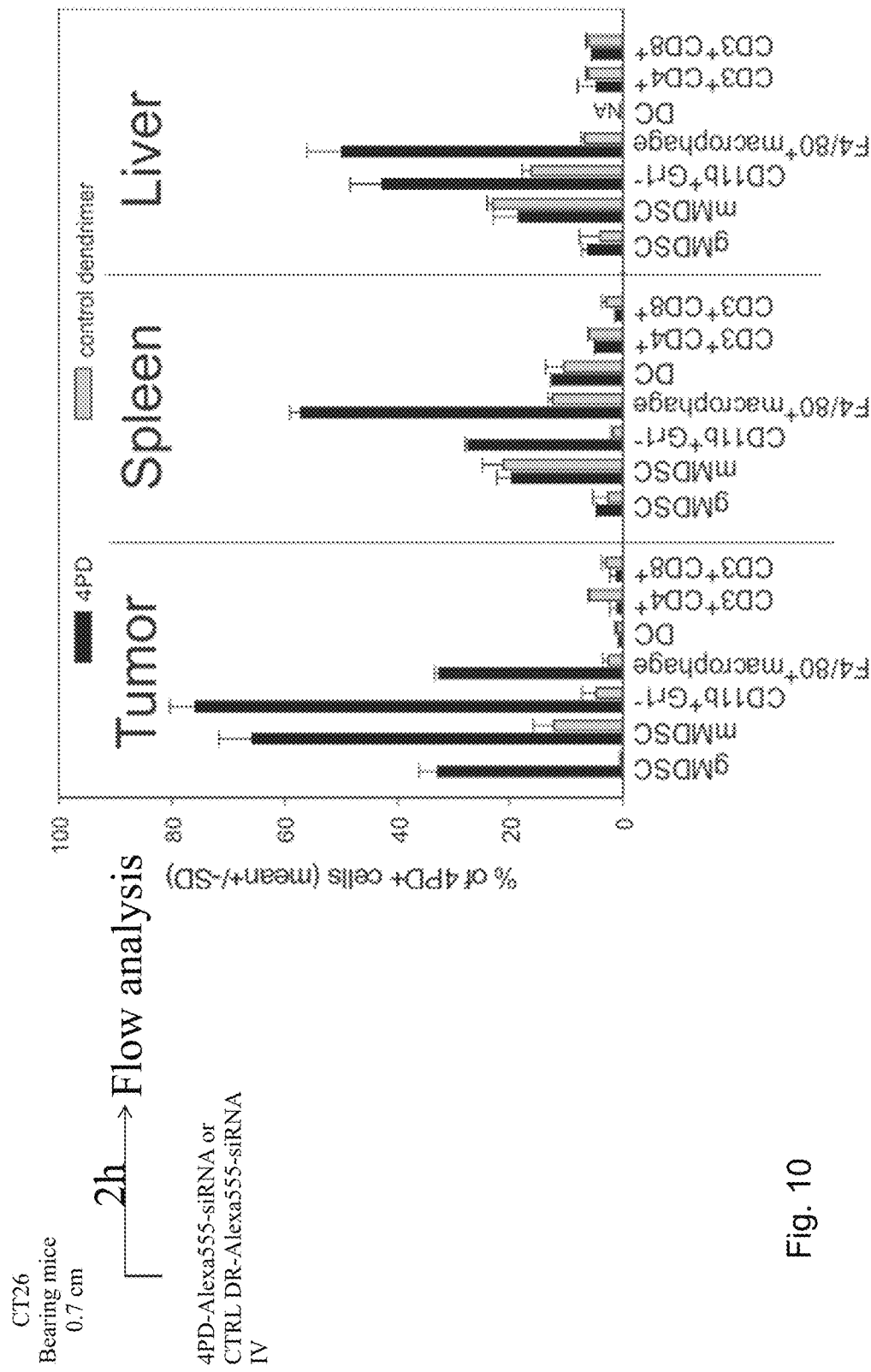
FIG. 10 demonstrates that 4PD recognize preferentially MDSC and macrophage in vivo. Mice bearing the CT26 colon carcinoma (0.7 cm in diameter) were injected with Alexa555-siRNA loaded onto 4PD (black bar) or, as control, onto G5 PAMAM dendrimer functionalized with a random peptide. Two hours later, mice were sacrificed. Single cell suspensions from the spleen, the tumor and the liver were labeled with antibodies specific for Gr1, CD11b, F4/80, CD11c, CD3, CD4, and CD8 to identify granulocytic MDSC (gMDSC), monocytic MDSC (mMDSC), macrophages, dendritic cells, and helper and cytotoxic T cell. Fluorescence in the Alexa555 channel in each population was evaluated by FACSas a read out of 4PD mediated transfection. Data showed that 4PD preferentially transfect CD11b+monocytes, macrophages, and MDSCs.

In order to evaluate 4PD specificity in vivo, Balb/c mice bearing the CT26 colon carcinoma were injected intravenously with 20 ug of Alexa555-shRNA loaded into the 4PD platform with cardiolipin. Alexa 555-shRNA loaded dendrimer coupled with control peptide (a mixture of random peptides) were used as control. Cardiolipin was added to the complexes as described above (FIG. 3). Two hours after 4PD/Alexa555-shRNA systemic injection, mice were sacrificed and single cell suspension from the tumor, the spleen, and the liver was analyzed by multicolor flow cytometry (FIG. 10). In particular, cells were stained with CD11b, Gr1, CD11c and F4/80 specific antibodies to identify granulocytic– (g–) MDSCs (CD11bGr1high), monocytic– (m–) MDSCs (CD11b+GR1–), CD11b+Gr-1 negative myeloid cells, F4/80+macrophages, and CD11chigh DC. Additionally, cells were stained with antibodies specific for CD3, CD8, and CD4 to recognize T cell subsets. As shown in FIG. 10, 4PD (black bar) accumulates mostly in the tumor associated gMDSCs, mMDSC, macrophages and CD11b+Gr1– myeloid cells whereas in the spleen and in the liver it accumulates mostly in F4/80+ tumor educated macrophages, and CD11b+GR1– myeloid cells. Only non-specific level of binding was observed in the non-myeloid leukocytes subsets. RNA loaded into control dendrimer gave significant signal only on the splenic monocytic MDSC.

Taken together, these data indicate that 4PD can transfect preferentially most myeloid cells in the tumor micro-environment and subsets of myeloid cells in the spleen and liver that includes mostly macrophages and CD11b+Gr1– myeloid cells.

Figure 11:
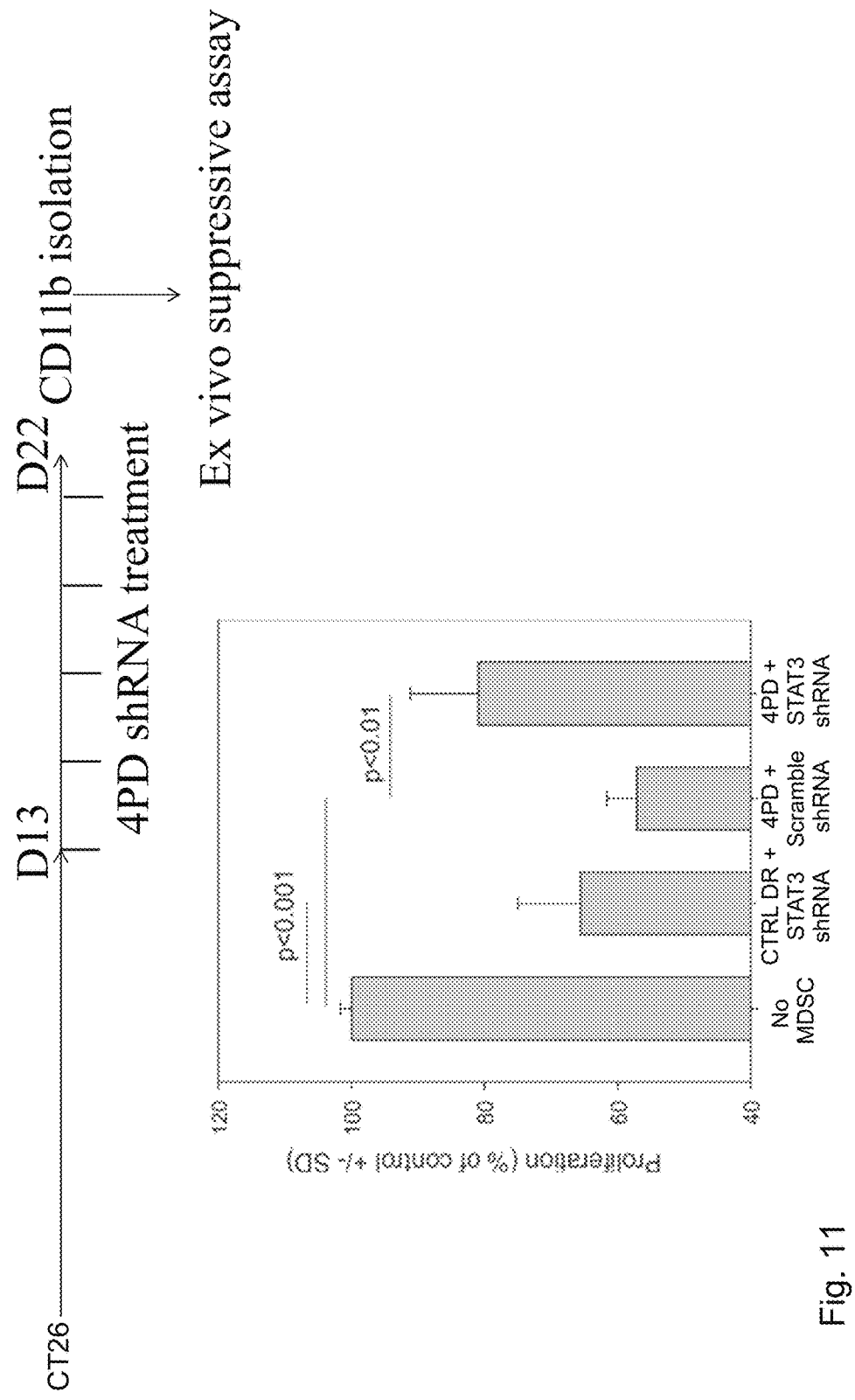
FIG. 11 demonstrates that 4PD-mediated, chronic STAT3 silencing reverses MDSC suppressive activity in vivo. Mice bearing the CT26 colon carcinoma were injected with 4PD loaded with STAT3 or scrambled shRNA, every other day for 9 days. As additional control mice were injected with control dendrimer loaded with STAT3 shRNA. 24 h after the last inoculation, mice were sacrificed and splenic CD11b+ cells magnetically isolated. CD11b+ cells suppressive activity was tested against CFSE labelled HA specific CD8+ T cells stimulated with the relevant peptide. CD8 T cell proliferation was evaluated 3 days later by FACS. Data shows that only 4PD mediated, in vivo STAT3 silencing revert MDSCs suppressive activity.

Example 9-4PD Mediated STAT3 Silencing Reversed MDSCs Suppressive Activity In Vivo Next, the ability of a STAT3-specific shRNA administered in vivo via 4PD to revert MDSCs suppression was evaluated. To this aim, Balb/c mice were challenged subcutaneously with the colon carcinoma CT26. Thirteen days later, when tumor reached approximately 0.7 cm in diameter, mice were intravenously injected with: A) 4PD loaded with STAT3 shRNA, B) 4PD loaded with scrambled shRNA, or C) with control dendrimer loaded with STAT3 specific shRNA. Cardiolipin was added to all complexes to reduce dendrimer immunogenicity. Treatment was repeated on day 15, 17, 19, and 21. On day 22 mice were sacrificed and splenic CD11b+ cells magnetically purified. Suppressive activity of purified cells was tested against CFSE labelled HA specific CD8+ T cells stimulated with the relevant peptide. T cells proliferation was evaluated 3 days later by FACS. As shown in FIG. 11, in the absence of MDSCs T cell proliferate in response to the cognate peptide. When CD11b+ cells isolated from the mice treated with the control dendrimer loaded with STAT3-shRNA or the one isolated from the mice treated with 4PD loaded with scrambled shRNA, a significant suppression of T cell proliferation is observed. On the contrary, when CD11b+ cells isolated from mice treated with 4PD/STAT3-shRNA complexes were used in the assay, T cell proliferation is significantly recovered.

These data indicate that in vivo STAT3-shRNA delivery by 4PD, but not by the control dendrimer, is able to significantly alter MDSCs function.

Figure 12:
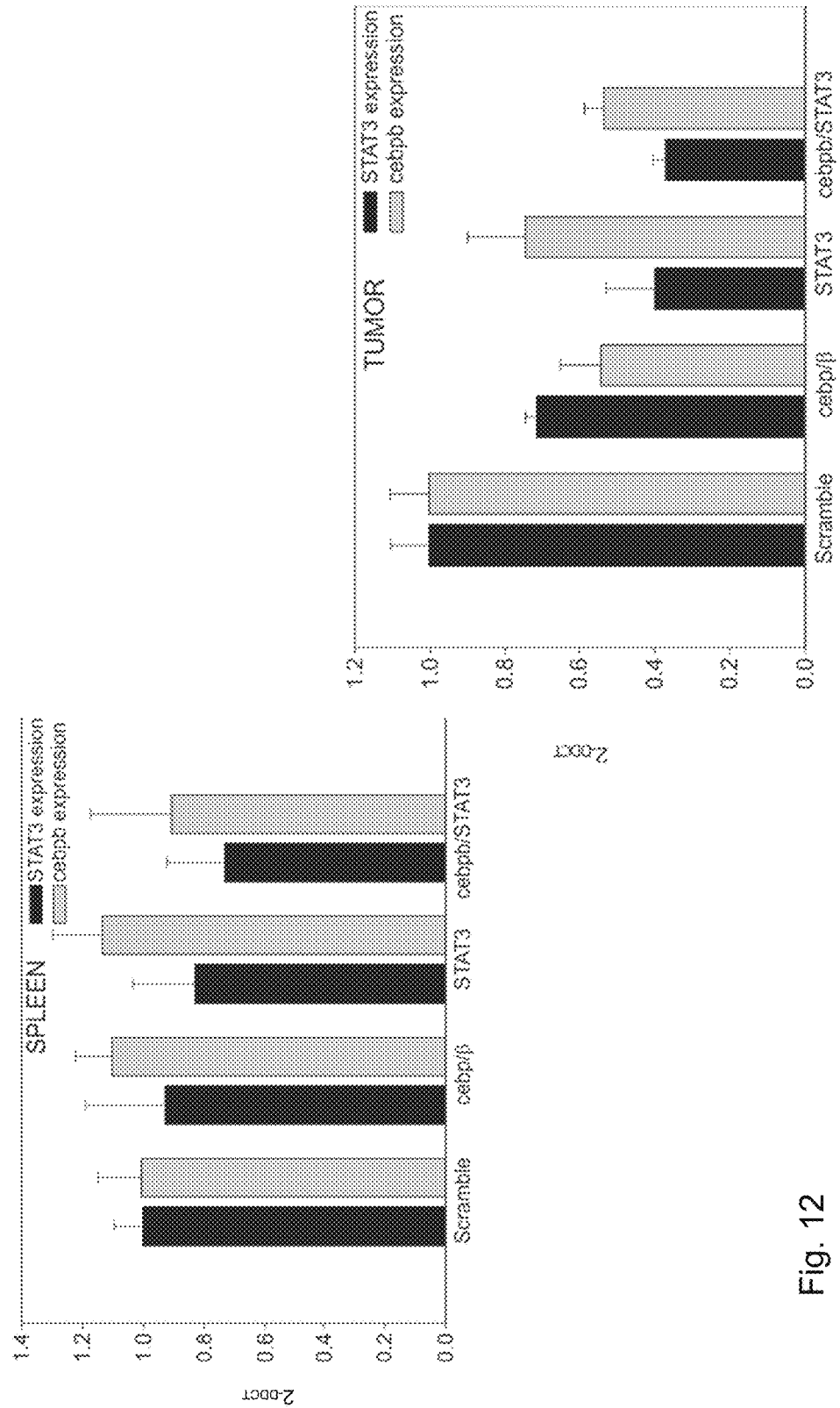
FIG. 12 demonstrates that multiple shRNA can be loaded simultaneously on the 4PD. CT26 bearing (0.5 cm in diameter) mice were treated 3 times a week intravenously with 4PD loaded with cEBPβ specific shRNA, STAT3 specific shRNA, or with both shRNAs. As negative control, mice were treated with 4PD loaded with irrelevant shRNA. Nine days later, mice were sacrificed CD11b+ cells and the expression of STAT3 and CEBPβ was evaluated by RT-PCR. Data showed that 4PD can mediate silencing of both genes indicating that multiple pathways can be silenced simultaneously.

Example 10—Multiple Functions shRNAs can be Delivered Simultaneously Via the 4PD Dendrimer In Vivo Since shRNA is loaded into the 4PD only by electrostatic interaction in a sequence independent manner, it is highly possible that multiple shRNA can be loaded simultaneously in the same 4PD/shRNA complexes. Indeed, considering that the 4PD is approximately 5 nm in diameter, that each shRNA is approximately 5.6 nm long and 2.6 nm wide, and that the size of the complexes is approximately 120 nm, hundreds of shRNA molecules are present in each complex. Thus if a homogeneous mixture of shRNA with different specificity are loaded into the nanoparticles, considering the high numbers of molecules, it is highly probable that each shRNA is equally represented in each complex. If this is the case, also considering that multiple complexes transfect the same cells, simultaneous silencing of different genes using shRNA with different specificity should be possible. To test this hypothesis, a homogeneous mixture of shRNA specific for C-EBPβ and STAT3, two key genes in the biology of myeloid cells in cancer, were loaded into 4PD, covered with cardiolipin and administered to tumor bearing mice. Specifically, 40 ug of A) a mixture of STAT3 and C-EBPβ specific shRNA, B) a mixture of STAT3 specific and scrambled shRNAs, C) a mixture of C-EBPβ specific and scrambled shRNAs, or D) scrambled shRNAs was administered to tumor bearing Balb/c mice on day 9, 11, 13, and 16 after tumor challenge. 48 hours after the last inoculation, mice were euthanized and C-EBPβ and STAT3 expression was evaluated on myeloid cells isolated from the tumor or from the spleen. As shown in FIG. 12, while non-significant changes in gene expression are observed in the splenic CD11b+cells, both STAT3 and C-EBPβ were down-regulated in the CD11b+cells purified from the tumor. In particular, compared to the CD11b+cells from mice treated with the scrambled shRNA, tumoral CD11b+cells isolated from mice treated with shRNA specific for either cebpb or STAT3 showed a significant down-regulation of their target gene. Importantly, these down-regulations are not affected in the group treated with both shRNA indicating that more genes can be simultaneously silenced in vivo using the 4PD platform.

These experiments not only confirm and expand the findings of FIGS. 10 and 11, but also demonstrate that 4PD can effectively and simultaneously deliver shRNA with different specificities to the tumor associated myeloid cells.

Figure 13A:
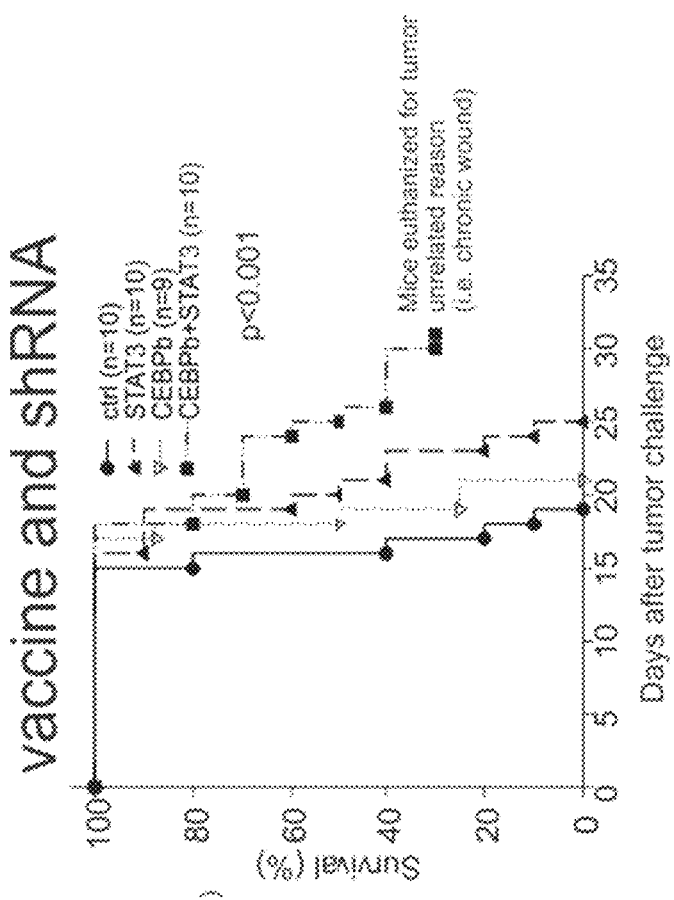
FIGS. 13A and 13B demonstrate that 4PD-mediated STAT3 and C/EBPβ silencing promote tumor regression and mice survival when combined with vaccination. BALB/c mice were injected subcutaneously with $10^5$ CT26 cells on day 0. Starting on day 9, when tumor reached approximately 5 mm of diameter, mice were intravenously treated twice a week with PBS (gray and black line), 4PD loaded with a STAT3 specific (▲) or C/EBPβ specific (open, inverse triangle) shRNA or with both STAT3 and C/EBPβ shRNAs (■ (20 ug/mouse). On day 10 and 17, mice in each group were vaccinated via electroporation with pcDNA3 (FIG. 13A) or with gp70 encoding pcDNA3 (FIG. 13B). Only the contemporary administration of both STAT3 and C/EBPβ shRNA, combined with gp70 vaccination, is able to induce a significant delay in the tumor growth and improve mice survival.
Figure 13B:
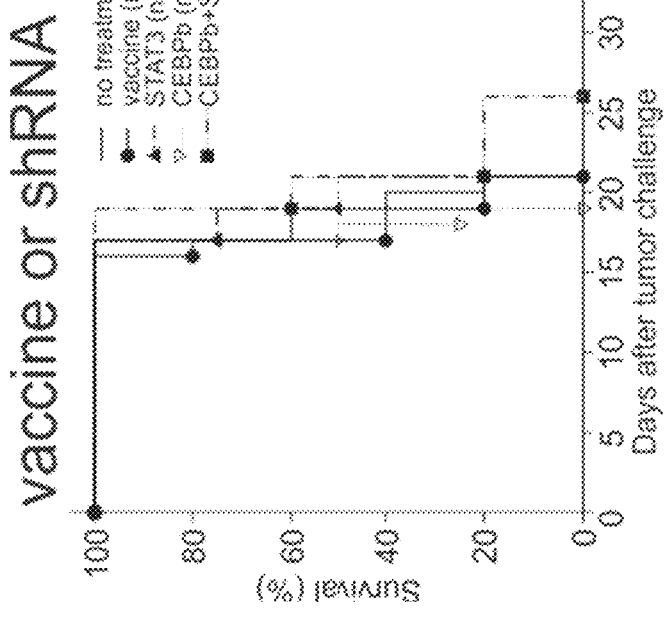
Figure 14A:
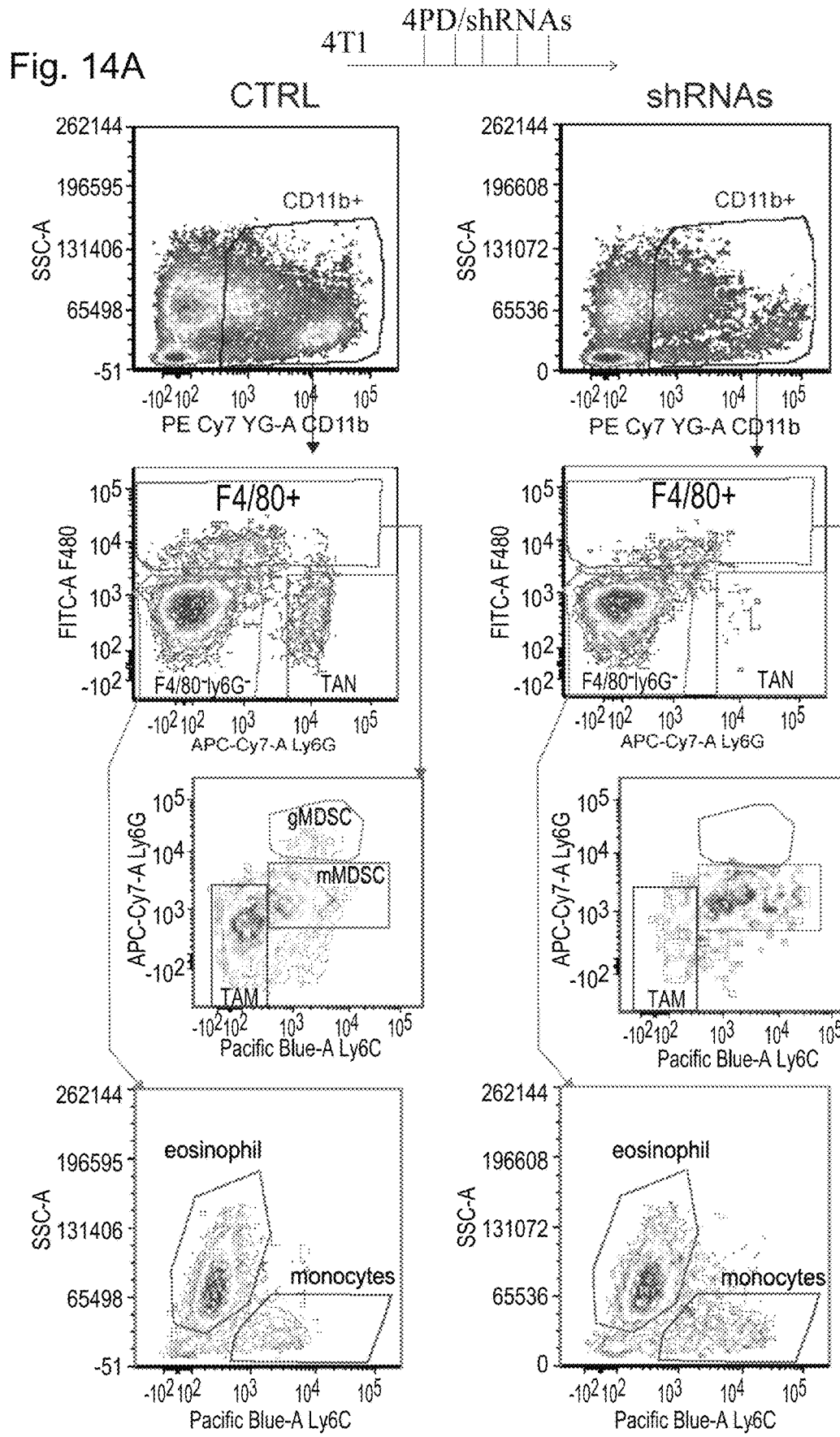
FIGS. 14A-14B demonstrate that 4PD-mediated silencing of CCR-1, -2, -5, and -7 alters leukocytes composition in the tumor micro and macro-environment in vivo. Balb/c mice were injected in the mammary gland with $5 \times 10^6$ 4 T1 cells on day 0. On day 3, 5, 7, 10, and 12, mice were treated intravenously with either a mixture of shRNA specific for CCR-1, -2. -5, and -7 (30 pmoles/g each) or scrambled shRNA. Mice were sacrificed on day 13 and single cell suspension from the spleen and the tumor was analyzed by FACS after labeling with a vital dye and antibodies specific for CD11b, F4/80, Ly6G, Ly6C, and IL4Rα.
Figure 14B:
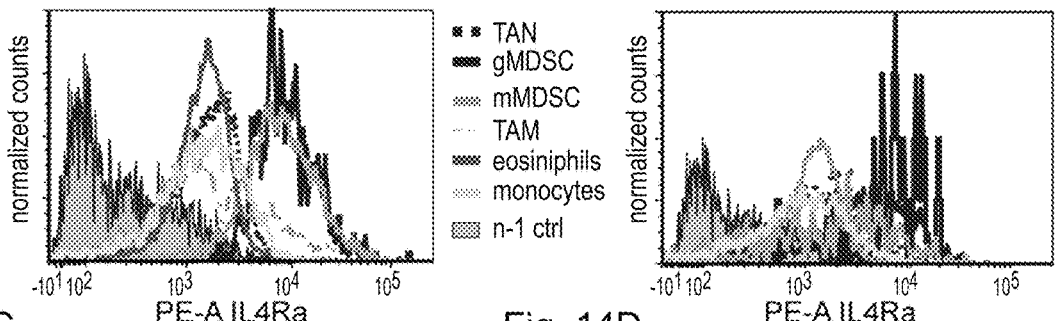
Figure 14C:
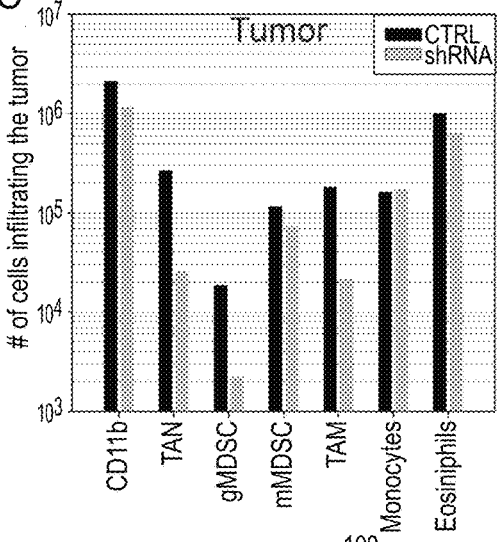
FIG. 14C provides the number of cells for each myeloid subsets infiltrating the tumor.
Figure 14D:
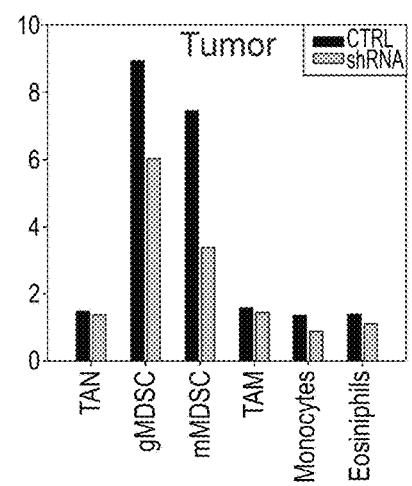
FIG. 14D provides the IL4Rα MFI for the indicated myeloid subset.
Figure 14E:
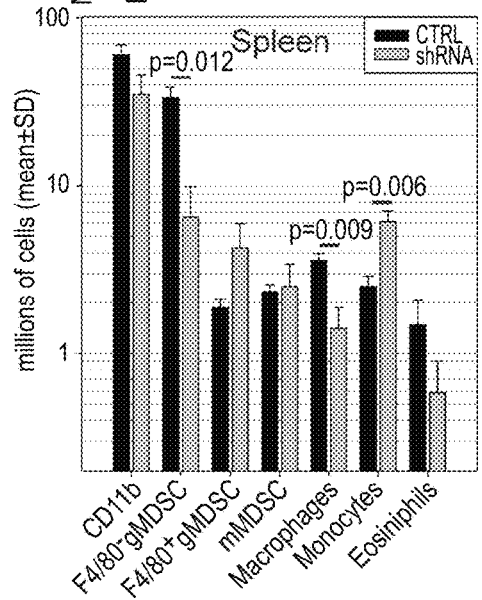
FIG. 14E provides the number of each myeloid subsets in the spleen gated as in FIG. 14A.

Because of the role of both Cebpb and STAT3 in myeloid cells, we wanted to evaluate whether the administration of specific shRNA can not only down-regulate these genes but also provide a therapeutic advantage. To this aim, Balb/c were challenged with the CT26 subcutaneously on day 0. Starting on day 9, mice were treated 3 times a week with 4PD loaded with shRNAs against STAT3, C-EBPβ, or both genes. Mice treated with scrambled shRNA were used as additional control. In each group, part of the mice was vaccinated on day 10 and 17 via DNA electroporation against the tumor associated antigen gp70. Tumor growth was monitored and relative Kaplan Meyer curve are reported in FIG. 13. No therapeutic advantage was visible when vaccination or shRNA treatments were given as monotherapy. When vaccination was coupled with either STAT3 or C-EBPβ silencing a small therapeutic advantage was detectable. However, when vaccination was coupled with the simultaneous silencing of both STAT3 and C-EBPβ shRNA, an important synergistic effect was detectable with 30% of the mice that completely reject the tumor.

Taken together, these experiments demonstrate that multiple shRNA with various specificity can be simultaneous loaded into the 4PD, and this approach can be used to identify synergistic treatment for the treatment of cancer.

Example 11—4PD can be Used to Study Complicated Pathways In Vivo

Figure 15A:
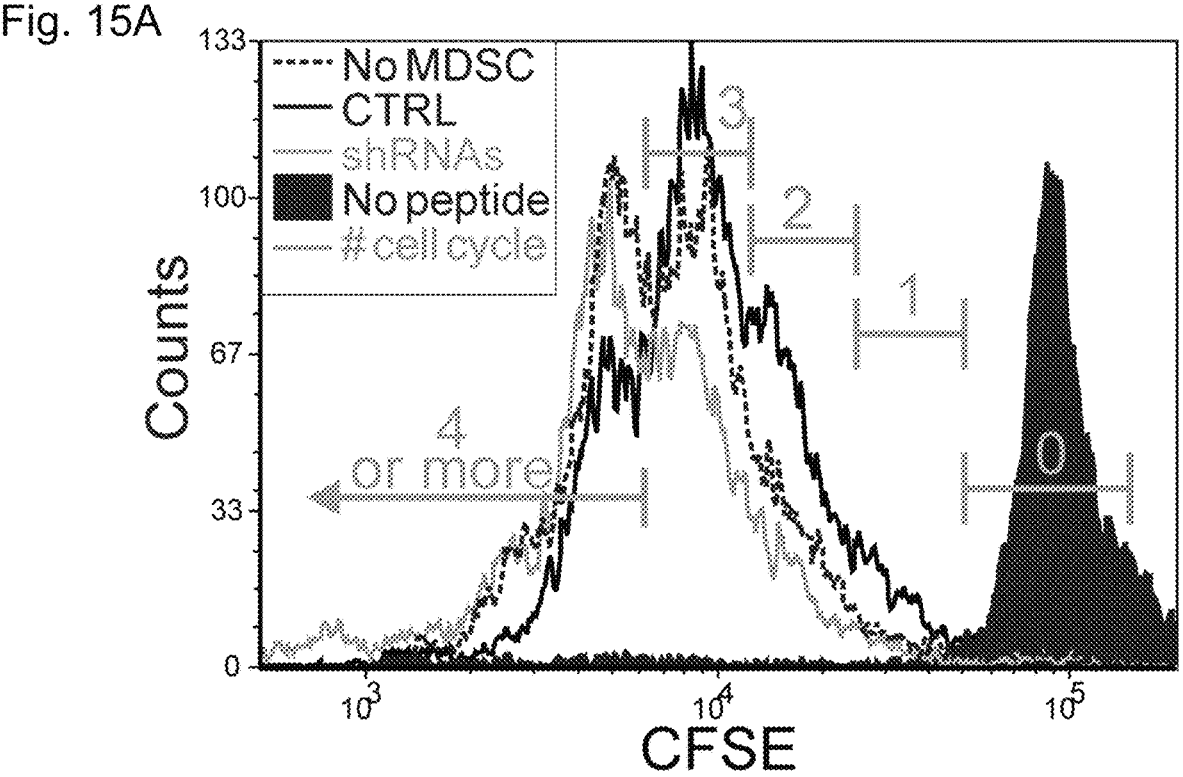
FIGS. 15A and 15B demonstrate that leukocytes from CCR silenced mice showed a lower suppressive activity. Tumor educated myeloid cells from CCR silenced mice failed to be licensed into suppressive cells. CD11b+splenocytes were magnetically purified by 4T1 tumor bearing mice treated with scrambled shRNA (black line and histogram) or with the mixture of shRNA specific for CCR-1, -2, -5, and -7 (gray line and histogram). $5 \times 10^4$ CD11b+ cells were than plated with 10^6Thy1.2 splenocytes and 10^5 CFSE labeled, HA specific, Thy1.1+CD8+ T cells. Clonotypic T cells cultured in the absence of CD11b+ cells were used as positive control (red line and histogram). Four days later, T cell proliferation was evaluated via FACS after gating on CD8+Thy1.1+LIVE population.
Figure 15B:
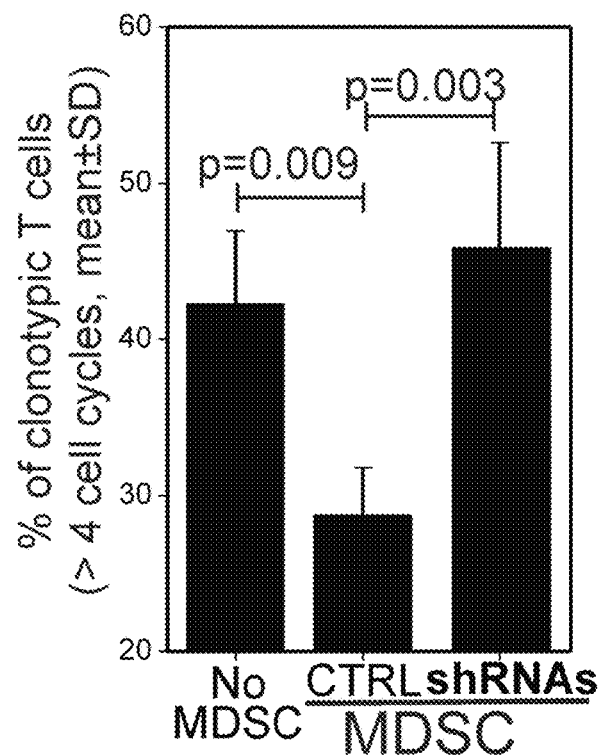
Figure 16A:
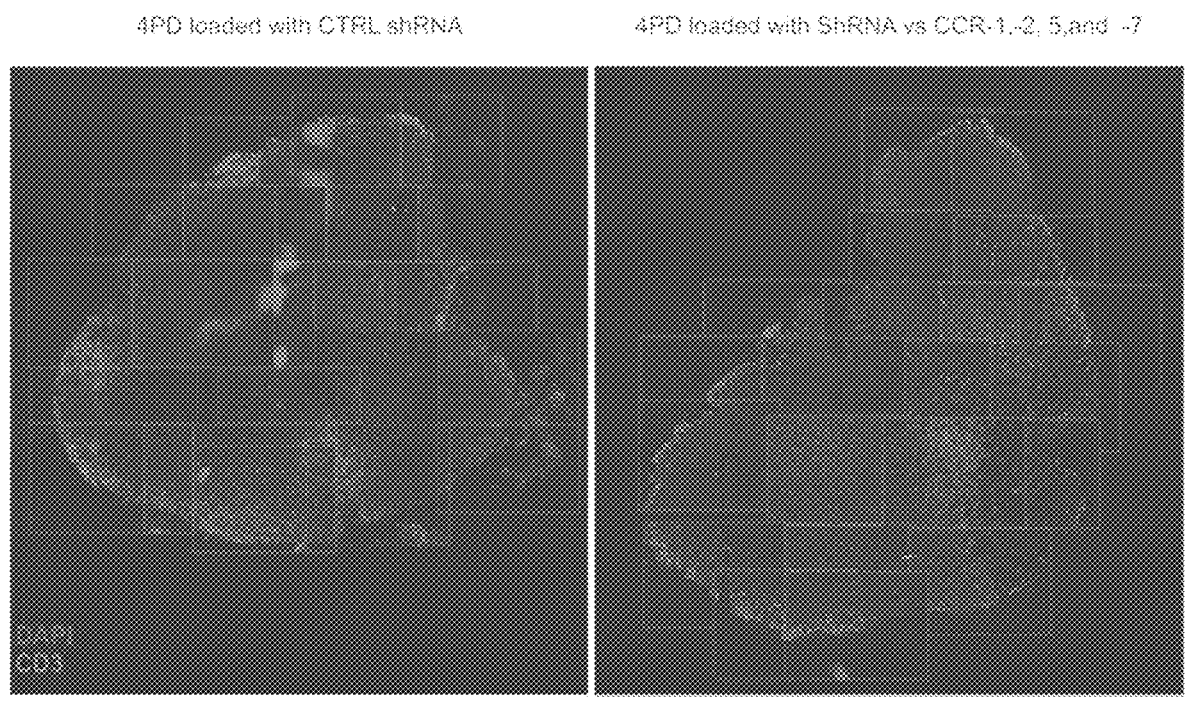
FIGS. 16A and 16B demonstrate that simultaneous silencing of CCR-1, -2, -5, and -7 promotes a measurable antitumor effect and a higher infiltration of CD3 cells in the tumor in vivo. Targeted silencing of CCR-1, -2, -5, and -7 increases the number of tumor infiltrating CD3+ T cells.
Figure 16B:
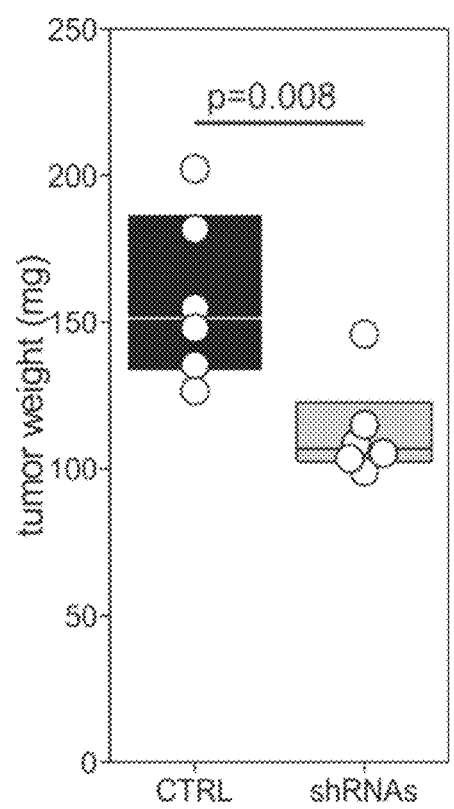

One of the biggest problems in the functional dissection of molecular pathways in the myeloid cells in vivo stand on the existence of redundant, integrating, and/or synergistic pathways that make currents genetic approaches inadequate. The role of chemokine receptors (CCR) is one of the most relevant examples. Indeed, a chemokine receptor can bind different chemokines and the same chemokine can bind different receptors. Moreover, a signal from one chemokine receptor can vanish the inhibition of another CCR, by activating the same intracellular pathway. Moreover, simultaneous activation of multiple CCR can result in the integration of the signals leading to the activation of a different pathway by the formation of heterodimers between the CCRs or the down-stream signaling molecules (i.e. STATs). Because 4PD allows the simultaneous delivery of different shRNA (each targeting a specific shRNA) to the myeloid lineage, the role of CCR in myeloid cell homing and differentiation can be determined. Briefly, FIG. 14, Balb/c mice were challenged on day 0 with the 4T1 mammary carcinoma. ShRNA against CCR-1, -2, -5, and -7 were complexed with the 4PD and administered systemically via intravenous injection on day 3, 5, 7 and 12. On day 13, mice were sacrificed and the single cell suspension from the tumor and spleen was analyzed. As shown in FIG. 14, this treatment induced important changes in the myeloid composition in the tumor and in the spleen. Functional analysis of CD11b purified by the spleen or the tumor of treated mice, revealed that in vivo CCR silencing drastically reduced MDSCs suppressive activity (FIG. 15). Furthermore, immune fluorescence microscopy analysis (FIG. 16) of CD3+ T cells infiltrating the tumor reveals an important accumulation of T lymphocytes within the tumor suggesting that CCR silencing in the myeloid lineage can revert MDSCs suppression and allow the priming of a tumor specific immune response. These data clearly indicate that at least one of the different chemokine receptor evaluated play a key role in myeloid cell trafficking.

Figure 17:
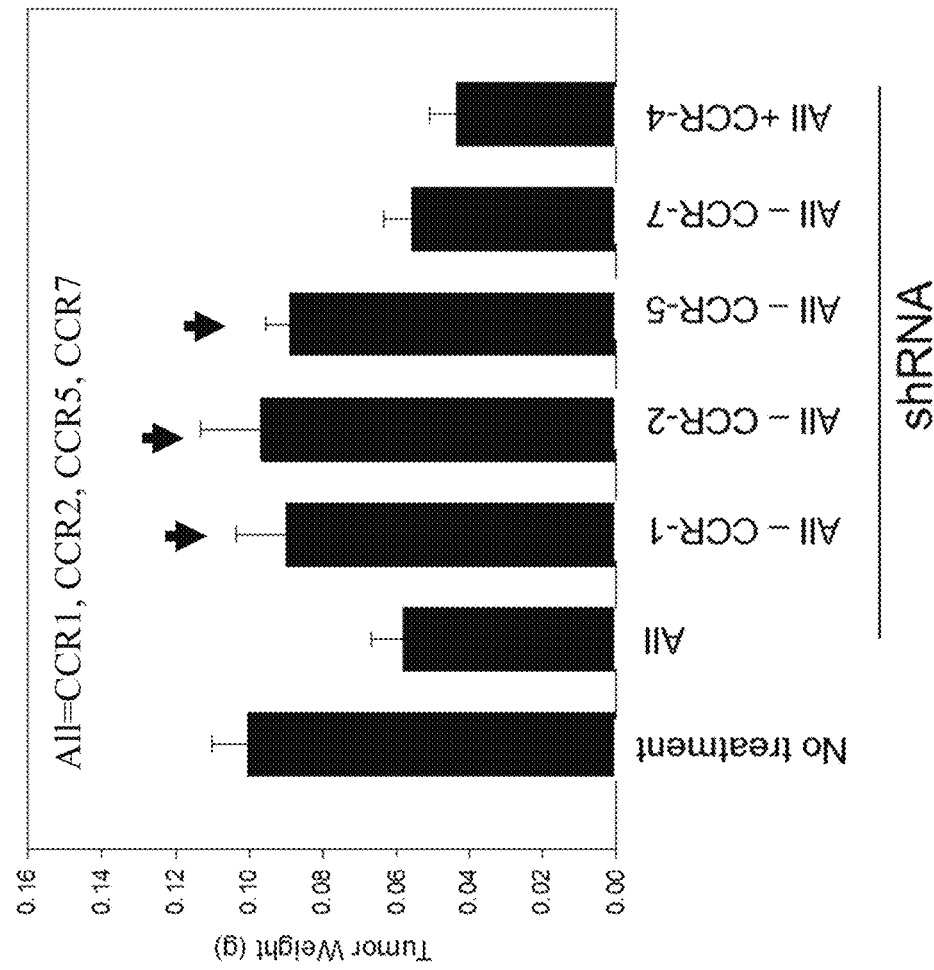
FIG. 17 demonstrates that CCR1, CCR2, and CCR-5 silencing is necessary for the observed anti-tumor effect. Briefly, the experiments described in FIGS. 14, 15, and 16, were repeated and group silencing all the chosen CCR but one were included. Tumor weight at day 13 is reported. This analysis indicates that CCR2, CCR1 and CCR5 are involved.

To determine which of these CCR was (were) important in the observed anti-tumor effect, the experiment was repeated including additional groups in which all the chosen CCR but one were silenced. Tumor weight at day 13 was chosen as read-out. As shown in FIG. 17, simultaneous silencing of CCR-1, -2, -5 and -7 drastically reduced tumor progression of approximately 50%. No differences are detectable if CCR4 specific shRNA is added or CCR7 specific shRNA is omitted. Conversely, the anti-tumor effect completely vanished when any of the shRNA specific for CCR1, CCR2, or CCR5 are omitted. Thus, these data demonstrate that silencing of CCR-1, -2, and -5 plays a key role in the observed antitumor effect.

Taken together, these experiments further confirm that multiple shRNA can be simultaneously loaded into the 4PD platform and functionally delivered to the myeloid cells in tumor bearing hosts.

Example 13—Therapeutic Use of 4PD to Modulate the Differentiation of Tumor Associated Myeloid Cells Via Targeted Silencing of CCR1 and CCR5

Myeloid cells are the most abundant type of hematopoietic cells in the immune system and have a huge diversity of physiological and pathological functions[1]. Depending on their intrinsic polarization, myeloid cells either promote or restrain tumor progression.

In advanced cancer, normal myelopoiesis is altered toward the expansion of cells with immunosuppressive and pro-tumoral functions hereafter named tumor-educated myeloid cells (TEMCs)[1,2]. This heterogeneous population includes: monocytes, immature myeloid cells, neutrophils, tumor associated macrophages (TAMs), dendritic cells (DCs) and myeloid-derived suppressor cells (MDSCs). The two main subsets of MDSCs, defined as granulocytic ($Ly6G^+$gMDSC) or monocytic ($Ly6C^+$mMDSC) MDSCs, are functionally and phenotypically different[3,4]. TEMCs pro-tumoral activity is not only limited in preventing immune-surveillance but, also, they play a key role in many immune-independent mechanisms. For example, MDSCs and TAMs promote metastases by facilitating tumor invasion in the surrounding tissue, via MMP9 secretion[5], and by preparing the distant site for neoplastic cell colonization by providing immune protection and tumor favoring factors to the seeded neoplastic cells. TEMCs can also promote tumor angiogenesis by being incorporated in the tumor blood vessels and by regulating VEGF bio-availability[6]. Finally, they can provide important factors for tumor growth and survival.

Given the above TEMC phenotypes, their presence at the tumor site expectedly correlates with increased vascular density and worse clinical outcomes in several types of human cancer[8,9]. For example, intra-tumoral TEMCs, similar to gMDSC, are an independent prognostic factor for overall survival in metastatic and localized renal clear cell carcinoma[10,11] and in head and neck squamous cell carcinoma[12]. Increased TEMC abundance in breast cancer patients predicts worsened metastasis-free survival[13,14]. Furthermore, TEMC infiltration is associated with tumor grade and aggressiveness in patients with glioma and pancreatic cancers[15,16].

However, the presence of myeloid cells and, in particular, neutrophils in the tumor has also been associated with a higher survival rate in gastric cancer[17] and a favorable prognosis in colorectal cancer[18]. In the early stage of lung cancer, tumor-associated myeloid cells can stimulate a T cell responses suggesting that they may orchestrate the global antitumor immunity[19]. Furthermore, neutrophils have been proposed to mediate the rituximab and trastuzumab antibody-dependent cell-mediated cytotoxicity in breast cancer[20] and lymphoma[21-23].

Resolving the controversy that neutrophils can play a pro- or anti-tumoral role seems to lie in both the intrinsic plasticity and heterogeneity of these cells. For example, two similar subsets of neutrophil-like cells can be identified in mouse and human[24]. The high density $FSC-A^{low}CD11b^{int}$ neutrophils (HDN), consistent with classical neutrophils, are anti-tumoral, while the low density $FSC-A^{high}CD11b^{high}$ neutrophils (LDN), phenotypically similar to gMDSCs, are characterized by a strong immunosuppressive, pro-tumoral activity[24].

Figure 19A:
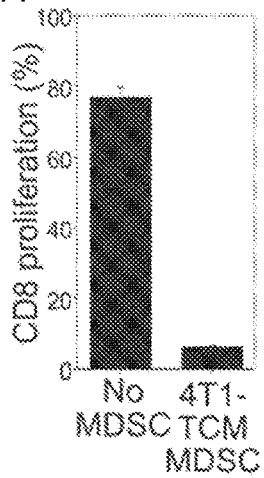
FIGS. 19A-19D demonstrate that CCR1 and CCR5 blockade modifies TEMC differentiation.
Figure 19B:
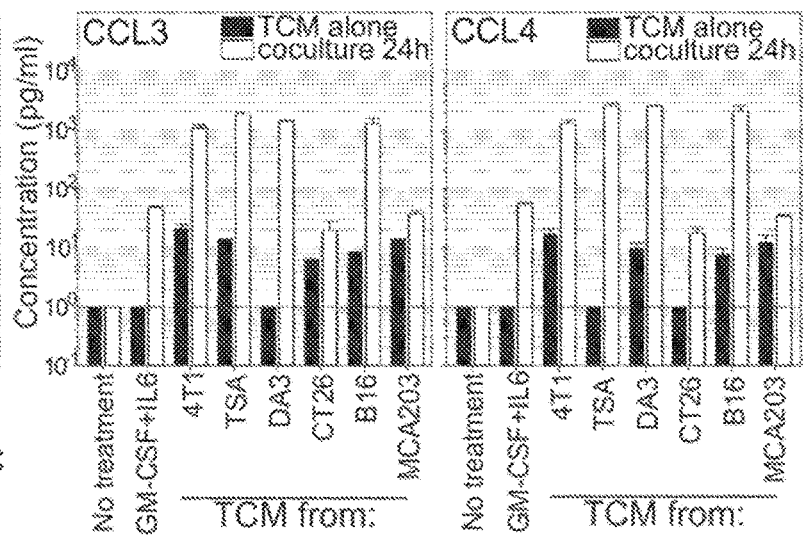
Figure 19C:
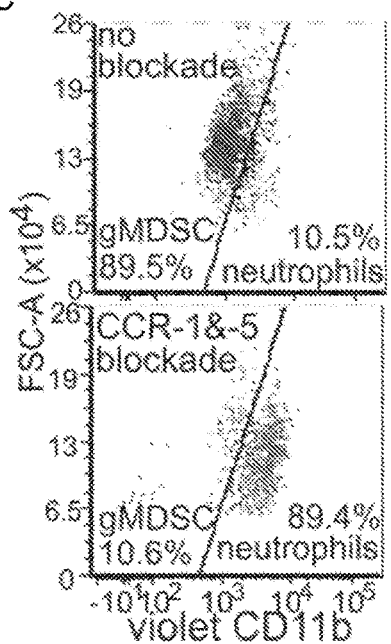
Figure 19D:
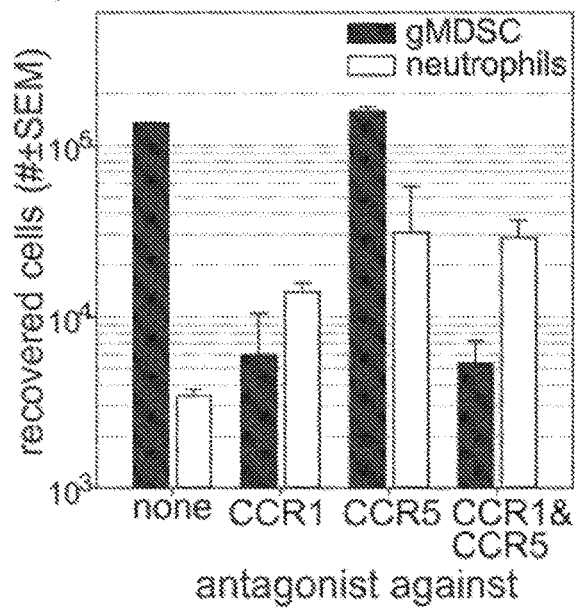

While we were evaluating the chemokines secreted by different mouse tumor cell lines, we made the unexpected discovery that CCL3 and CCL4 were secreted by BM cells undergoing TEMC differentiation (FIG. 19A) with tumor conditioned media (TCM) from the 4T1 cell line. Further experiments revealed that this phenomenon was not particular to the 4T1 supernatant but rather a generalized finding (FIG. 19B). Not only do BM cells produce CCL3 and CCL4 in response to the supernatant of mammary (4T1, DA3, and TSA) and colon (CT26) carcinoma, melanoma (B16) and fibrosarcoma (MCA203), but also in response to GM-CSF and IL-6, factors that are sufficient to induce MDSC differentiation[25]. No expression differences were found for other chemokines evaluated (e.g. CCL2 and CCL5). To determine whether CCL3 and 4 secretion was functionally important in TEMC differentiation, BM cells were cultured in the presence of TCM with or without blockade of the CCL3 and CCL4 receptors CCR1 and CCR5 using the specific antagonists BX471[26] and maraviroc[27], respectively. The use of both inhibitors caused profound changes in the resulting myeloid cell composition. In the monocytic compartment, CCR1 and CCR5 blockade significantly increased the Ly6C/Ly6G ratio as well as the number of $Ly6C^{high}$ monocytes. In the granulocytic $Ly6G^+Lin^-$ compartment, simultaneous blockade of CCR1 and 5 induced the appearance of $CD11b^{low}FSC-A^{low}$ neutrophils (FIG. 1C) with a concomitant decrease of $CD11b^{high}FSCA^{high}$ gMDSCs. When cell recovery was evaluated (FIG. 19D), the data were even more impressive and suggested a cumulative/synergistic action of targeting both CCR1 and 5.

Figures 20A, 20B:
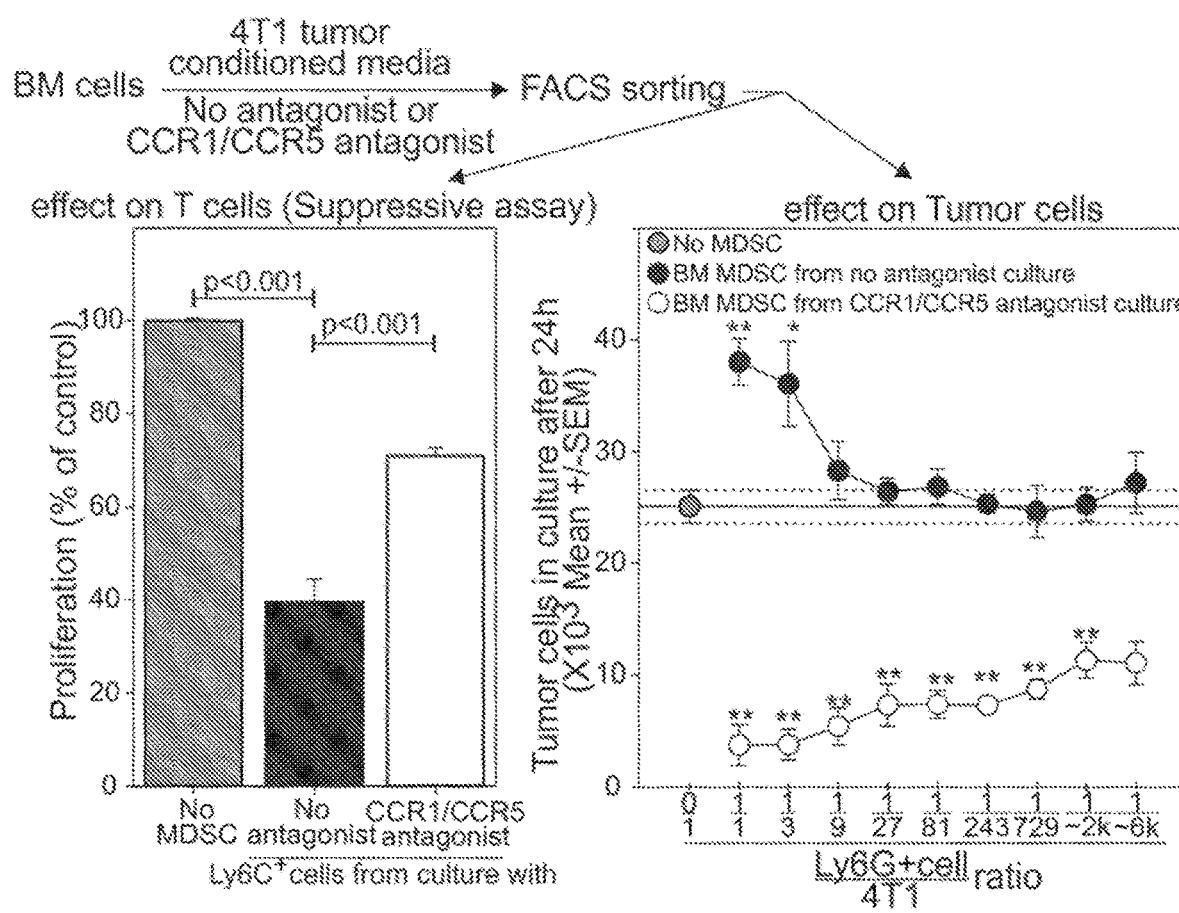
FIGS. 20A and 20B demonstrate that CCR1 and CCR5 blockade restrains mouse MDSCs differentiation and promote the accumulation of myeloid cells with an anti-tumoral phenotype. BM cells were cultured with supernatant (30%) of 4T1 cells for 4 days in the presence or in the absence of CCR1 and CCR5 antagonist. Ly6C+ and Ly6G+ cells were sorted by FACS and cultured with CFSE labelled HA specific CD8+ T cells (FIG. 20A) or with 4T1 luciferase cells (FIG. 20B).

Functional analysis of BM derived MDSCs differentiated in the presence or in the absence of CCR1 and CCR5 blockade reveals that the observed phenotypic differences (FIG. 19) correlate with important functional changes. Briefly, as reported in FIG. 20, BM cells were cultured with 4T1 tumor conditioned media in the presence or in the absence of CCR1 and CCR5 antagonists as described above (FIG. 19). Four days later $Ly6C^+$ and $Ly6G^+$ cells were sorted and tested for their suppressive activity (FIG. 20A) on clonotypic T cells and their effect on 4T1 cells (FIG. 20B).

To test MDSCs suppressive activity, $Ly6C^+$ or $Ly6G^+$ cells were cultured as a third part with CFSE labelled, Hemagglutinin (HA) specific, $CD8^+T$ cells stimulated with the relevant peptide. Three days later T cell proliferation was evaluated by FACS. $Ly6C^+$ cells isolated from cultures with no antagonist can reduce T cell proliferation of almost 60% (FIG. 20A). Interestingly, $Ly6C^+$ cells isolated from cultures with CCR1 and CCR5 blockade shows reduce suppression (FIG. 20A). No suppressive activity was detected in the Ly6G$^+$ cells isolated from either culture (not shown).

To test the effect of MDSCs (differentiated in vitro with or without CCR1/CCR5 blockade) on tumor cells, sorted Ly6C$^+$ or Ly6G$^+$ cells were cultured with 4T1 luciferase cells at different ratio. After 24 h tumor cell number was evaluated via luciferase assay. Interestingly, gMDSC (black circle) differentiated in the absence of CCR1 and CCR5 antagonist significantly increase 4T1 cell recovery suggesting a pro-tumoral function (please compare the black circle with the 4T1 cultured for 24 h with no additional cells, gray circle). In striking contrast, Ly6G$^+$ cells sorted from the culture with CCR1/CCR5 blockade (white circle), not only do not enhance tumor cell proliferation but, instead, drastically reduce the number of 4T1 cells in culture. Similar data were obtained with Ly6C$^+$ cells (data not shown).

Figure 21:
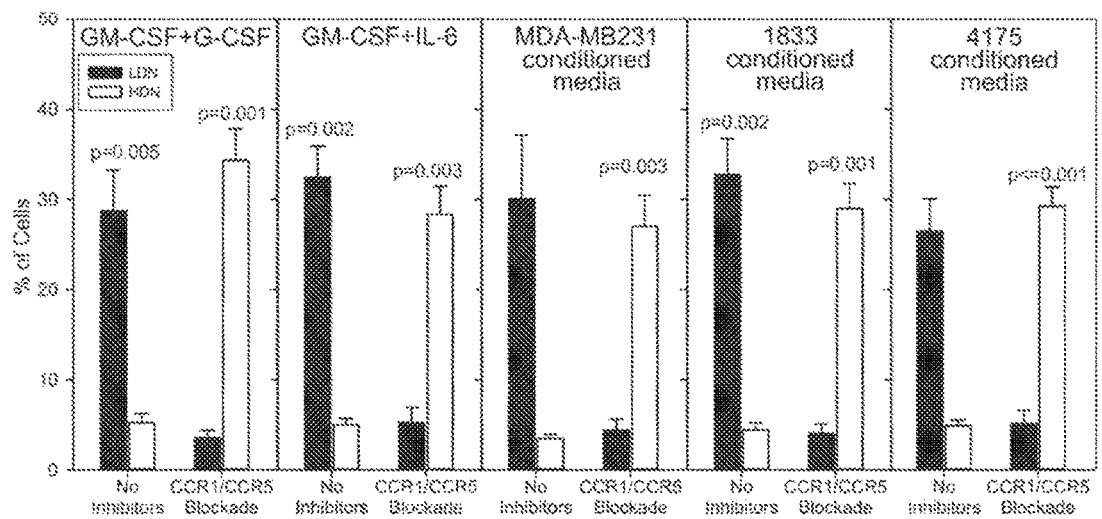
FIG. 21 demonstrates that CCR1 and CCR5 blockade restrains human LDN/MDSC differentiation and promote the accumulation of HDN myeloid cells with an anti-tumoral phenotype. CD3 depleted myeloid precursors from umbilical cord blood were cultured in the presence with GM-CSF and G-CSF, with GM-CSF and IL-6, or with the conditioned media (30%) from the MDA-MB231, 1833, or 4175 mammary carcinoma cell lines. High density neutrophils (HDN, $CD15^{int}$, $CD66b^{low}FSC-A^{low}$, $CD11b^{low}$cells) and low density neutrophils (LDN, $CD15^{int}$, $CD66b^+FSC-A^{high}$, $CD11b^{high}$cells) were calculated as percentage of alive cells by FACS. Data derived from three independent experiments. T-Test p value is reported.

In order to extend these findings to human, CD3 depleted hematopoietic precursors from human Umbilical cord blood were cultured for 4 days with A) GM-CSF and G-CSF, B) GM-CSF and IL6, C) tumor conditioned supernatant from MDA-MD231 human mammary carcinoma, D) tumor conditioned supernatant from 1833 human mammary carcinoma, or E) tumor conditioned supernatant from 4175 human mammary carcinoma. In half of the well BX471[26] and maraviroc[27], antagonists of CCR1 and CCR5 respectively, were added. Four days later the number of HDN and LDN cells were evaluated as described in reference[24]. Data shows that CCR1 and CCR5 blockade is sufficient to drastically reduce the pro-tumoral LDN while significantly increase the recovery of anti-tumoral HDN (FIG. 21).

Figure 22A:
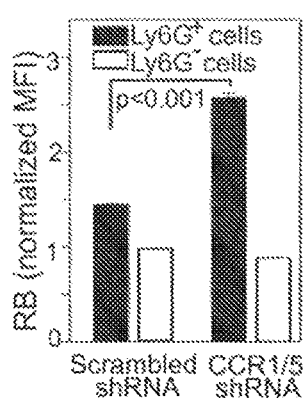
FIGS. 22A-22C demonstrate that 4PD-mediated CCR1/CCR5 silencing on tumor infiltrating Tumor-educated-myeloid cells (TEMC) beneficially modulate tumor microenvironment.
Figure 22B:
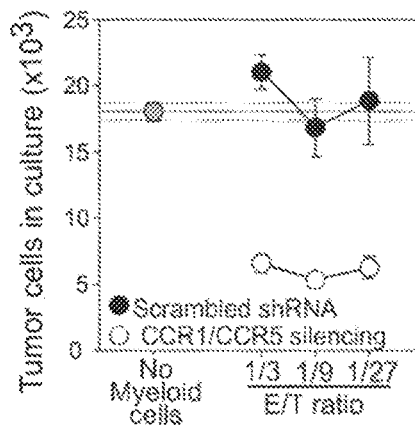
Figure 22C:
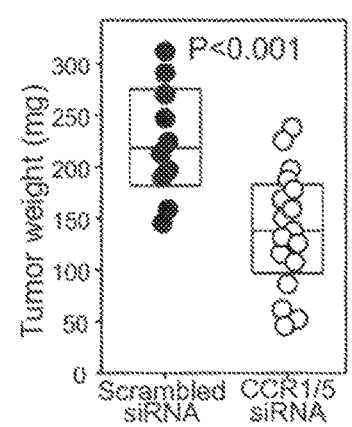

To evaluate whether 4PD may by silencing CCR1 and CCR5 in tumor infiltrating myeloid cells convert pro-tumoral myeloid cells into cells capable to kill the tumor, the following set of experiments was performed. Briefly, Balb/c mice were challenged on day 0 with the 4T1 mammary carcinoma and treated on days 3, 6, 8, 10 and 12 with 4PD loaded with shRNAs against CCR1 and 5 or with scrambled shRNA. On day 13, the mice were euthanized. Part of the tumor was analyzed via IHC, and another part was used to evaluate the tumoricidal action of tumor-infiltrating myeloid cells. Immuno-fluorescence analysis (FIG. 22B, FIG. 22C) of the Ly6G$^+$cells (Red) revealed that CCR1/CCR5 silencing significantly upregulated the expression of Retinoblastoma (RB, green), a protein that allows to discriminate normal RB$^+$neutrophils from RB$^-$ gMDSC[28] suggesting important changes in tumor infiltrating TEMC. Ex vivo functional analysis, reveals that CD11b$^+$cells isolated from the mice treated with CCR1/CCR5 shRNA (open circle) can exert an important cytotoxic activity against 4T1 cell whereas CD11b$^+$cells from scrambled shRNA treated mice (black circle) do not (FIG. 22D). This functional activity may explain the reduction of tumor size observed in the mice treated with 4PD loaded with CCR1 and CCR5 shRNA compared to control (FIG. 22E).

Figure 23:
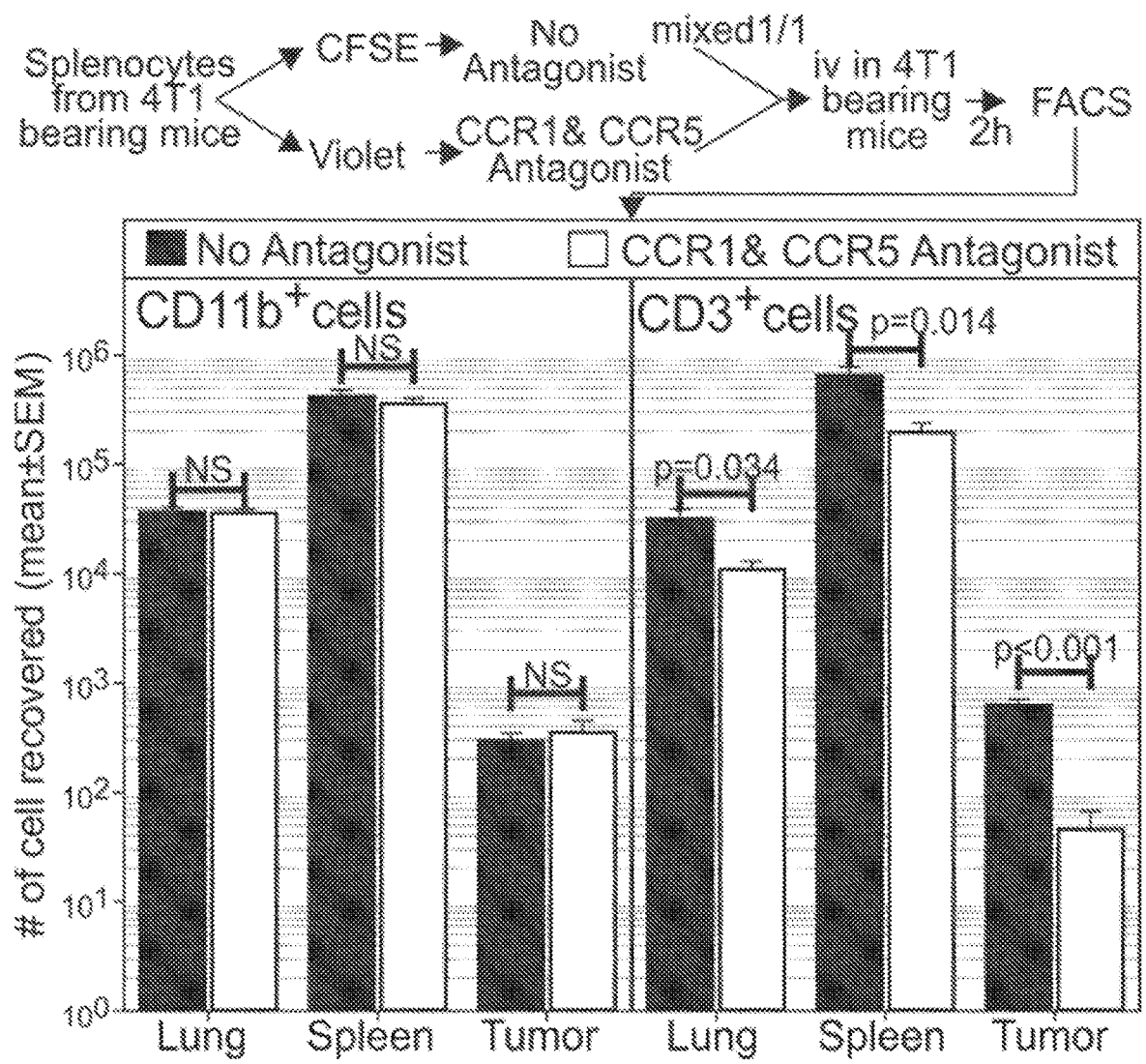
FIG. 23 demonstrates that CCR1 and CCR5 blockade does not affect TEMC trafficking to the tumor. Splenocytes from 4T1 bearing mice were divided in two aliquots and either CFSE labelled and left untreated or violet labelled and treated with CCR1 and CCR5 antagonists for 1 h. Aliquots were admixed in equal cell number and injected iv in 4T1 bearing mice. 2 h later lung, spleen and tumor were harvested and the number of CD11b+ or CD3+cells evaluated by FACS within the CFSE+ or violet+ cells.

To exclude that CCR1 and CCR5 silencing was affecting myeloid trafficking and not myeloid cell repolarization, in vivo leukocyte trafficking experiments were performed (FIG. 23). Briefly, splenocytes from 4T1 bearing mice were divided in two aliquots and either CFSE labelled and left untreated or violet labelled and treated with CCR1 and CCR5 antagonists for 1 hour. Aliquots were admixed in equal cell number and injected i.v. in 4T1 bearing mice. Two hours later lung, spleen and tumor were harvested and the number of CD11b' or CD3$^+$ cells evaluated by FACS within the CFSE or violet$^+$ cells. While CD3$^+$cells failed to reach the tumor when CCR1 and CCR5 where inhibited, no differences were observed between myeloid cells treated with CCR1 and CCR5 antagonists and the one left untreated (FIG. 23). These data clearly indicate that CCR1 and CCR5 blockade does not alter myeloid cells trafficking to the tumor but rather their differentiation.

Taken together, these data suggest that CCR1 and CCR5 signaling may play an important role in myeloid cell polarization inducing suppressive and pro-tumoral MDSCs. Conversely, CCR1 and CCR5 blockade allows the generation of tumoricidal neutrophils. Taken together, these data indicate that targeted CCR1/CCR5 silencing alters myeloid compartment and promotes the intra-tumoral accumulation of CD11b$^+$ cells with tumoricidal activity. Thus, 4PD can be used therapeutically to repolarize myeloid cells toward a tumoricidal phenotype. Considering the important role that HDN neutrophils play in the antitumor response (i.e. antibody-dependent cell-mediated cytotoxicity) this strategy should synergize with anti-tumor antibodies therapies such trastuzumab and ritubimax.

Example 14—4PD can Deliver MicroRNA to Myeloid Cells of a Tumor Host

Figure 18:
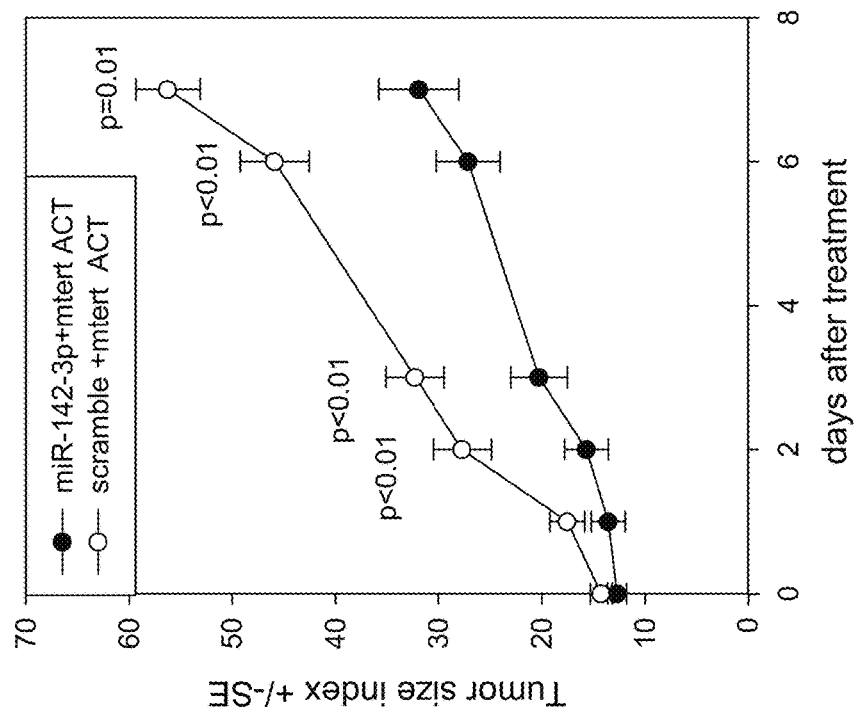
FIG. 18 demonstrates that 4PD can be used to deliver therapeutic microRNA to tumor-educated myeloid cells. C57BL/6 mice were injected with MCA203 fibrosarcoma at day 0. When the tumor reached a diameter of approximately 4 mm, mice were treated with CTL specific for the peptide of mouse telomerase reverse transcriptase (mTERT). 4PD loaded with mir-142-3p or control RNA was given the day before and 3 days after the adoptive cell transfer (ACT). At least 5 mice in each group were used. As shown in the figure, mice treated with 4PD loaded with mir-142-3p, in association with ACT treatment present a significant delay in tumor growth and progression.

The development of HT-sequencing and dedicated microarray assays allows the identification of differentially expressed regulatory RNA (microRNA, miR) between normal and pathological condition. However, there is a need for high throughput functional screening that allow identification of which differentially expressed miR play a key role in myeloid cell differentiation. microRNA 142-3p, mir-142-3p, plays a key role in myeloid cell differentiation in cancer[13], and was tested in the context of the inventive nanoparticles. Briefly, C57BL/6 mice were injected with MCA203 fibrosarcoma at day 0. When the tumor reached a diameter of approximately 4 mm, mice were treated with CTL specific mouse telomerase reverse transcriptase (mTERT) tumor associated antigen. 4PD loaded with mir-142-3p or control RNA was administered the day before and 3 days after the adoptive cell transfer (ACT). As shown in FIG. 18, delivery of mir-142-3p to the myeloid compartment significantly delayed tumor progression indicating an important functional role of this microRNA. Of note, this experiment that was performed in less than 20 days gave similar results of the one performed using chimeric mice and that requires almost a year and conspicuous financial efforts[13].

These data demonstrate that microRNA can be delivered via 4PD and their role in myelopoiesis functionally screened in vivo.

Example 15—4PD can Recognize Early Hematopoietic Progenitor Cells

Bone marrow cells from C57Bl/6 mice were incubated for 10 minutes with 4PD loaded with Alexafluor 555 washed, counterstained with anti-lineage cocktail, anti-CD45, anti-Sca1, anti ckit, anti-CD34, anti-CD16/CD32, anti-CD150 and anti-CD48 antibodies, and analyzed by flow cytometry.

Figure 24A:
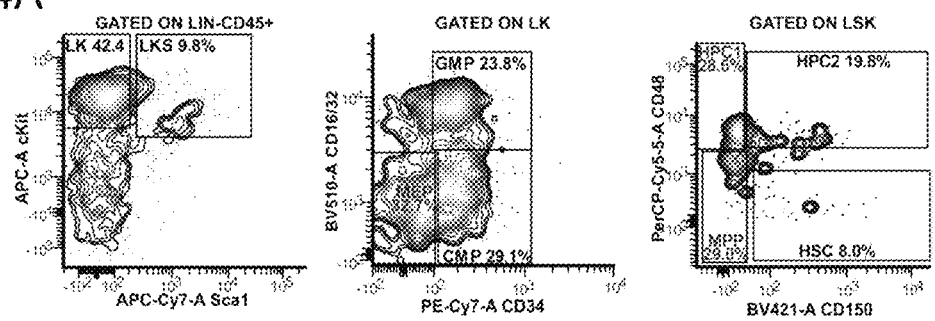
FIGS. 24A and 24B demonstrate that 4PD transfect early hematopoietic progenitor cells.
Figure 24B:
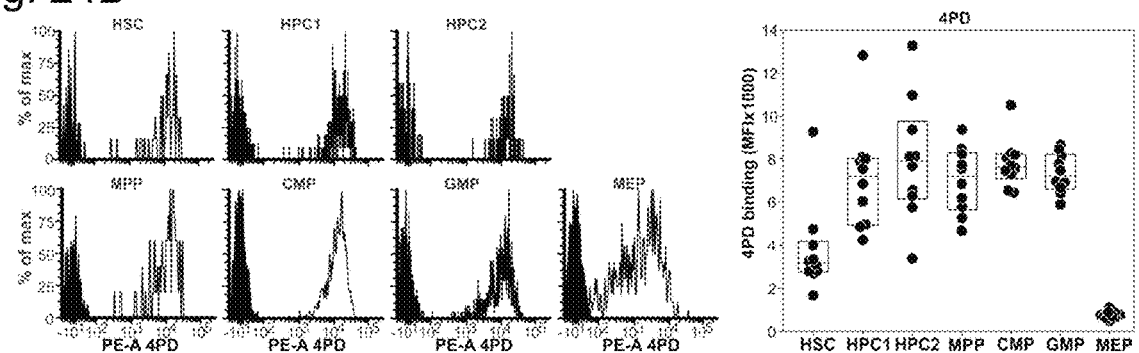

As shown in FIG. 24, 4PD is able to efficiently transfect mouse hematopoietic stem cells (HSC) mouse hematopoietic precursors (HPC1 and HPC2), Multipotent progenitors cells (MPP), common myeloid precursors (CMP), Granulocytes-monocyte precursors (GMP) and at lower level megakariocytes-erythrocyte precursors. Importantly, the viability of the cells after transfection was higher than 95%. The data provided herein demonstrate the possibility to transfect early hematopoietic cells efficiently allowing a better gene modulation.

Efficient and non-toxic methods to transfect hematopoietic precursors in vitro and in vivo are still lacking. The data provided herein demonstrates that IL4Ra is also expressed on early hematopoietic precursors and that 4PD can bind and efficiently transfect hematopoietic precursors starting for the hematopoietic progenitor cell (HPC) phase. Thus, 4PD offers an important opportunity for the non-toxic, non-viral and efficient gene modulation of hematopoietic cells. This is particularly important considering 1) the new emerging data that hematopoietic stem and precursor cells are found in circulation in many human diseases including, but not limited to, cancer, chronic inflammation and infection, emergency hematopoiesis or after exposure to radiation; 2) that their transient manipulation allows to modulate the immune response to cancer and other inflammatory diseases, and 3) that 4PD allows the in vivo transfection of IL4Ra+ cells including HSPCs in the tumor bed.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification, are incorporated herein by reference, in their entireties or in relevant part, as would be apparent from the context of their citation.

From the foregoing it will be appreciated that, although specific embodiments of the invention have been described herein for purposes of illustration, various modifications may be made without deviating from the spirit and scope of the invention.

REFERENCES CITED

1. Roth, F., et al. Aptamer-Mediated Blockade of IL4Ralpha Triggers Apoptosis of MDSCs and Limits Tumor Progression. Cancer Res 72, 1373-1383 (2012).
2. Serafini, P. & Bronte, V. Myeloid-Derived Suppressor Cells in Cancer. in Tumor-Induced Immune Suppression Mechanisms and Therapeutic Reversal (eds. Gabrilovich, D. I. & Hurwitz, A. A.) 157-195 (Springer, New York, 2008).
3. Gallina, G., et al. Tumors induce a subset of inflammatory monocytes with immunosuppressive activity on CD8+ T cells. J Clin Invest 116, 2777-2790 (2006).
4. Bronte, V., et al. IL-4-induced arginase 1 suppresses alloreactive T cells in tumor-bearing mice. J Immunol 170, 270-278 (2003).
5. Galizzi, J. P., Zuber, C. E., Cabrillat, H., Djossou, 0. & Banchereau, J. Internalization of human interleukin 4 and transient down-regulation of its receptor in the CD23-inducible Jijoye cells. J Biol Chem 264, 6984-6989 (1989).
6. Yao, G., et al. Identification of core functional region of murine IL-4 using peptide phage display and molecular modeling. Int Immunol 18, 19-29 (2006).
7. Zhang, J. L., Simeonowa, I., Wang, Y. & Sebald, W. The high-affinity interaction of human IL-4 and the receptor alpha chain is constituted by two independent binding clusters. J Mol Biol 315, 399-407 (2002).
8. Hage, T., Sebald, W. & Reinemer, P. Crystal structure of the interleukin-4/receptor alpha chain complex reveals a mosaic binding interface. Cell 97, 271-281 (1999).
9. Weed, D. T., et al. Tadalafil reduces myeloid-derived suppressor cells and regulatory T cells and promotes tumor immunity in patients with head and neck squamous cell carcinoma. Clin Cancer Res 21, 39-48 (2015).
10. Kortylewski, M., et al. Inhibiting Stat3 signaling in the hematopoietic system elicits multicomponent antitumor immunity. Nat Med 11, 1314-1321 (2005).
11. Cheng, F., et al. A critical role for Stat3 signaling in immune tolerance. Immunity 19, 425-436 (2003).
12. Vasquez-Dunddel, D., et al. STATS regulates arginase-I in myeloid-derived suppressor cells from cancer patients. J Clin Invest 123, 1580-1589 (2013).
13. Sonda, N., et al. miR-142-3p prevents macrophage differentiation during cancer-induced myelopoiesis. Immunity 38, 1236-1249 (2013).

REFERENCES FOR EXAMPLE 13

1 Gabrilovich, D. I., Ostrand-Rosenberg, S. & Bronte, V. Coordinated regulation of myeloid cells by tumours. Nat Rev Immunol 12, 253-268, doi:10.1038/nri3175 (2012).
2 Marvel, D. & Gabrilovich, D. I. Myeloid-derived suppressor cells in the tumor microenvironment: expect the unexpected. J Clin Invest 125, 3356-3364, doi:10.1172/jci80005 (2015).
3 Serafini, P. Myeloid derived suppressor cells in physiological and pathological conditions: the good, the bad, and the ugly. Immunologic Research, 1-13, doi:10.1007/s12026-013-8455-2 (2013).
4 Gabrilovich, D. I. et al. The terminology issue for myeloid-derived suppressor cells. Cancer Res 67, 425; author reply 426, doi:10.1158/0008-5472.CAN-06-3037 (2007).
5 Condamine, T., Ramachandran, I., Youn, J. I. & Gabrilovich, D. I. Regulation of tumor metastasis by myeloid-derived suppressor cells. Annu Rev Med 66, 97-110, doi:10.1146/annurev-med-051013-052304 (2015).
6 Yang, L. et al. Expansion of myeloid immune suppressor Gr+CD11b+ cells in tumor-bearing host directly promotes tumor angiogenesis. Cancer Cell 6, 409-421 (2004).
7 Serafini, P. Myeloid derived suppressor cells in physiological and pathological conditions: the good, the bad, and the ugly. Immunol Res 57, 172-184, doi:10.1007/s12026-013-8455-2 (2013).
8 Steidl, C. et al. Tumor-associated macrophages and survival in classic Hodgkin's lymphoma. N Engl J Med 362, 875-885, doi:10.1056/NEJMoa0905680 (2010).
9 Zhang, J., Patel, L. & Pienta, K. J. CC chemokine ligand 2 (CCL2) promotes prostate cancer tumorigenesis and metastasis. Cytokine Growth Factor Rev 21, 41-48, doi: 10.1016/j.cytogfr.2009.11.009 (2010).
10 Donskov, F. & von der Maase, H. Impact of immune parameters on long-term survival in metastatic renal cell carcinoma. Journal of clinical oncology: official journal of the American Society of Clinical Oncology 24, 1997-2005, doi:10.1200/JCO.2005.03.9594 (2006).
11 Jensen, H. K. et al. Presence of intratumoral neutrophils is an independent prognostic factor in localized renal cell carcinoma. Journal of clinical oncology: official journal of the American Society of Clinical Oncology 27, 4709-4717, doi:10.1200/JCO.2008.18.9498 (2009).
12 Trellakis, S. et al. Peripheral blood neutrophil granulocytes from patients with head and neck squamous cell carcinoma functionally differ from their counterparts in healthy donors. International journal of immunopathology and pharmacology 24, 683-693 (2011).

13 Noh, H., Eomm, M. & Han, A. Usefulness of pretreatment neutrophil to lymphocyte ratio in predicting disease-specific survival in breast cancer patients. Journal of breast cancer 16, 55-59, doi:10.4048/jbc.2013.16.1.55 (2013).
14 Azab, B. et al. Usefulness of the neutrophil-to-lymphocyte ratio in predicting short- and long-term mortality in breast cancer patients. Ann Surg Oncol 19, 217-224, doi:10.1245/s10434-011-1814-0 (2012).
15 Fossati, G. et al. Neutrophil infiltration into human gliomas. Acta neuropathologica 98, 349-354 (1999).
16 Reid, M. D. et al. Tumor-infiltrating neutrophils in pancreatic neoplasia. Mod Pathol 24, 1612-1619, doi:10.1038/modpathol.2011.113 (2011).
17 Caruso, R. A. et al. Prognostic value of intratumoral neutrophils in advanced gastric carcinoma in a high-risk area in northern Italy. Mod Pathol 15, 831-837, doi:10.1097/01.MP.0000020391.98998.6B (2002).
18 Hirt, C. et al. Colorectal carcinoma infiltration by myeloperoxidase-expressing neutrophil granulocytes is associated with favorable prognosis. Oncoimmunology 2, e25990, doi:10.4161/onci.25990 (2013).
19 Eruslanov, E. B. et al. Tumor-associated neutrophils stimulate T cell responses in early-stage human lung cancer. J Clin Invest 124, 5466-5480, doi:10.1172/jci77053 (2014).
20 Stockmeyer, B. et al. Polymorphonuclear granulocytes induce antibody-dependent apoptosis in human breast cancer cells. J Immunol 171, 5124-5129 (2003).
21 Hernandez-Ilizaliturri, F. J. et al. Neutrophils contribute to the biological antitumor activity of rituximab in a non-Hodgkin's lymphoma severe combined immunodeficiency mouse model. Clin Cancer Res 9, 5866-5873 (2003).
22 Niitsu, N. et al. Phase I/II study of the rituximab-EPOCT regimen in combination with granulocyte colony-stimulating factor in patients with relapsed or refractory follicular lymphoma including evaluation of its cardiotoxicity using B-type natriuretic peptide and troponin T levels. Clin Cancer Res 11, 697-702 (2005).
23 Albanesi, M. et al. Neutrophils mediate antibody-induced antitumor effects in mice. Blood 122, 3160-3164, doi:10.1182/blood-2013-04-497446 (2013).
24 Sagiv, J. Y. et al. Phenotypic diversity and plasticity in circulating neutrophil subpopulations in cancer. Cell reports 10, 562-573, doi:10.1016/j.celrep.2014.12.039 (2015).
25 Marigo, I. et al. Tumor-induced tolerance and immune suppression depend on the C/EBPbeta transcription factor. Immunity 32, 790-802, doi:10.1016/j.immuni.2010.05.010 (2010).
26 Horuk, R. BX471: a CCR1 antagonist with anti-inflammatory activity in man. Mini Rev Med Chem 5, 791-804 (2005).
27 Van Der Ryst, E. Maraviroc—A CCR5 Antagonist for the Treatment of HIV-1 Infection. Frontiers in immunology 6, 277, doi:10.3389/fimmu.2015.00277 (2015).
28 Youn, J. I. et al. Epigenetic silencing of retinoblastoma gene regulates pathologic differentiation of myeloid cells in cancer. Nat Immunol 14, 211-220, doi:10.1038/ni.2526 (2013).

What is claimed is:

1. A PAMAM dendrimer conjugated to a peptide set forth in SEQ ID NO: 1.

2. The PAMAM dendrimer of claim 1, further comprising one or more nucleic acid molecules.

3. The PAMAM dendrimer of claim 2, wherein the one or more nucleic acid molecules is selected from the group consisting of DNA, RNA, shRNA, siRNA, miRNA, an antagomir and RNA sponge.

4. The PAMAM dendrimer of claim 2, wherein the one or more nucleic acid molecules is a shRNA.

5. The PAMAM dendrimer of claim 4, wherein the shRNA is selected from the group consisting of STAT3 shRNA, C-EBPβ shRNA, CCR1 shRNA, CCR2 shRNA and CCR5 shRNA.

6. The PAMAM dendrimer of claim 2, wherein the nucleic acid molecules comprise STAT3 shRNA and C-EBPβ shRNA.

7. The PAMAM dendrimer of claim 2 wherein the nucleic acid molecules comprise CCR1 shRNA, CCR2 shRNA and CCR5 shRNA.

8. The PAMAM dendrimer of claim 2, wherein the nucleic acid molecule comprises miR-142-3p.

9. The PAMAM dendrimer of claim 1, wherein the PAMAM dendrimer is selected from the group consisting of a aG4 dendrimer, G5 dendrimer, a G6 dendrimer and a G7 dendrimer.

10. A method of delivering a nucleic acid to a cell that expressed IL4Rα comprising contacting the cell with the PAMAM dendrimer of claim 3.

* * * * *